United States Patent [19]

Stanis et al.

[11] 4,135,241
[45] Jan. 16, 1979

[54] INVENTORY CONTROL, BED ALLOCATION AND ACCOUNTING DATA HANDLING SYSTEM

[75] Inventors: Eugene A. Stanis, Wheeling; Louis E. Philippa, Addison, both of Ill.

[73] Assignee: Medelco, Incorporated, Skokie, Ill.

[21] Appl. No.: 520,718

[22] Filed: Nov. 4, 1974

Related U.S. Application Data

[63] Continuation of Ser. No. 117,839, Feb. 22, 1971, abandoned, which is a continuation of Ser. No. 761,042, Sep. 20, 1968, abandoned.

[51] Int. Cl.² ............... G06F 3/08; G06F 15/22; G06F 15/24
[52] U.S. Cl. .................. 364/200; 235/385; 364/403
[58] Field of Search ........... 340/172.5, 147 R, 147 A, 340/147 CN, 150, 153; 444/1; 364/200 MS File, 900 MS File, 403, 404; 235/61.7 B, 379, 385

[56] References Cited

U.S. PATENT DOCUMENTS

| | | | |
|---|---|---|---|
| 2,910,238 | 10/1959 | Miles et al. | 340/153 X |
| 2,995,729 | 8/1961 | Steele | 364/200 |
| 3,002,181 | 9/1961 | Parsons et al. | 235/61.7 B X |
| 3,121,159 | 2/1964 | Rogal | 340/147 R X |
| 3,178,690 | 4/1965 | Masters et al. | 340/172.5 |
| 3,241,117 | 3/1966 | Schottle et al. | 340/153 |
| 3,245,045 | 4/1966 | Randlev | 340/172.5 |
| 3,248,701 | 4/1966 | Eisenstein et al. | 340/172.5 |
| 3,267,436 | 8/1966 | Alpert et al. | 364/900 |
| 3,293,612 | 12/1966 | Ling | 340/172.5 |
| 3,308,439 | 3/1967 | Tink et al. | 340/172.5 |
| 3,341,820 | 9/1967 | Grillmeier, Jr. et al. | 340/172.5 |
| 3,355,576 | 11/1967 | Childers et al. | 235/61.7 B |
| 3,400,378 | 9/1968 | Smith et al. | 235/61.7 B X |
| 3,445,633 | 5/1969 | Ratner | 235/61.7 B |
| 3,484,748 | 12/1969 | Greenblum et al. | 340/153 |
| 3,533,084 | 10/1970 | Cook et al. | 340/172.5 |
| 3,588,838 | 6/1971 | Felcheck | 364/900 |

*Primary Examiner*—Melvin B. Chapnick
*Attorney, Agent, or Firm*—Mason, Kolehmainen, Rathburn & Wyss

[57] ABSTRACT

A data handling system for a hospital or like establishment. The system keeps track of bed allocation, changes in inventory, and charges to patients, and also serves as a communication network for the hospital. Data is fed into the system in the form of pre-punched cards bearing patient information, inventory data, and commands or messages, and thus unskilled personnel can quickly feed data into the system without error. Message data is routed directly to teleprinters at addressed locations. Bed allocation and patient data, and charge and inventory data are respectively stored in separate magnetic drum storage areas. Searching facilities are provided which can locate desired data entries in either storage area and mark these entries for printout, and separate printout circuitry then transfers marked data items to the proper addresses in the proper format. At the end of each day, a final search is performed which produces a printout of all charges organized by patient number. A tally inventory search is also performed which produces a printout of inventory changes organized by item number and by department number. The tally search is cumulative, and a tally arithmetic unit summarizes inventory data for each separate item before printout. A running record is kept of each day's total charges, credits, and payments on account in a central core memory, and this record is continually updated by a central arithmetic unit.

17 Claims, 39 Drawing Figures

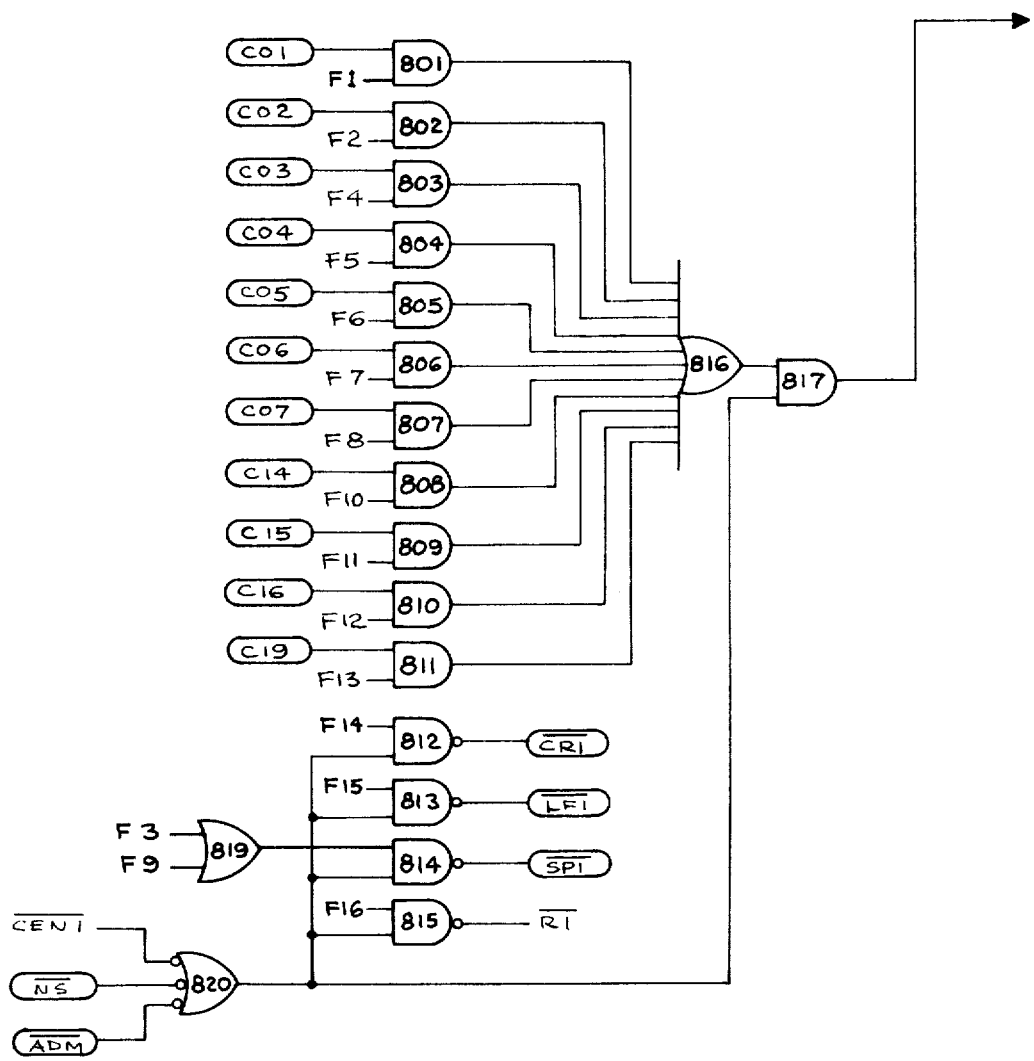
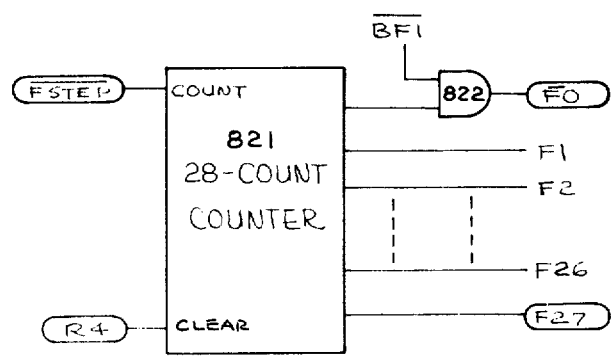
FIG. 8

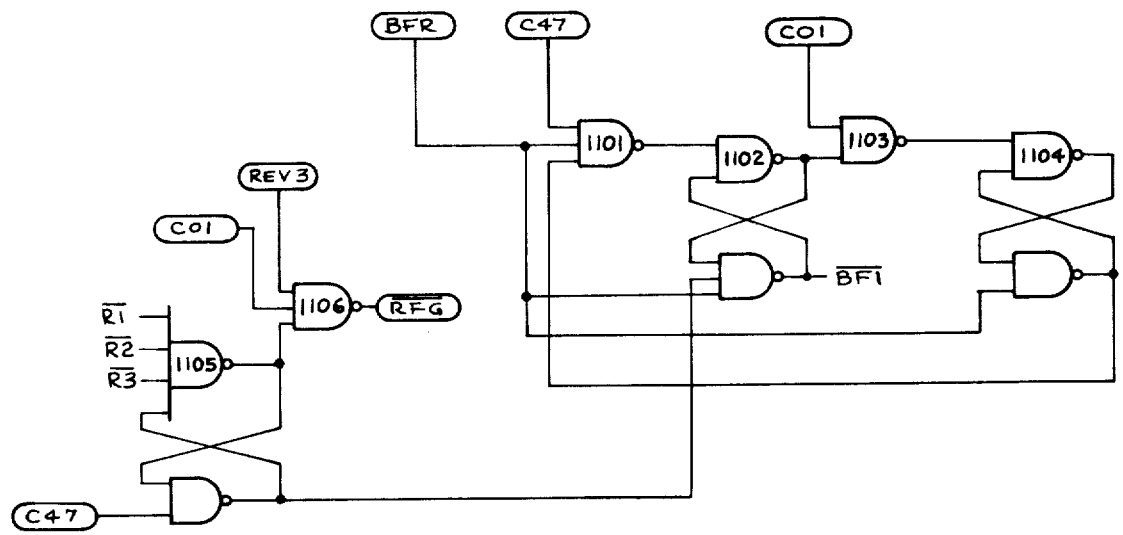
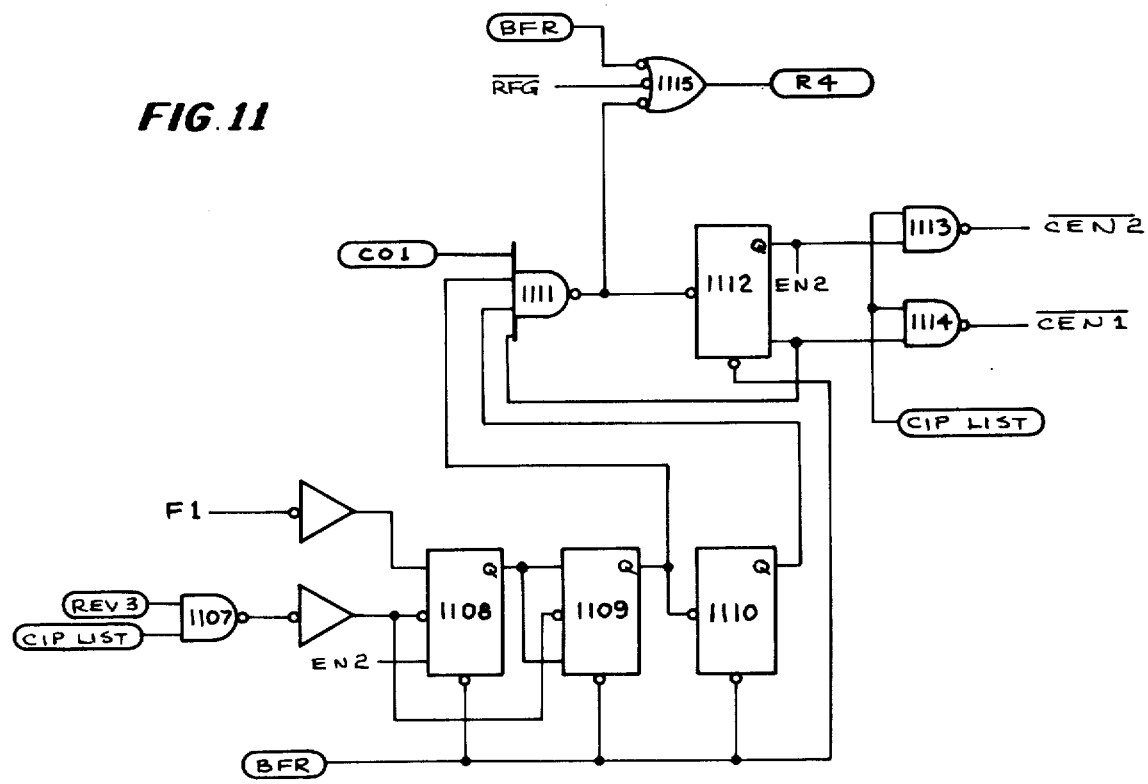
FIG. 11

FIG. 15
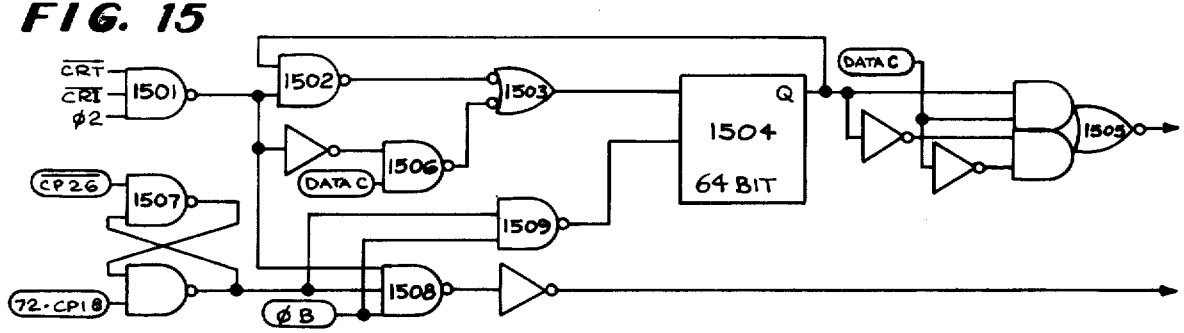
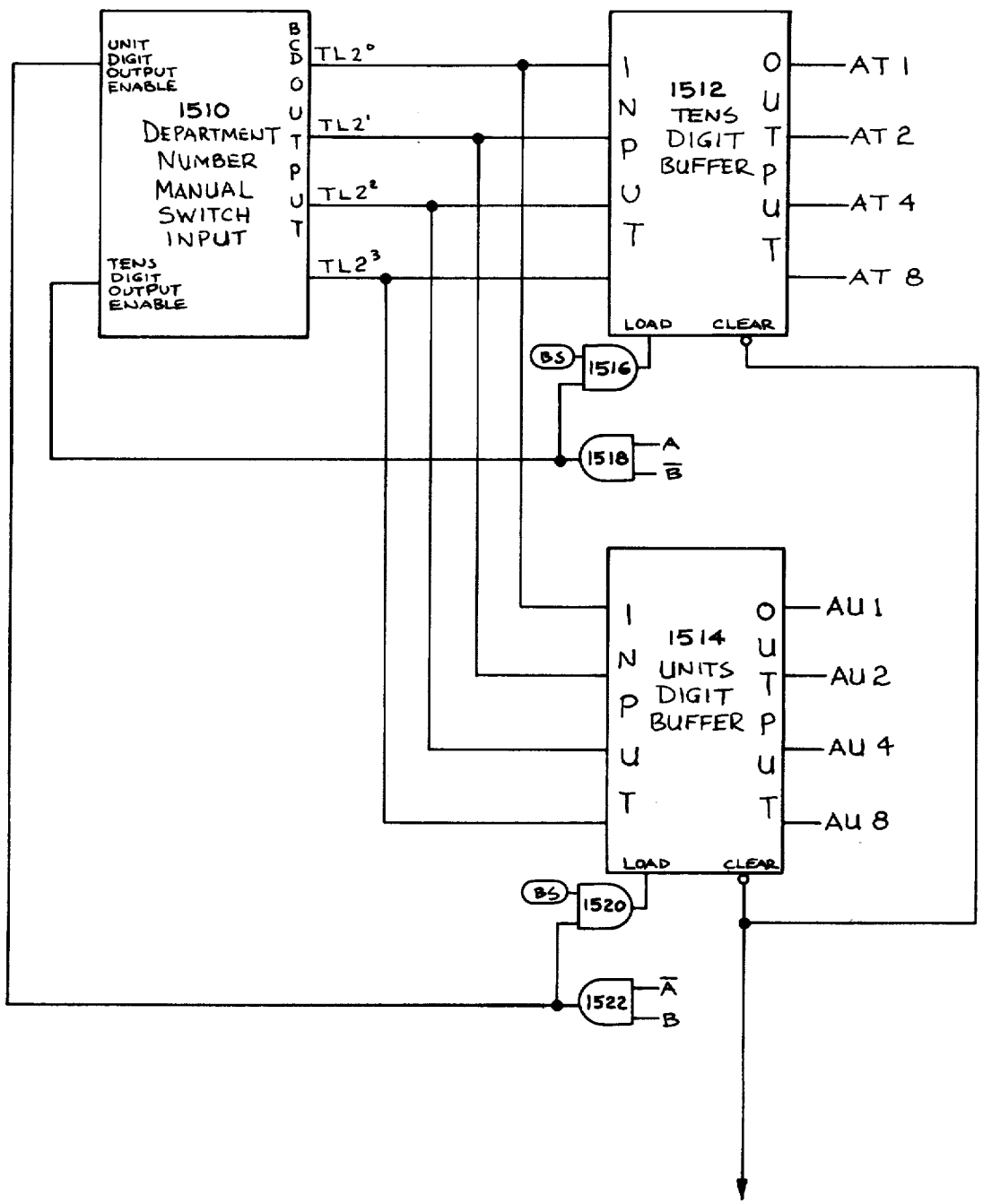

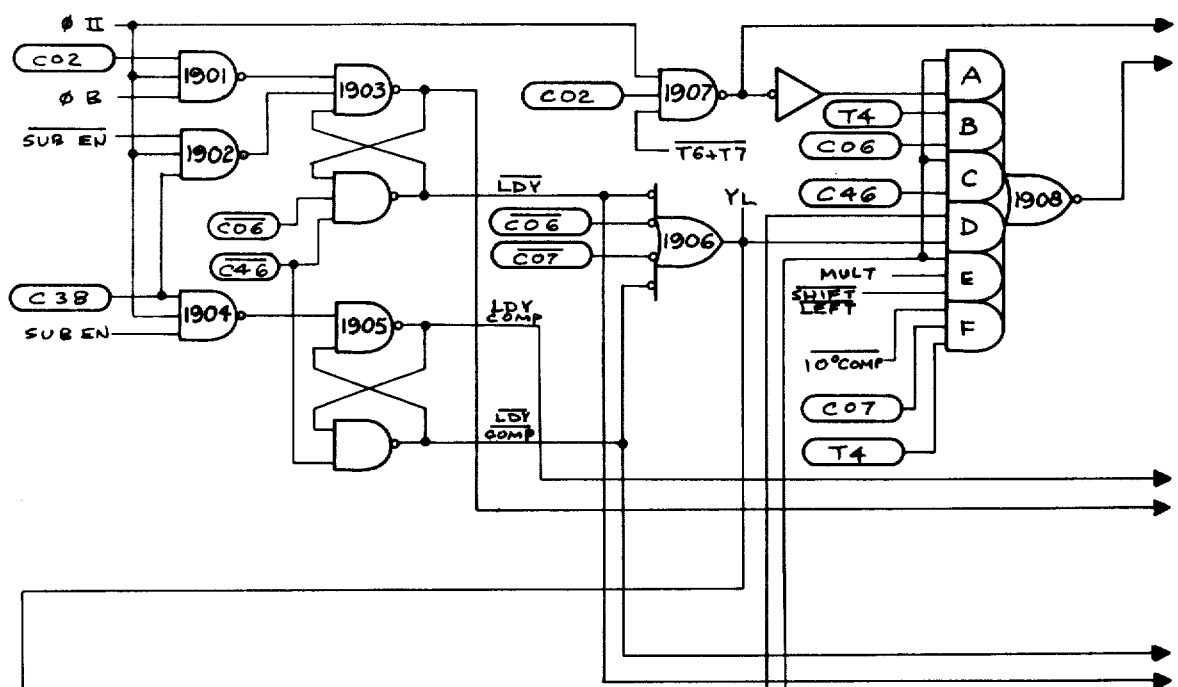
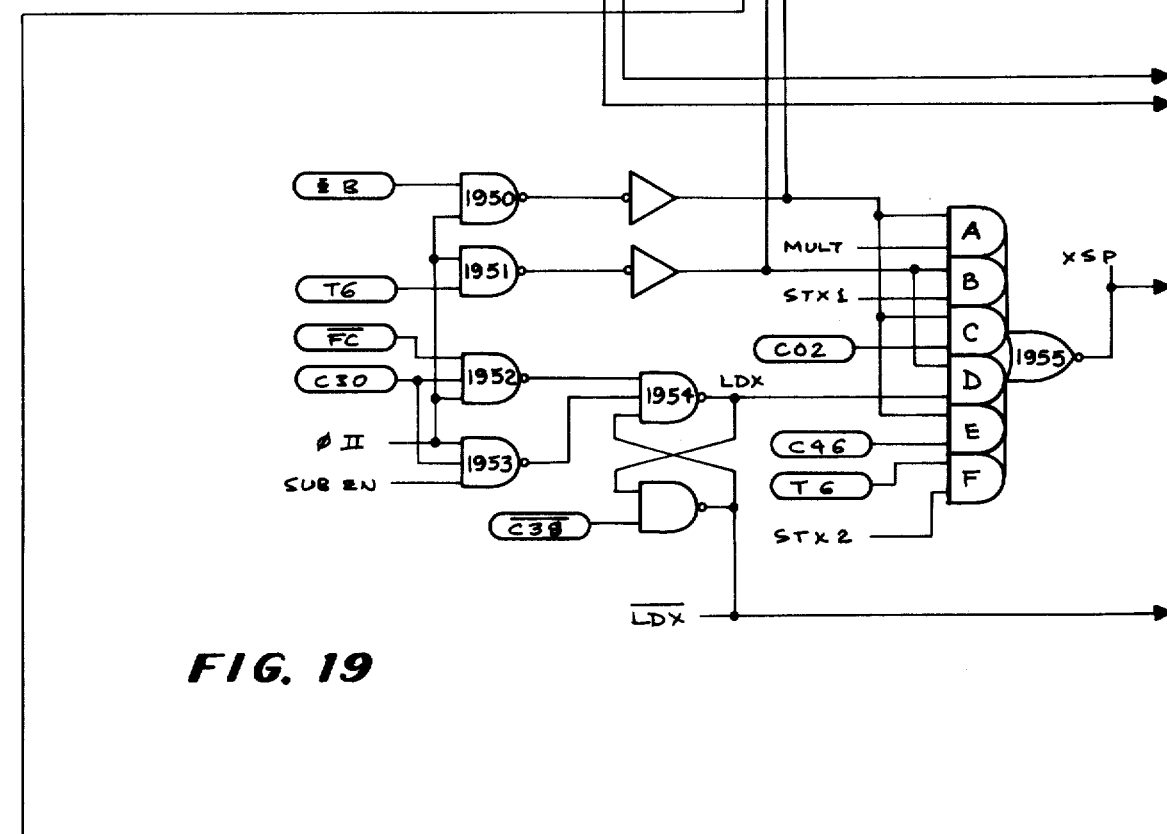
*FIG. 19*

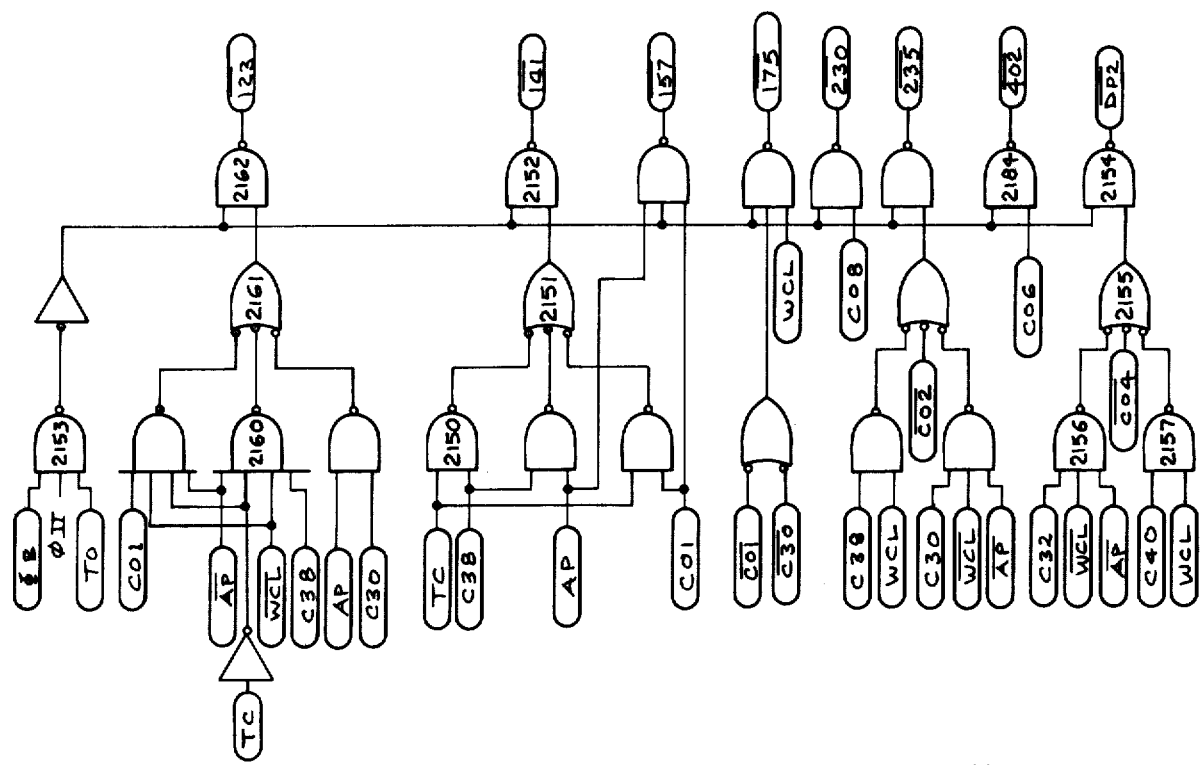
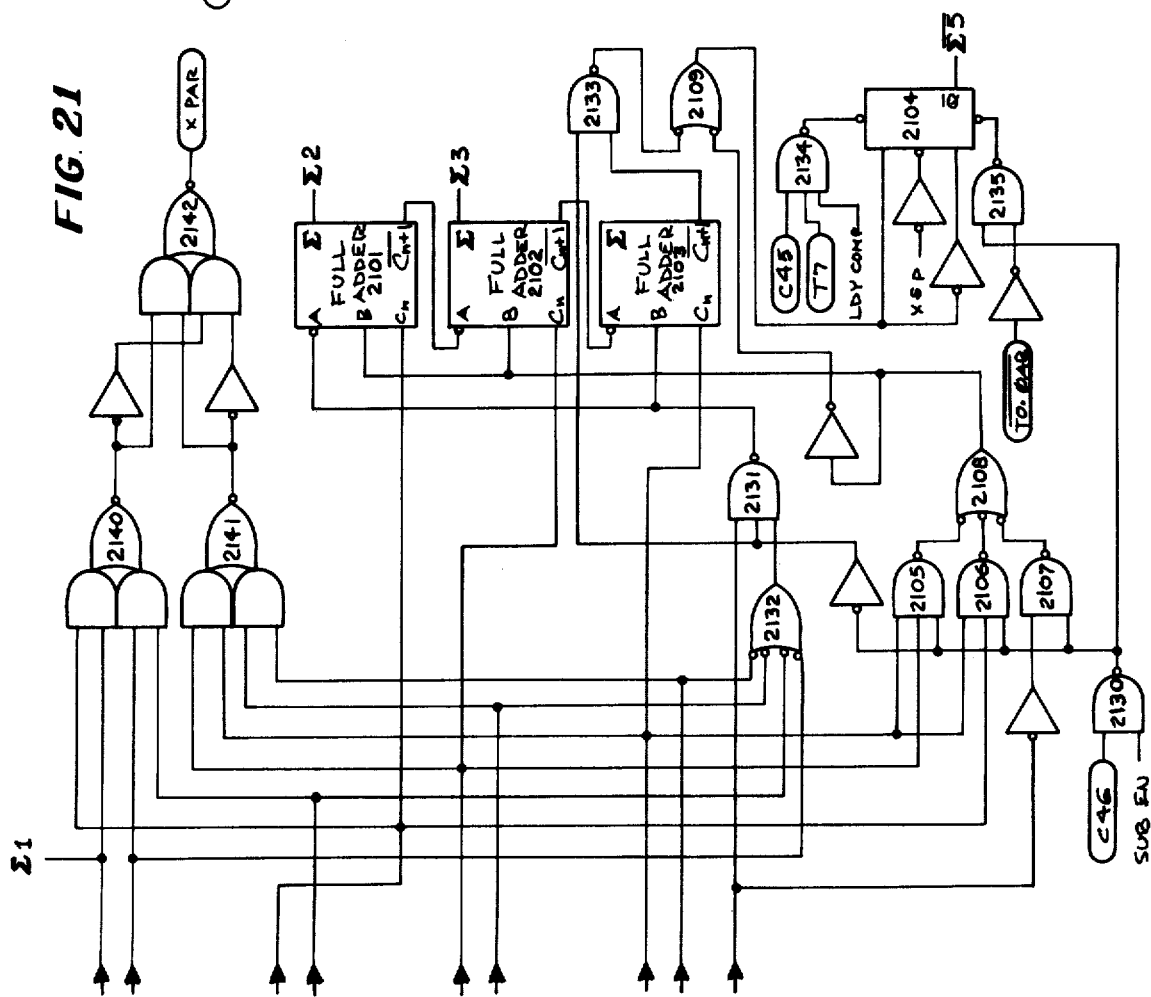
FIG. 21

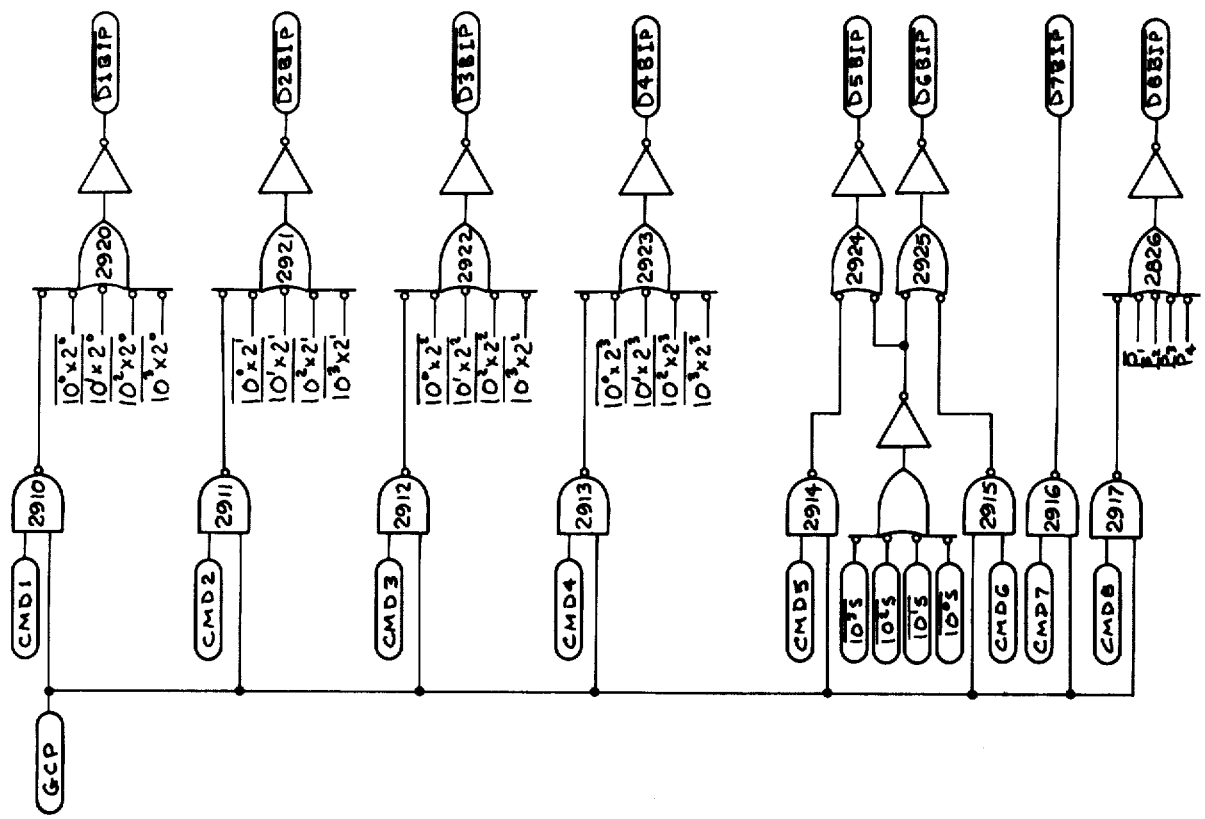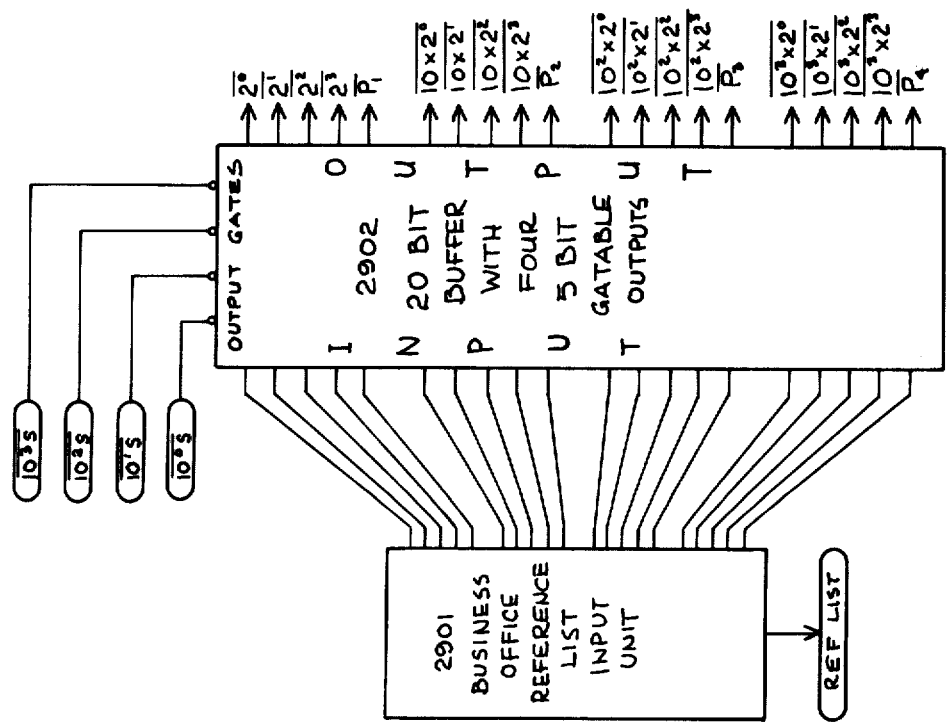
FIG. 29

FIG. 36
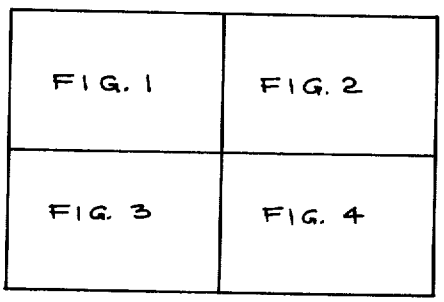
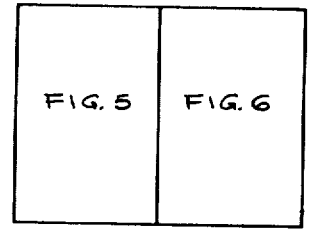
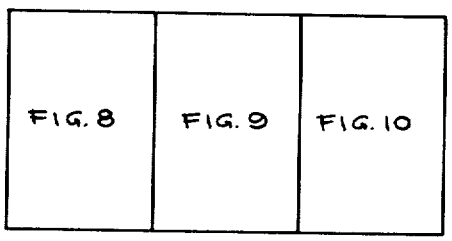
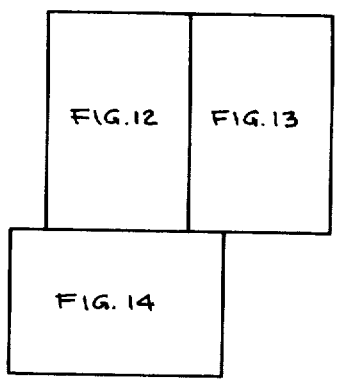
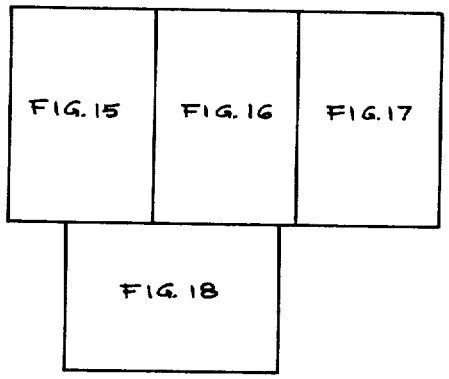
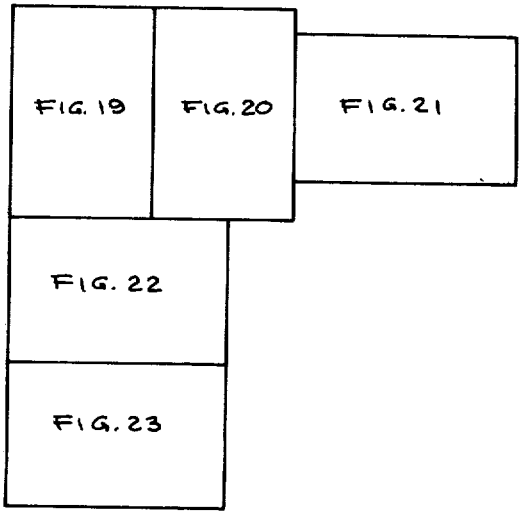
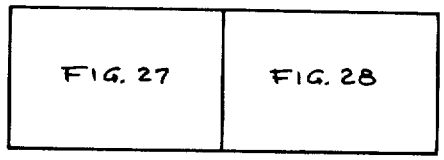
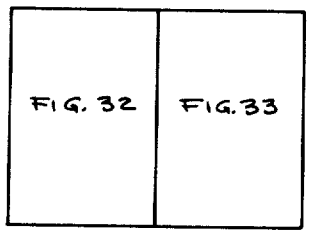
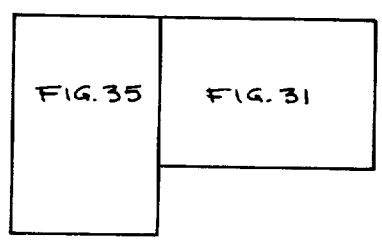

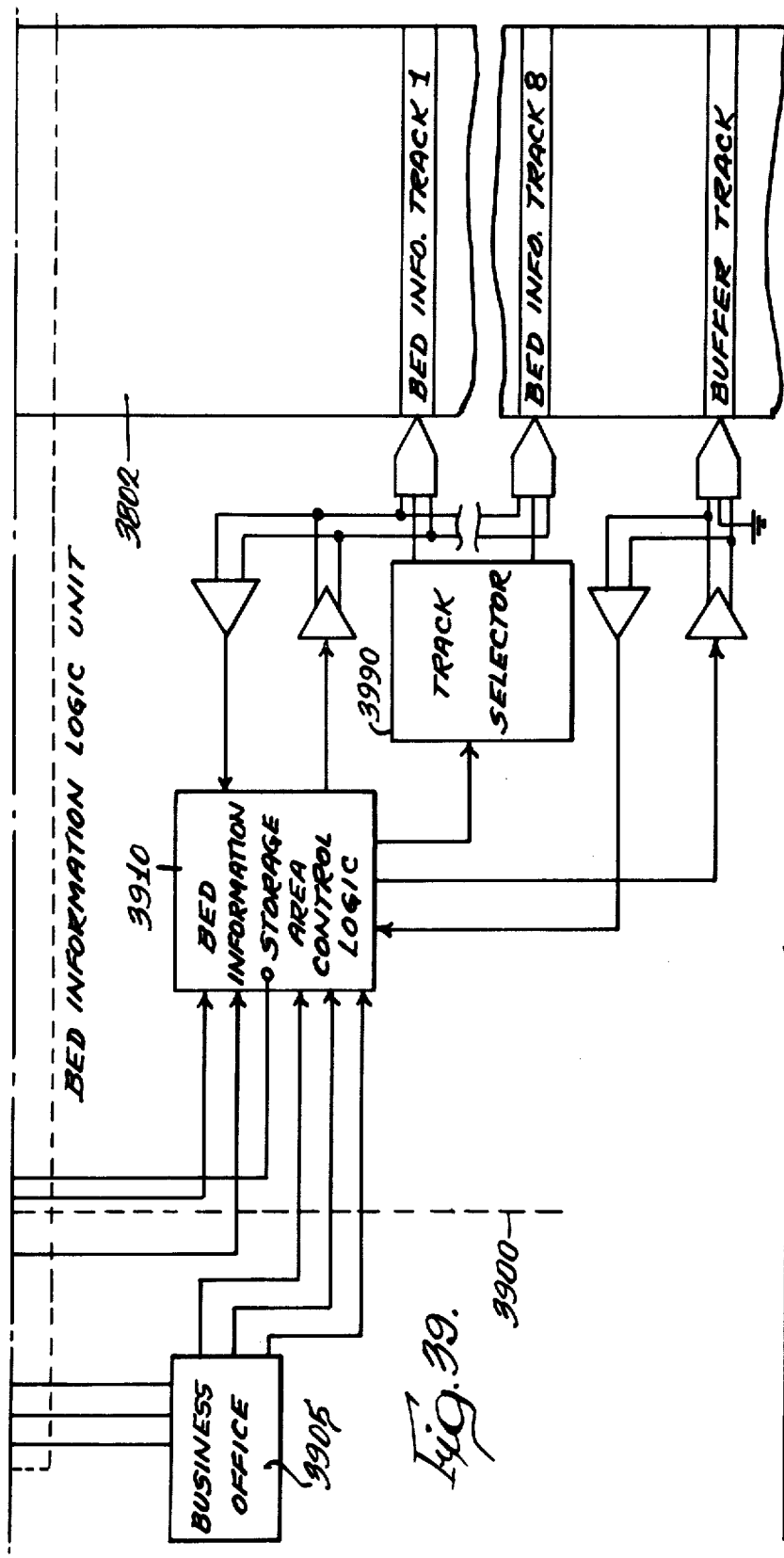
Fig. 39.
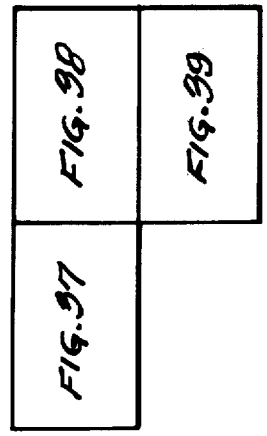

INVENTORY CONTROL, BED ALLOCATION AND ACCOUNTING DATA HANDLING SYSTEM

CROSS-REFERENCE TO RELATED APPLICATION

The present application is a continuation of application Ser. No. 117,839 filed on Feb. 22, 1971, now abandoned. Said application Ser. No. 117,839 is itself a continuation of the application Ser. No. 761,042 filed on Sept. 20, 1968, now abandoned.

The data input and output units used with the system of this invention are disclosed and claimed in a contemporaneously filed application Ser. No. 761,043 filed on Sept. 20, 1968 by Louis E. Philipps and Eugene A. Stanis, now U.S. Pat. No. 3,597,742 which issued on Aug. 3, 1971, and is assigned to the same assignee as the present application. This U.S. Pat. No. 3,597,742 is for all purposes incorporated into the present application.

TABLE OF CONTENTS

Background of the Invention
Summary of the Invention
Brief Description of the Drawings
Description of the Preferred Embodiment
    Summary
    Logic Diagrams and Symbols
    Bed Information Storage Area Control Logic
    Charge Information Storage Logic
    Charge Information Printout Control
        Printout Marker Detector and Buffer Track Control for the Charge Information Storage Area
        List-Output Control
        Bed Information Printout Format Generator
        Charge Information Printout Format Generator
        Tally Search Control Logic
        Patient Charge Search Control Logic
        All Patients Charges Search Control Logic
    Arithmetic Unit

BACKGROUND OF THE INVENTION

This invention relates to a data handling and processing system and, more particularly, to a system for automatically collecting, compiling, and performing arithmetic operations on data such as data relating to hospital operations.

The operation of a hospital with even a small number of beds involves the preparation and transmission of a very large number of rather short messages relating to virtually every phase of hospital operation ranging from pharmacy orders, requests for laboratory tests, and admitting or discharging instructions to requests for repair of a broken window. In some hospitals, a written order is made only when the nature of the service demands it, and other functions such as maintenance or bed status are requested by oral communication. Further, many of the operations or items covered by the messages require a charge to be made frequently against several entities, e.g., inventory and a patient. These charges are collected either by using the primary written message or by making secondary records frequently in machine code based on a primary message.

However, the use of written orders and messages is time consuming, requires manual transmission or conveyance to perhaps a number of points of use, and is subject to error in preparation when read and translated to secondary records. The compilation and calculation of charges or inventory records requires the physical presence of all of the records, and it has been determined that errors arise not only from record loss but from charges entered for services requested that are not actually performed. The time involved in collecting and translating the records and messages frequently causes a delayed billing for charges not available on discharge and delays the submission of charges to other paying bodies such as insurance companies. Further, because of the time required by written messages, there is a temptation to use oral requests when the nature of the requested service or item does not demand a written record.

SUMMARY OF THE INVENTION

The data handling and processing system of the present invention does away with written messages and orders and insures the collection, calculation, and compilation of all charges on any desired periodic basis. Messages and charges are free of transmission errors and provide legible permanent copy for medical records. In addition, skilled hospital personnel are freed from time consuming clerical duties and from acting as messengers with the resultant increase in their availability for professional services.

In general, the system includes a central processing unit which receives data from and supplies data to a plurality of remote stations each located at a point from which messages or orders are normally received and to which this data is normally directed. Each remote station includes a data recorder such as a teleprinter and a data transmitter. The data transmitter comprises a card or record reader which is enabled for operation by the insertion and actuation of a key identifying the station operator such as a technician or nurse and which is adapted to send plural card messages to selected points. Each station includes prepared cards containing all of the message information normally required by the department and other cards individually identifying each patient. By inserting the cards forming a plural card message into the reader, the patient and requested service information is automatically transmitted to one or more points in the hospital as required for each service or message, and any data relating to charges or other data compilations is collected in storage in the central processing unit. During message transmission from the card or record reader, a digital signature identifying the key that enabled the card reader is automatically transmitted to identify the person responsible for originating the message. The system also includes special equipment at such locations as the business office and cashier's office, which include manual data entry means in addition to a card reader. The business office station also possesses controls by which periodic or daily charge totals, credit totals and payment on account totals, and specific or complete listings of patient charges, can be retrieved from the system and the system cleared of all data printed out.

The basic system organization includes a plurality of card readers, groups of which time-share different delay lines providing input buffers. The delay lines are scanned for complete messages to enable transfer of a complete message to a magnetic core storage unit. The data in core storage is then either transferred to a magnetic drum storage unit, or is transmitted to one or more of the remote stations, or both, depending upon the nature of the received information and the functions required to be performed on the data designated by control characters on each card. If the message requires nothing more than transmission to one or a group of stations, the data is transferred from the core storage unit to tracks on the drum which function as an output buffer, and then is delivered over output lines to the addressed stations. If the message relates to items such as chargeable services or reflects changes in the allocation or status of beds, the data from core storage is transferred to a bed information storage area or a charge information storage area on the drum, perhaps after processing in an arithmetic section which has access to the core storage unit.

The bed information storage area includes a storage location for each bed containing information on the patient occupying the bed, and also containing information as to the condition or status of the bed. This information is updated continuously with information transmitted into the system from the remote stations. The system includes bed information search logic for compiling listings of the information stored in this area, such as lists by nursing station of beds which need attention, lists by nursing station of beds which are in a particular status (available, occupied, etc.), lists of patients admitted on a particular day, and the like.

The charge information storage area includes numerous storage locations into each of which a record of a cash or inventory transaction can be placed. A complete record of each individual charge against a patient, payment on account, and withdrawal from or addition to inventory is maintained. The system includes charge information searching logic for compiling listings of the information stored in this area, such as tally lists by department of changes in inventory, listings of charges allocable to a particular patient, and a complete breakdown of all charges by patient number. This latter list is called an all patient charges list, and is usually printed out at the end of the day just prior to the time when the record of that day's transactions is erased to make room for the next day's transactions. The tally inventory lists are by item number. A special tally arithmetic unit calculates the total quantity of each item debited or credited to the inventory of each department, so the tally lists are summarized and are not broken down into individual transactions.

BRIEF DESCRIPTION OF THE DRAWINGS

Many other objects and advantages of the present invention will become apparent in considering the following detailed description in conjunction with the drawings in which:

FIGS. 8-10 form a logic diagram of the bed information printout format generator;

FIG. 11 and FIGS. 12-14 form a logic diagram of the charge information printout format generator;

FIGS. 15-18 form a logic diagram of the tally search control logic;

FIGS. 19-23 and FIG. 24 form a logic diagram of the arithmetic unit;

FIG. 29 is a logic diagram of the business office reference list data input logic;

FIG. 36 is a map indicating how connecting drawings are to be positioned; and

FIGS. 37-39 form a block diagram of the entire system.

A map showing how the interconnecting FIGS. 37-39 are to be placed is included in FIG. 39.

DESCRIPTION OF THE PREFERRED EMBODIMENT

Figure 37:
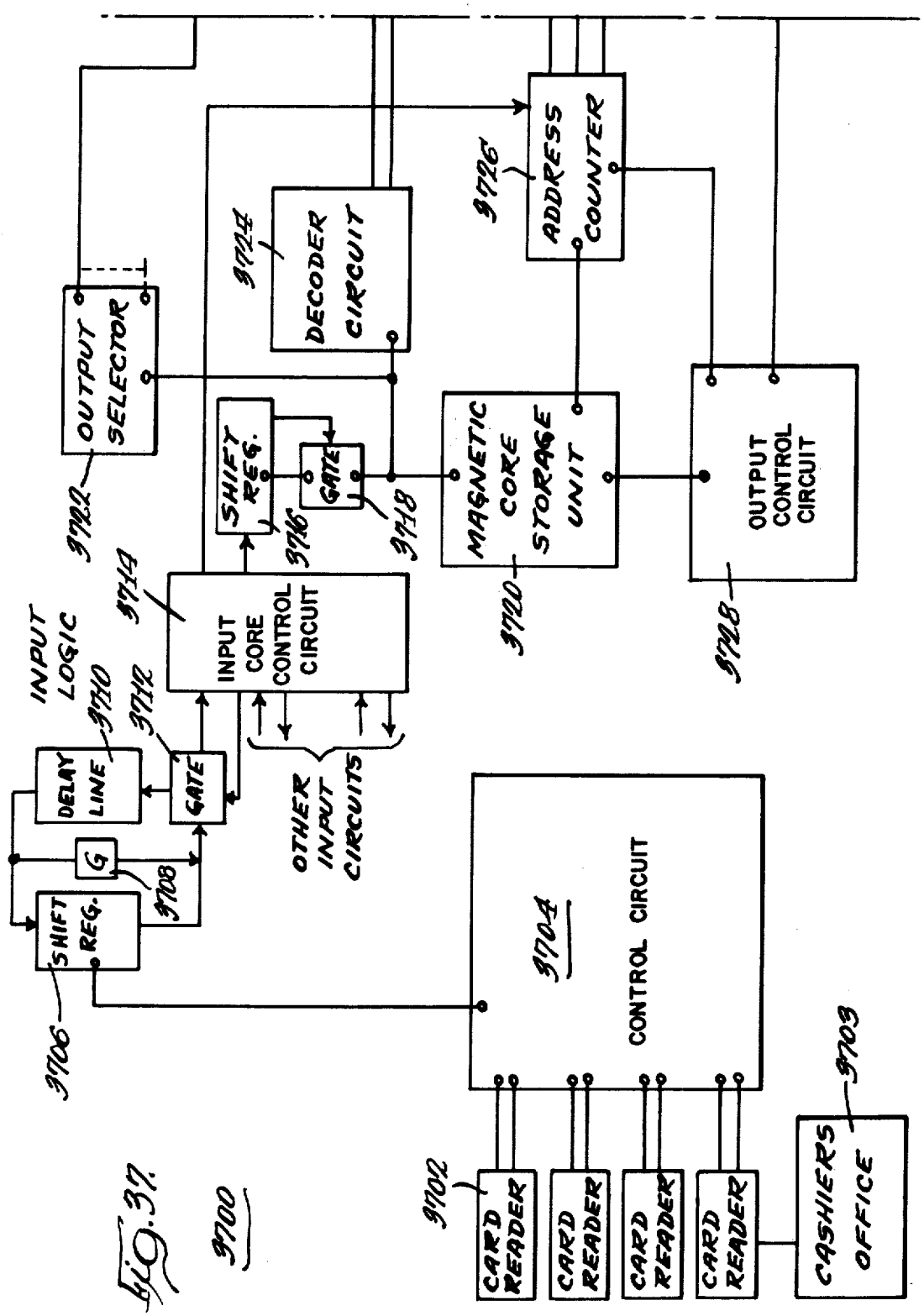
Figure 38:
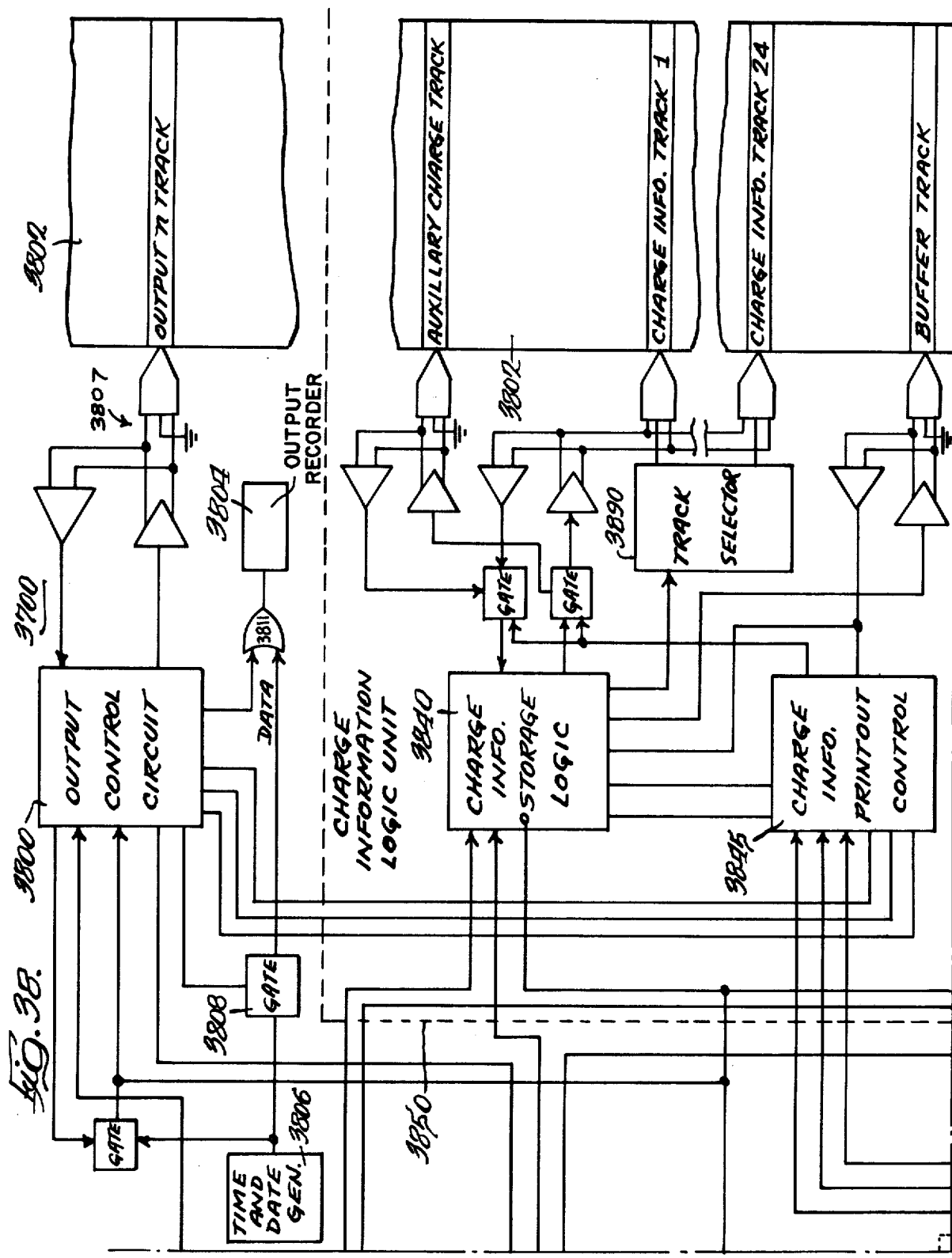

Referring now more specifically to FIGS. 37-39 of the drawings, therein is disclosed a block diagram of a system 3700 embodying the present invention. The system 3700 is capable of transmitting and receiving all of the communications, orders, and requests normally handled in a hospital and of automatically compiling and computing all necessary data relating to patient charges and the status of the beds in the hospital, as well as providing a running inventory control. To insure against the presence of errors, virtually all input messages are made by selecting records in machine readable code from a prepared supply thereof containing all of the messages and service requests normally required in a hospital. The patient information is derived from records prepared in machine readable code on admittance to the hospital.

Normal entry to the system is obtained through a card reader 3702 which is supplied with two or more punch cards or permanent records containing patient identifying information, message information, and one or more control codes. Each of the card readers 3702 is enabled by the actuation of a key individual to the operator or the person responsible for transmitting the message into the system 3700. The actuation of this key appends a plural digit identifying designation to the message transmitted from each record. A group of card readers 3702 share a common delay line 3710 which provides a buffer storage unit to which access is obtained through a control circuit 3704. The delay line 3710 is divided into a number of time slots equal to the number of card readers 3702 having access to the delay line. When message data is to be loaded into the delay line 3710, the control circuit 3704 selects one of the card readers 3702 to which it has access and transfers the information character by character into the delay line 3710.

Message data stored in the delay line 3710 is normally circulated through the shift register 3706 and a gate 3712. However, when new message information is to be added to the delay line 3710, a gate 3708 is enabled to bypass the shift register 3706. This time shifts the message information a single character position and permits the new message material in the shift register 3706 to be added to the delay line 3710.

After a complete message has been stored in one of the time slots in the delay line 3710, the gate 3712 is selectively enabled under the control of an input core control circuit 3714 which is common to a number of delay lines 3710 to transfer a complete message character by character to an input shift register 3716. When a complete message has been transferred from the delay line 3710 to the shift register 3716, it is transferred through a gate 3718 to the input of a magnetic core storage unit or core memory 3720. The control circuit 3714 controls an address register or counter 3726 to place each character from the shift register 3716 in a predetermined address location in the storage unit 3720.

As each message is shifted through the register 3716 into the magnetic core storage unit 3720, an output selector 3722 examines the incoming message for address codes and performs one or a plurality of output selection operations to select one or a group of output controls 3800 each individual to a single output such as a recorder or teleprinter 3804. Each of the output control circuits 3800 has access to a plurality of buffer storage blocks on a track of a magnetic drum 3802 forming a part of a central processor unit consisting essentially of a charge information logic unit 3850 and a bed information logic unit 3900. If at least one of the buffer storage areas on the drum 3802 of an addressed output control circuit is available, the output recorder or teleprinter 3804 is considered idle or not busy, and the magnetic core storage unit 3720 is permitted to receive the entire message, and this message is erased from the delay line 3710. Alternatively, if any one of the output control circuits 3800 selected by the output selector 3722 does not have available buffer storage space, the message is not stored in the unit 3720 because it cannot be immediately processed, and the message is retained in the delay line 3710 without erasure.

The system 3700 also includes a decoder circuit 3724 which also monitors the data supplied by the shift register 3716 to the magnetic core storage unit 3720 in selected locations to detect and decode certain control characters or codes that advise the system 3700 of the nature of the operation to be performed on the incoming message information. The decoder circuit 3724 supplies the decoded information to the charge information logic unit 3850 and the bed information logic unit 3900 to indicate the disposition which is to be made of the message information. If the message information requires processing or relates to the operations performed by the units 3850 and 3900, this information is transferred out of the magnetic core storage unit 3720 and into one of the units 3850 or 3900. Alternatively, if the message indicates that no operations on the data are to be performed, and it is to be supplied to an output recorder 3804, an output control circuit 3728 controls the address register 3726 to select the desired information and transfer this information through the circuit 3728 to the output control circuit 3800 with the timing required to write this information onto the buffer track of the drum 3802 through conventional drum reading and writing electronics indicated generally as 3807. The control circuit 3800 selects an idle buffer block on the track for receiving the message information. Incident to this transfer, the output control circuit 3800 enables a gate 3808 so that date and time information from a date and time generator 3806 can be added to the message. Further, by controlling the addresses primed into the register 3726, the output control circuit 3800 can control the makeup and content of the message placed in storage on the drum. When a complete message has been stored on the drum 3802, the output control circuit 3800 reads the data character by character from the buffer storage block with drum timing and supplies this data through an output gate 3811 with the timing required by the teleprinter 3804 to control the teleprinter to produce an output message.

If the message stored in the core storage unit 3720 includes charge or inventory information, this information is supplied to a charge information storage logic circuit 3840 for storage on the tracks of the drum 3802 assigned to the unit 3850. If the message includes patient or bed information which is to be stored, this information is supplied to a bed information storage area control logic 3910 for storage on the tracks of the drum 3802 assigned to the unit 3900. List requests are processed in the units 3850 and 3900 and transferred by a charge information printout control circuit 3845 to the output control circuit 3800 which is directly addressed by the circuit 3845. List data does not go into the buffer storage associated with the various control circuits 3800, but is directly transferred to the teleprinter 3804. If desirable or necessary, date and time information can be added to the messages supplied by the units 3850 and 3900 under the control of the control circuit 3845.

The data collection and message transmission parts of the system 3700, and also the circuitry controlling the magnetic core storage unit 3720, are shown and described in detail in the Phillips et al. U.S. Pat. No. 3,597,742. The present application describes in detail those parts of the system used in the processing and the storage of data. More particularly, the present application discusses the details of the bed information storage area control logic 3910, the charge information storage control logic 3840, the charge information printout control 3845, and also the details of an arithmetic unit that is not shown in FIGS. 37 to 39. The discussion of the charge information printout control 3845 is broken down into six parts, including separate discussions of the logic used to control individual patient charge searches, all patient charge searches, and tally inventory searches. Unless otherwise specified, the discussions below assume that the procedure of transmitting data from a remote station 3702 into the magnetic core storage unit 3720 has been completed, and that all control characters accompanying the data have been decoded by the decoder circuit 3724 and translated into control signals.

Forty-eight tracks of the drum storage area 3802 are allocated to the storage of charge information, and one track is allocated as a buffer in which charge information which is to be printed out can be temporarily stored before printout. Another auxilliary charge information storage track is used to store charges which are received while the system is organizing and printing out a list of the charges from the previous day. Fifteen tracks are allocated to the storage of bed allocation information, with one track again serving as a buffer track for information which is to be printed out.

Each track within the charge information storage area is divided into 72 individual storage locations. These storage locations each contain thirty-six eight bit characters. Each of the thirty-six characters is assigned a character number between zero and 35. As the drum rotates, a system counter generates timing pulses CP0, CP1, CP2, . . . , and CP35 which indicate the character within the storage location currently being scanned that is below the drum pickup head.

The following is a listing of the information stored within each character location of a typical charge information storage area:

Character 0 — This location is used for storage of a busy or full marker. When charge information is stored within the rest of the area, a mark is placed in CP00.

Characters 1 through 12 — Patient case number. This number and other data pertaining to a charge item are fed into the system along with an R (charge data) control character.

Character 13 — Printout marker for the cashier's office. A mark is placed at the fourth bit position within this location if the information contained in this storage location is to be transmitted to the cashier's office teleprinter.

Characters 14 and 15 — Point of sale number. This number indicates where the transaction took place.

Characters 16 and 17 — Point of revenue number. This number indicates the account which is to be credited for the sale.

Characters 18 through 25 — Item number, indicating the particular item or service which is sold or performed.

Characters 26 and 27 — Quantity of items purchased or ordered. This number is fed into the system on a separate card from that which bears the item number and price, along with an F (multiply) control character.

Characters 28 to 33 — Extended price of the items. This is a unit price as indicated by the input data multiplied by the number of items. The multiplication is performed by the system arithmetic unit in response to an F control character.

Character 34 — Credit symbol. A C can be placed here to indicate that an account is to be credited, or any other symbol can be placed in this location. The credit symbol is fed into the system along with a T control character, usually on a separate input card from the rest of the input data.

Character 35 — Business office printout marker. A mark in the fourth bit of this character indicates that this item is to be transmitted to the business office teleprinter. A mark in the second bit location within this character indicates that this item has already been transmitted to the business office. No mark indicates this item has yet to be considered for printout.

Within the bed information storage area, each track is divided into 54 individual information storage locations. Within each location, some sections contain permanent information. For example, the bed number and the bed price do not change, and are never erased. Other sections are used to store temporary information pertaining to the status of the bed (clean, ready, occupied, etc.) and information as to who is the current occupant of the bed. Individual characters within each location are assigned a number between zero and 47. A system counter generates timing signals C0, C1, C2, . . . , C47 which indicate what character within the storage location currently being scanned is currently below the drum pickup head. The allocation of information within a typical storage location is as follows:

Character 0 — Not used.

Characters 1 and 2 — Nursing station number. Indicates the nursing station within which the bed is located.

Characters 3 to 7 — Bed number. Indicates the individual bed. Usually a three or four digit room number, and a letter indicating the particular bed within the room.

Character 8 — Unused.

Characters 9 to 12 — Bed price.

Character 13 — Unused.

Characters 14 to 17 — Bed status. In this location a three letter code is inserted to indicate whether a bed is occupied (OCP), clean (CLN), ready (RDY) or whatever. The last character in this space is usually left blank, but can be used if desired.

Character 18 — Not used.

Character 19 — Reservation character. A mark is placed here to indicate a bed is reserved.

Character 20 — Not used.

Characters 21 to 32 — Patient case number. This is the number which is assigned to a patient when he first enters the hospital.

Character 33 — Nursing station printout marker. A mark in the fourth bit position within this character indicates that the information stored in this location is to be transmitted to the nursing station whose number is stored in characters 1 and 2.

Character 34 — Sex symbol, M or F.

Character 35 — Admitting office printout marker. A mark in the fourth bit position of this character indicates that the information in this location is to be transmitted to the admitting office.

Characters 36 to 38 — Doctor number. Indicates the doctor that is handling this patient.

Character 39 — Business office printout marker. A mark in the fourth bit position of this character indicates that the information in this location is to be transmitted to the business office teleprinter. A mark in the second bit position indicates that this information has already been transmitted to the business office teleprinter.

Character 40 to 43 — Reference number or date. The reference number is assigned to each patient when he enters the hospital. The business office is able to perform reference list searches for all patients having a particular reference number. Usually this number is the month and day when a patient was admitted to the hospital.

Character 44 — Reference list printout marker. When this particular item is to be printed out as part of a reference list, a marker is placed in the fourth bit position within this location. Reference lists are transmitted to the business office teleprinter. The format of the output data will be different from that of a character 39 marker printout, as will be explained.

Characters 45 to 47 — Unassigned in the present embodiment.

Arithmetic operations are generally performed within an arithmetic unit (not shown in FIGS. 37 to 39). This unit is able to add, subtract, and multiply. It is interconnected with the magnetic core storage unit 3720 so that data can be transferred readily between the storage unit and various arithmetic data registers within the arithmetic unit. The unit is used to calculate extended prices, and to keep a running total of the charges, charge credits, and payments on account for each day's operation.

When charge data pertaining to an item or service is received by the system along with a control R character, it is stored temporarily in the magnetic core storage unit 3720. The control R character then initiates a search of the charge information storage area for a storage location that does not have a mark in character number 0. When such a storage location is found, the charge information is read out of the storage unit 3720 and is transferred into the location.

The system includes a charge information track counter or track selector 3890 that determines which track of the charge information storage area data is currently being fed into. This track counter generates a series of UAP and TAP signals which indicate respectively the units and tens digit of the current track number. For example, UAP 5 and TAP 20 indicates track 25. Usually charge data is fed into a single track until it is completely full, and then the next sequential track is filled. In this manner, information is stored more or less in temporal order (by time of receipt) in the charge information storage area of the drum 3802.

The system also includes a bed information storage area track counter or selector 3990 that generates a series of UA and TA signals which indicate the unit and tens digit of the current track number. When information is not being fed into this area and when a search for data is not in progress, the system continually scans each track within this area looking for printout markers. When a printout marker is found, a printout is automatically initiated. A search for printout markers in the charge information storage area is carried out in a similar manner when the system generates a SCH5 signal.

Patient information accompanied by a control Q or V character can be stored in any particular location within the bed information storage area by specifying the nursing station and bed numbers stored in that location. The system bed information storage area control logic 3910 scans the bed information storage area until the proper bed number and nursing station number is found.

A wide variety of list compilation and information retrieval tasks can be performed by the system. Some of these are initiated by cards fed into the remote input card readers, and some are initiated by pushbuttons located at certain specified locations.

Three pushbutton lists searches can be initiated by the business office 3905. The first is a reference list search. This is a search through the bed information storage area for all locations containing a specified reference number or date. A small panel in the business office contains a set of four dials and a pushbutton. When the dials are set to a given number and the pushbutton is depressed, this search is automatically performed. The resulting list is printed out in the business office.

A second pushbutton search which can be initiated by the business office 3905 is a tally search. A department number is fed to the system by setting two dials, and a tally pushbutton is depressed. The system tally logic then commences a search of the charge information storage area for all locations containing that department number. When a location containing the specified department number is found, the tally search marks the location for printout, records the item number in a register, and goes through the remaining charge storage area searching out all other locations containing the same department number and item number. A special arithmetic unit within the tally search control logic keeps a running total of the number of such items specified in each location. When a printout of the item number is initiated, the tally logic inserts the total number of items found. This total is then used for inventory control and accounting purposes. The total number of items disbursed is calculated first and then the total credits for items returned is calculated separately. After the tally printout for one item is complete, the tally search resumes and looks for other items having the same department number. The result of the tally search is a complete inventory of the days sales and returns for the department.

The final search which can be performed by push button from the business office is the APC, or all patient's charges search. This search is performed once a day, usually late at night. The first items printed out during this search are the day's total charges, credits, net (charges less credits), and payments on account. This information is retrieved from the core memory. A search is then made through the bed information storage area for individual patient case numbers. Each time a new patient case number is found, all charges relating to that particular patient are retrieved from the charge information storage area and are printed out along with the patient number. When all charges for patients assigned a bed have been listed, the system searches through the charge storage area and prints out the day's charges for out patients and for out house patients. Such patients are assigned a special nursing station number that can be detected by the system logic circuitry. Again, an individual printout is made of the charges relating to each patient. When this has been completed, a final search is made for all charges not previously retrieved. For example, if a patient leaves the hospital during the day, he will not have a bed number that night, and he will not be an out patient or an out-house patient, but his charges will be present within the system.

Three different searches can be requested by card from the remote input locations. These three searches are called the U1 search, the U2 search, and the U3 search.

A U1 search includes all beds belonging to a specified nursing station which require service. The printout includes bed numbers and status characters. A U2 search is initiated by the cashier's office. It searches through the charge information storage area and finds all charges for the day relating to a particular patient. A complete listing of these charges is printed out at the cashier's office, thus enabling an updated bill to be handed to the patient when he leaves the hospital. A U3 search is initiated by the admitting office for all beds within a nursing station whose storage locations contain a specified set of status characters. As noted above, the status characters indicate whether a bed is clean, occupied, etc. This list aids the admitting office in assigning new patients to beds.

The use of printout markers allows data to be read into and out of the drum memory simultaneously. Rather than feeding information directly from the drum to a teleprinter as soon as the information is found within the drum memory, thereby detaining the drum memory for the entire time it takes to transfer information to the low speed teleprinter, a printout marker is placed within the location containing the information. At a later time, a separate search of the drum is made for printout markers. When a marker is found in a track, that entire track is re-recorded on a buffer track and is held on the buffer track while data is transmitted to a teleprinter unit. In the meantime, the main drum tracks are free to receive more input data and more printout markers. Thus, the slow speed teleprinter outputting does not tie up the system input logic. The particular character in which the printout marker is placed indicates where the information is to be transmitted to, so no separate record need be maintained of the destination to which the information is to be transmitted.

Printout formats are determined by separate bed and charge storage area printout format generators. Different formats are used depending upon where the information is to go and what it is to be used for. Most printouts include only a portion of the information stored in a given location. The format of the printout is usually determined by the location of the printout marker.

The day's total charges (etc.) information is read directly from the core memory 3720. A small section of core is allotted for the storage of this information. That section of core not only includes numerical data, but also includes the letter codes which accompany the totals printout. The core storage area running from octal 110 to octal 177 is used for this purpose. The numbers representing the day's total charges, the day's total credits, the net total, and the day's total payments on account are respectively stored in core locations octal 114 to 123, 132 to 141, 150 to 157, and 160 to 175. All other areas within this section of the core are used for line feed and carriage return characters, and also for indications of what the numbers mean. For example, the core locations octal 110 through 112 contain the letters "CHG" to identify the charge total. The data stored in this section of core is read out as a unit at the start of each APC list, as mentioned above.

When the all patient charges or APC search is requested by the business office 3905, the charge section of the drum memory is temporarily tied up for a period of possibly 20 minutes or more. During this period it is necessary to provide an alternate space within which new charges allocable to the next day's operation can be stored. Such new charges are stored in a special track within charge storage area called the auxiliary track. When the APC list is done, the contents of this track are erased and the information temporarily stored in this track is transferred to the first track within the main charge information storage area. In this way there is never any interruption in the collection of charges from the remote system inputs.

When the APC list has been printed out, an erase circuit enables an operator having a special key to erase the contents of the charge information storage area.

In addition to the timing signals mentioned above, a number of other timing signals are commonly referred to throughout this specification. The particular bit within a character that is below the drum pickup head is indicated by a series of T timing pulses, T0, T1, ..., T7. Since one bit of time is lost in the recording process, information must be recorded upon the drum one T pulse early. Thus, a marker which is to be placed in a fourth bit location must be recorded during a T3 timing interval.

PHASE A and PHASE B timing pulses occur during each T timing pulse. The exact timing of these pulses is indicated in the timing diagram included in the concurrently filed application.

One MS (master strobe) pulse occurs at the end of each drum revolution. An HD (head delay) timing interval follows the MS pulse, giving the drum read amplifiers time to stabilize. Eight BS (block strobe) pulses are generated during each drum revolution. The location address counters, the character counters, and the T timing pulse counter all begin to count at the end of the HD interval. A BT (beginning of track) signal is generated just before the end of the HD interval.

An ETC1 pulse occurs while the last location in a charge information track is being scanned. An ETC2 pulse occurs during the character timing interval CP12 within the ETC1 pulse. An ETC3 signal occurs simultaneously with the ETC1 signal as the end of the last track in the charge information storage area is scanned. A TR00 signal is generated before the first bed information storage location is scanned, and an LT (last track) signal is generated when the last bed information storage track is scanned.

Each three successive drum revolutions are differentiated from one another by timing signals called REV1, REV2, and REV3 which occur sequentially and which commence and terminate synchronously with the MS pulses.

Only one teleprinter character can be generated in the time it takes the drum to make three revolutions. During revolutions REV1 and REV2, teleprinter timing pulses TT0, TT1, ..., TT7 are generated. A TT8 teleprinter pulse is also generated, but it is not used in this part of the system. The TT8 pulse would carry a parity bit to the remote teleprinters if they were able to check parity. During REV3, a new teleprinter character is retrieved from drum storage, from core, or from the tally search control logic. This new character is transmitted to the teleprinter 3804 during the REV1 and REV2 timing intervals which follow.

Other timing signals, and also signals generated by circuitry disclosed in the concurrently filed application, will occasionally be referred to as the discussion progresses.

This specification begins with an explanation of the logic diagrams and symbols. This is followed by a description of the bed information storage area control logic 3910. The charge information storage logic 3840 is described next. The description of the charge information printout control 3845 follows, and is broken into seven parts. The first part describes the printout marker detector and buffer track control logic for the charge information storage area. The second part describes the list output control which transfers list data to the various output control circuits 3800 and remote teleprinters 3804. The third and fourth parts describe the bed information and charge information printout format generators. The fifth, sixth, and seventh parts describe the tally search control logic patient charge search control logic, and the all patient charges search control logic. The final section of this specification is a detailed description of the system arithmetic unit.

LOGIC DIAGRAMS AND SYMBOLS

In accordance with the preferred practice of electronic circuit designers, the details of the system 100 are represented by logic diagrams rather than by circuit diagrams. In physically constructing the system 100, each logic element shown is replaced by an equivalent electrical circuit that performs the logical task defined by the logic element. The use of logic elements emphasizes that any of the many differing electrical circuits capable of performing a given logical task may be used interchangeably in the present invention.

To facilitate locating the various elements used in the system, the hundreds or thousands and hundreds digit of each reference number assigned to each element designates the figure of the drawing on which the element is located or was first identified. As an example, a gate 2910 appears in FIG. 29.

Figure 30:
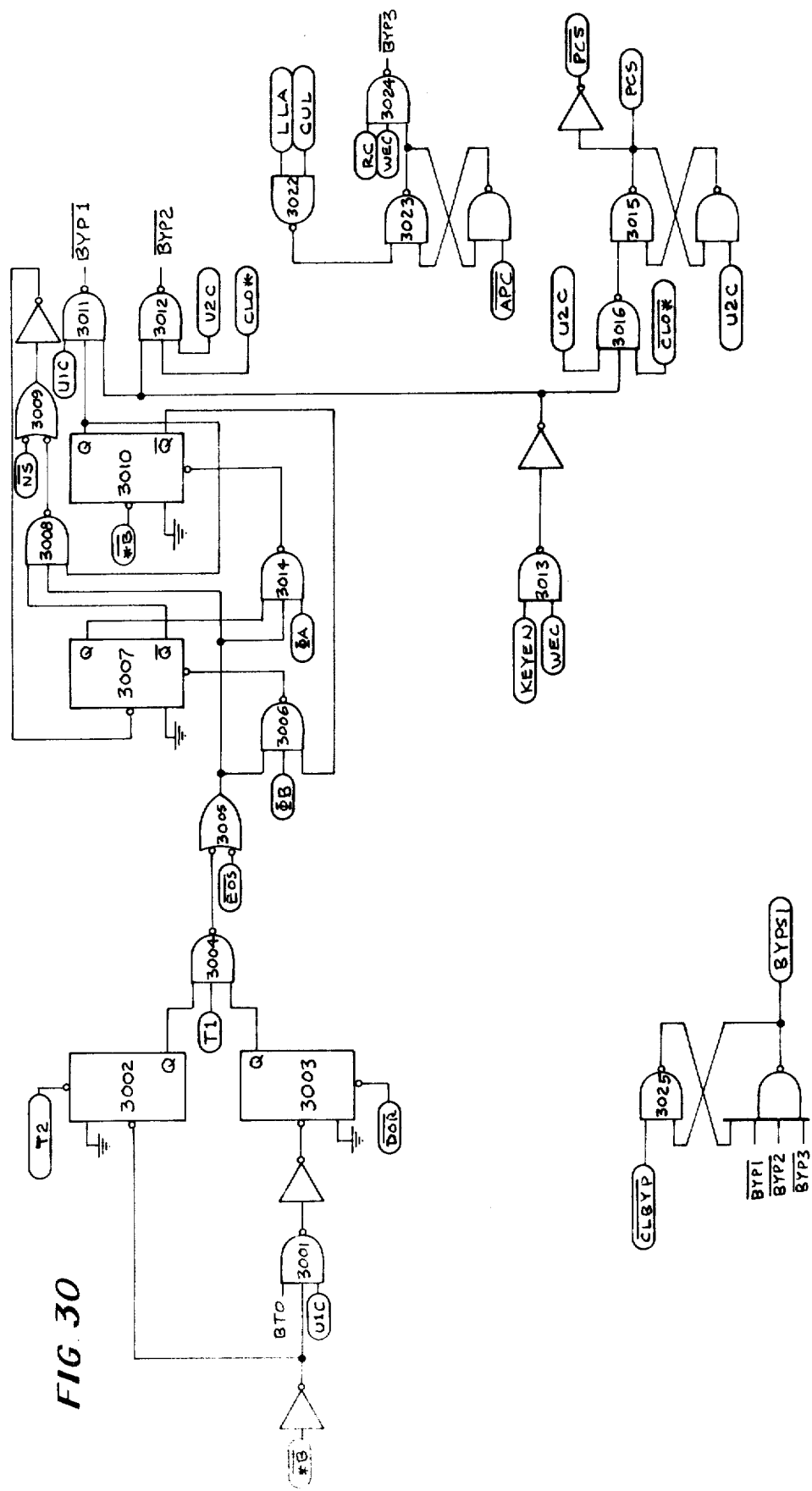
FIG. 30 is a logic diagram of the circuitry which generates the BYPSI signal.

In the system 3700, a high level or more positive potential normally represents a "1", "TRUE", or "PRESENT" signal, and a low level or more negative potential normally represents a "0", "FALSE", or "ABSENT" signal. Throughout this specification, the names of signals are written entirely in capitals. As an example, a patient charge search signal generated in FIG. 30 is designated as "PCS". Signals are often encountered in an inverted form. This is indicated in the drawings by an overline or bar drawn over the signal name. As an example, an inverted bypass 1 signal "BYP1" appears in FIG. 30 as "$\overline{BYP1}$". In this specification, inversion is sometimes indicated by placing the word "inverted" before the name of the signal. More usually, inversions are not mentioned in the specification, since they are clearly indicated in the figures. In this case of an inverted signal, a low level potential represents a "1", "TRUE", or "PRESENT" signal, and a high level potential represents a "0", "FALSE", or "ABSENT" signal.

The preferred embodiment of the system 3700 is constructed almost entirely from transistor-transistor integrated circuit logic elements manufactured by Texas Instruments Incorporated, of Houston, Texas. The fundamental element in the transistor-transistor logic system is the NAND gate, such as a NAND gate 3016 shown in FIG. 30. The NAND gate 3018 has three inputs into and a single output from the D-shaped figure which is used as the standard logic symbol for a NAND gate in this description. The circle separating the D-shaped figure from the output lead signifies an inversion of the output signal. The output lead from this unit is high or at a more positive potential at all times except when all of the inputs are at a high or more positive potential, at which time the output drops to a low or more negative potential.

Inverting gates or NOT gates are represented by a triangular amplifier symbol with a circle at the input or output lead to indicate inversion. These are conveniently formed from NAND gates having their inputs wired together in parallel. Invertors are never mentioned in this specification, since they do nothing more than invert the signals which pass through them.

Figure 31:
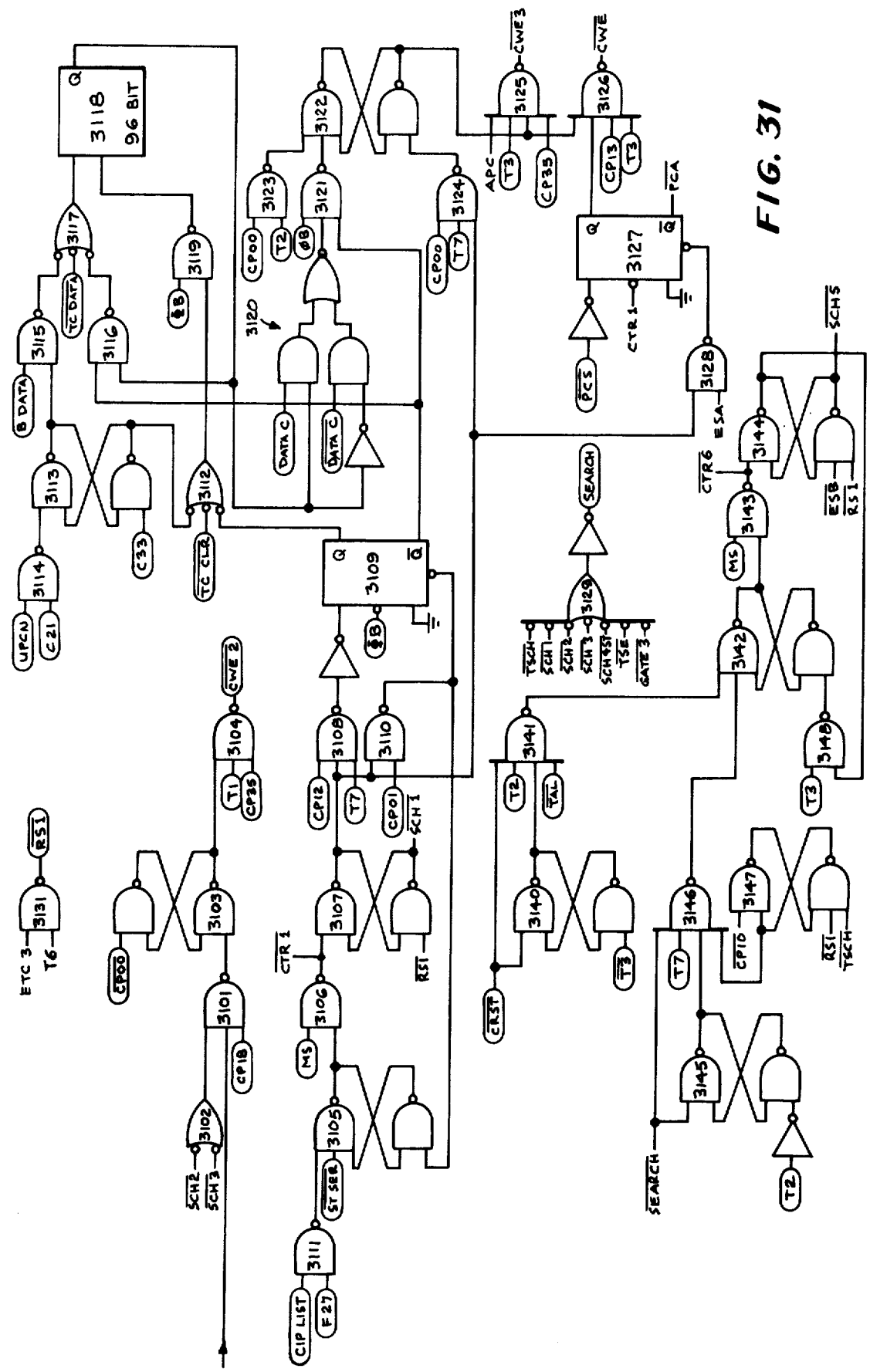
FIGS. 31-35 form a logic diagram of the all patient charges search control logic.

A typical AND-NOR device or comparison gate 3120 is shown in FIG. 31. This device includes a series of two input AND gates, the outputs of which are fed into a NOR gate. The output of this device is normally high or positive. The output goes to a low level whenever both of the inputs to any one of the AND gates are at a high level.

A typical NOR gate 3102 is shown in FIG. 31. The output of the NOR gate 3102 is low or negative if and only if both of the input leads are at a high or more positive potential. If either of the input leads is at a low level, the output rises to a high level potential. Electrically and physically, the NOR gates and NAND gates are identical to one another. Logically, they differ in that NOR gates are used to NOR inverted signals together, while NAND gates are used to NAND non-inverted signals together. In this specification both NOR and NAND gates are referred to simply as gates.

Circles at gate inputs or outputs indicate inversion. Occasionally circles will be shown in the place of inverting amplifiers.

Three types of flip-flops are used in the system 3700. The first type, called a bistable, is constructed by cross-connecting the outputs of two NAND gates with one input of each of the gates. A typical example is the bistable 3103 in FIG. 31.

Figure 32:
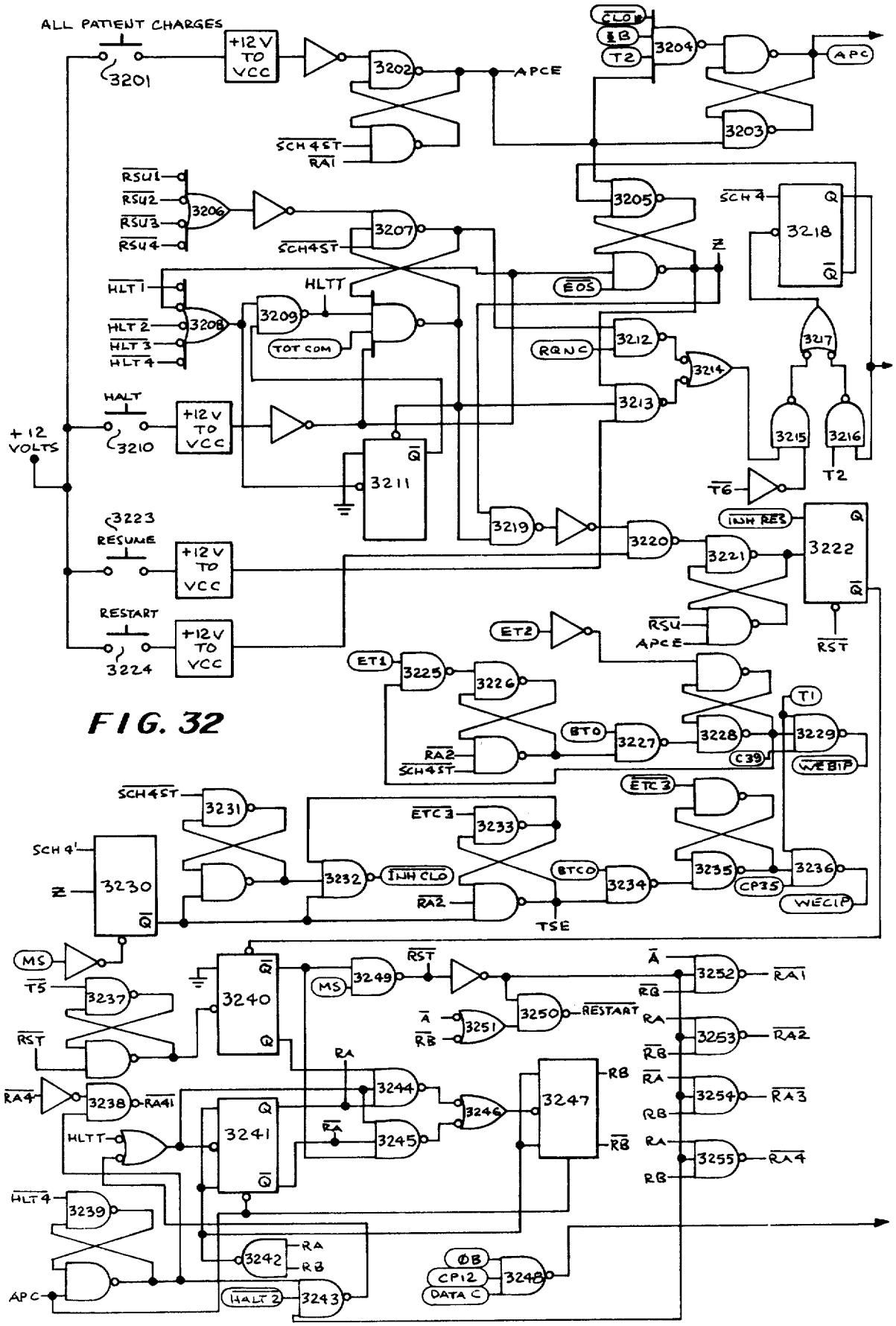
Figure 33:
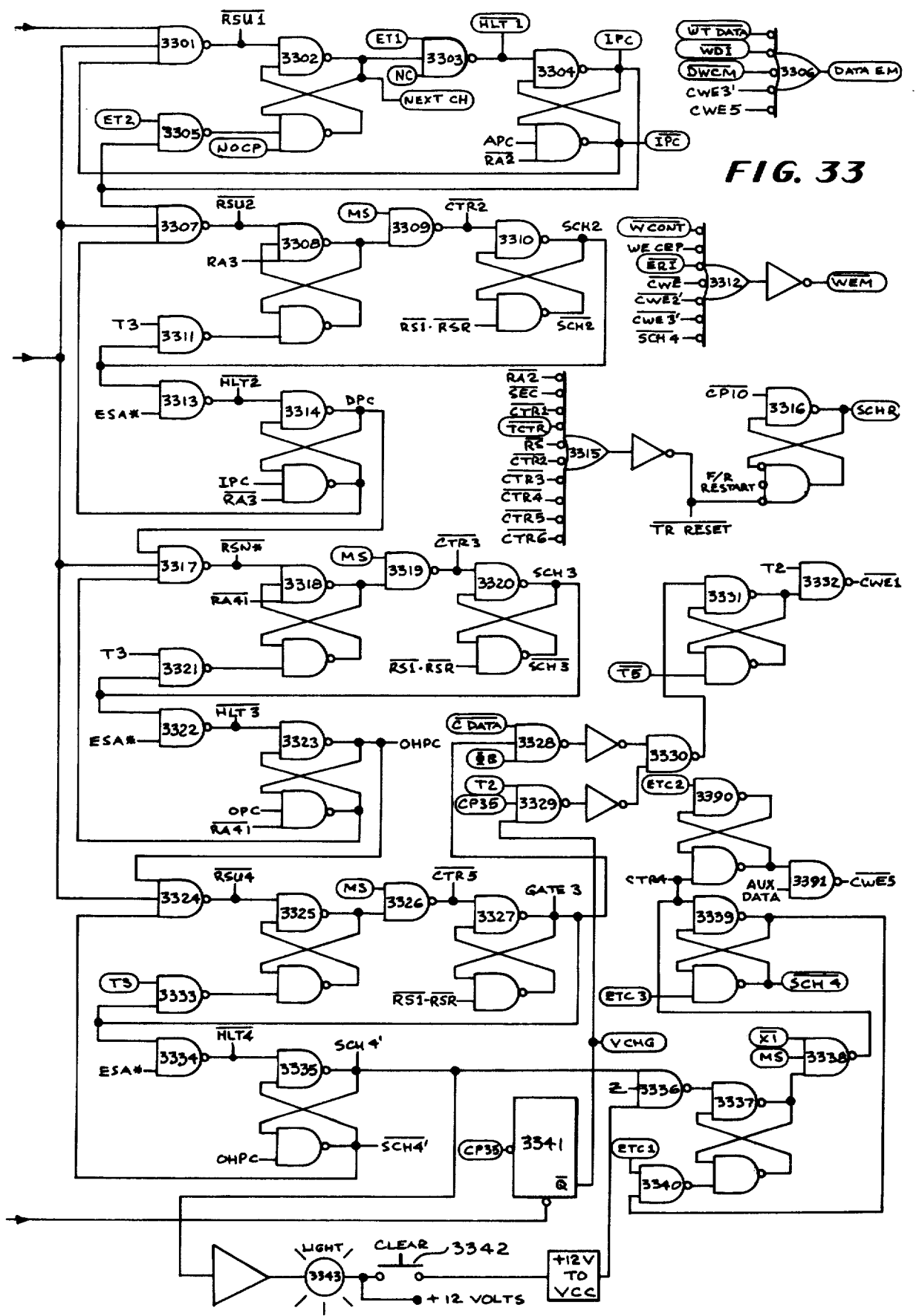

A second type is a standard JK flip-flop, such as a flip-flop 3241 shown in FIG. 32. JK flip-flops can have up to seven input leads or terminals. Of these, only the Q and $\overline{Q}$ terminals are labelled in the figures. J and K input leads, when present, are respectively located directly across from the Q and $\overline{Q}$ output leads. The T input lead is centrally located across from the Q and $\overline{Q}$ input leads, and is separated from the flip-flop by a circle which indicates inversion. S (set) and C (clear) input leads enter the flip-flop adjacent the Q and $\overline{Q}$ output leads, again through an inverting circle. Most JK flip-flops include only a C input lead and no S input lead.

When the clock or toggle input (T) of a JK flip-flop is at a high potential, data applied to the enabling (J and K) input terminals is stored. When the clock input T goes negative, this data is transferred to the Q and $\overline{Q}$ outputs and becomes the flip-flop output. When both of the enabling input terminals are either open circuited or connected to a high level signal, a JK flip-flop toggles or reverses the state of the Q and $\overline{Q}$ terminals whenever the clock input goes from positive to negative. If both of the enabling input terminals are connected to a low level potential, a JK flip-flop remains in its prior state when the clock input goes negative, and does not toggle. When a set or clear terminal is included in a flip-flop, the flip-flop may be set or cleared directly to a desired state. A flip-flop is cleared by applying a low level signal to the clear input terminal to cause a more positive potential to appear at the $\overline{Q}$ output and a low level signal to appear at the Q output. A flip-flop is set or primed by applying a low level signal to the set input terminal to cause a high level signal to appear at the Q terminal and a low level signal to appear at the $\overline{Q}$ terminal.

A third type of flip-flop is the type D flip-flop, for example the flip-flop 3222 shown in FIG. 32. Type D flip-flops have no inverting circle separating the clock or toggle input from the flip-flop body, and no enabling input opposite the $\overline{Q}$ output terminal. The enabling input opposite the Q output terminal is called the D input. When the clock input goes high, it forces the Q output signal to match the D input signal.

Shift registers, such as the shift register 3118 shown in FIG. 31, are assumed to be chains of type D flip-flops having their Q output leads and their D input leads serially connected, and having their clock or toggle leads connected in parallel. The bit capacity of each shift register is always indicated and is equal to the number of flip-flops included within the register.

Full adder circuits, such as the typical full adder 1706 (FIG. 17), always have three input leads on the left hand edge, a sum output lead indicated by the greek letter sigma, and an inverted carry output terminal indicated by the label $\overline{C_n+1}$. Occasionally an inverted sum output lead is also included, and is indicated by an overlined letter sigma. Inverted inputs to full adders are indicated by circles which separate the input lead from the adder. The sum output of a full adder is positive if one or three inputs are positive. The inverted carry output of a full adder is negative if two or three inputs are positive.

The internal circuitry of the individual logic elements is not revelant to the present invention and is therefore not disclosed in the present application. Chapter 11 of the book *Integrated Circuit Engineering-Basic Technology*, Fourth Edition, by the staff of Integrated Circuit Engineering Corporation, Glen R. Mudland et al., published in 1966 by Boston Technical Publisher Incorporated, Cambridge, Massachusetts, gives a rather complete explanation of digital integrated circuits suitable for use in the system 3700. Additional background on the use of logic diagrams and integrated circuits can be found on pages 149 through 162 of ELECTRONICS, Vol. 40, No. 5, Mar. 6, 1967.

BED INFORMATION STORAGE AREA CONTROL LOGIC

Figure 1:
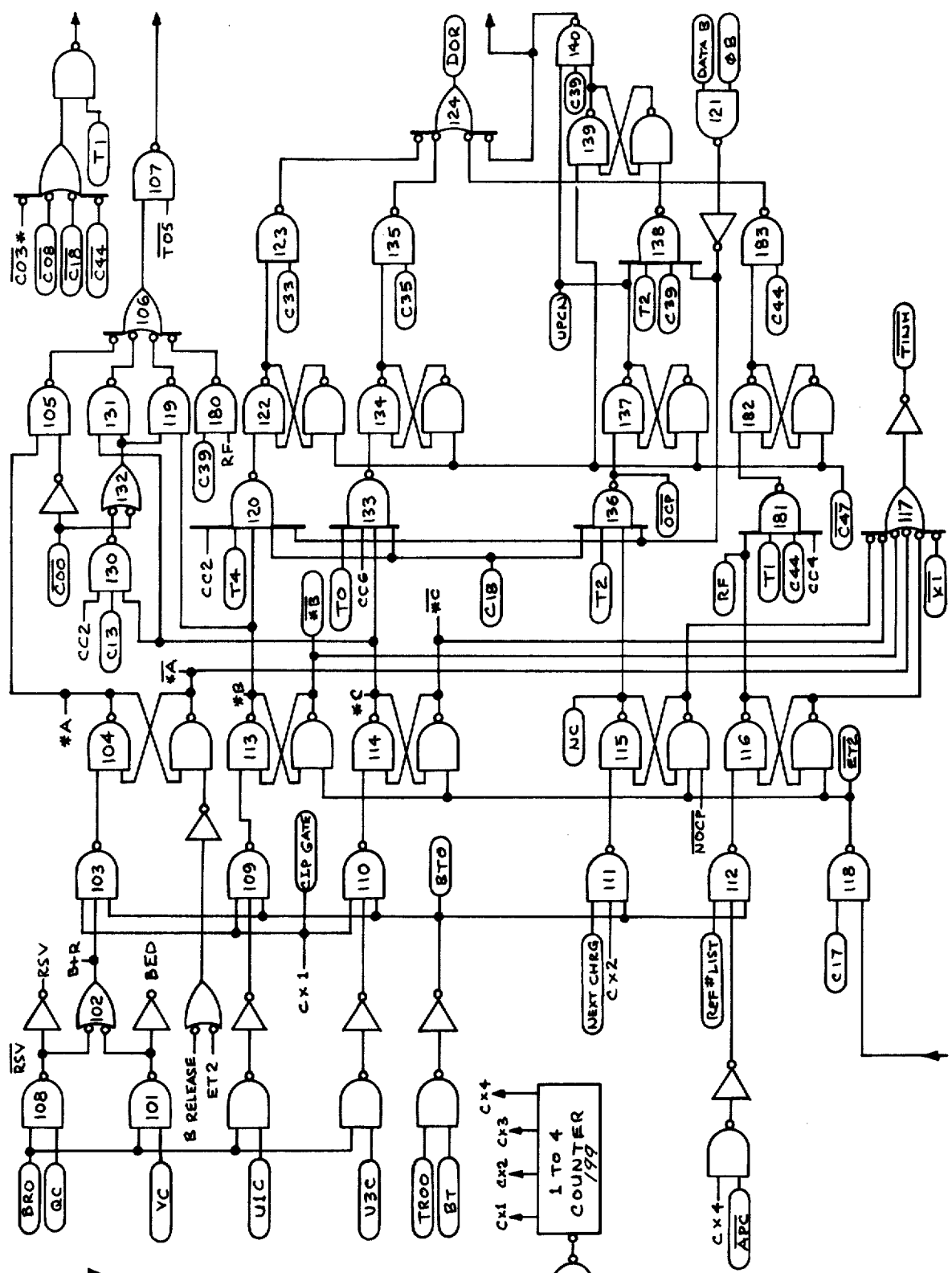
FIGS. 1-4 form a logic diagram of the bed information storage area control logic.

FIGS. 1–4, when placed together, include all the logic circuitry used to control flow of data into and out of the bed information storage areas. FIG. 1 contains primarily logic circuitry which is set up in response to control characters originally transmitted to the system from the various inputs. Control signals QC, VC, U1C, and U3C enter FIG. 1 from the upper left hand corner. These signals are respectively generated by the system 3700 in response to the receipt of Q, V, U1, and U3 control characters. The NEXT CHRG signal also enters FIG. 1 to initiate a search for a new patient number during an APC search. The REF # LIST signal enters FIG. 1 to initiate a search for bed storage areas containing a particular reference number or reference date. Control signals FC and DC, which are generated by the system 3700 in response to the receipt of F and D input control characters, enter FIG. 2 and initiate respectively the erasure of the patient information from a storage location or the insertion of new patient information into a storage location. As will be explained more fully below, these characters accompany a VC control character.

Figure 2:
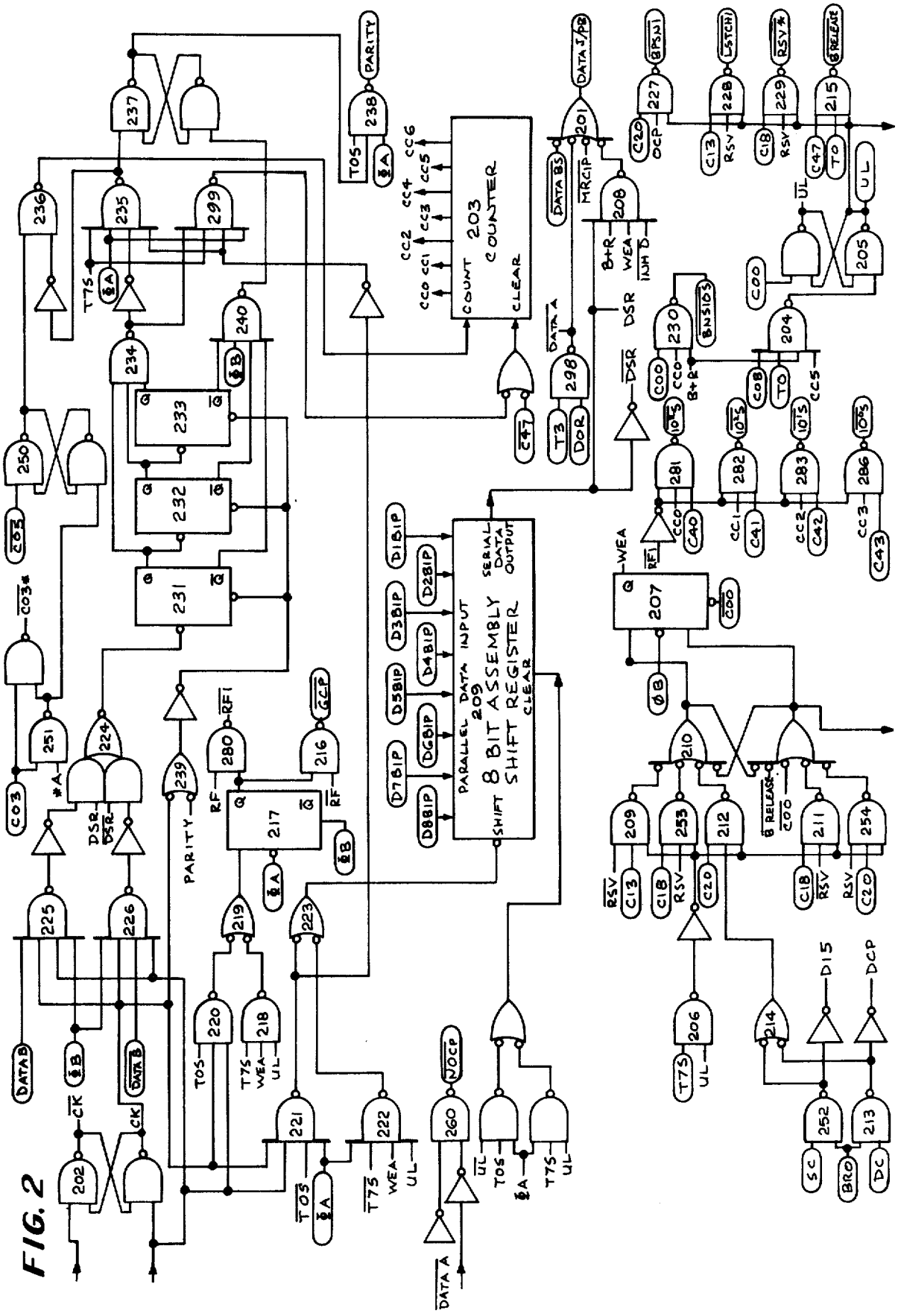

The upper portion of FIG. 2 is a comparator that compares data within the bed storage area to data stored within the core memory. The results of this comparison are then sent back to FIG. 1 and used to determine when a desired location has been found. The lower portions of FIG. 2 control the flow of new data into the bed information storage area, and also control the erasure of old data from the bed information storage area. This logic also overflows into the upper right hand portion of FIG. 4.

Figure 3:
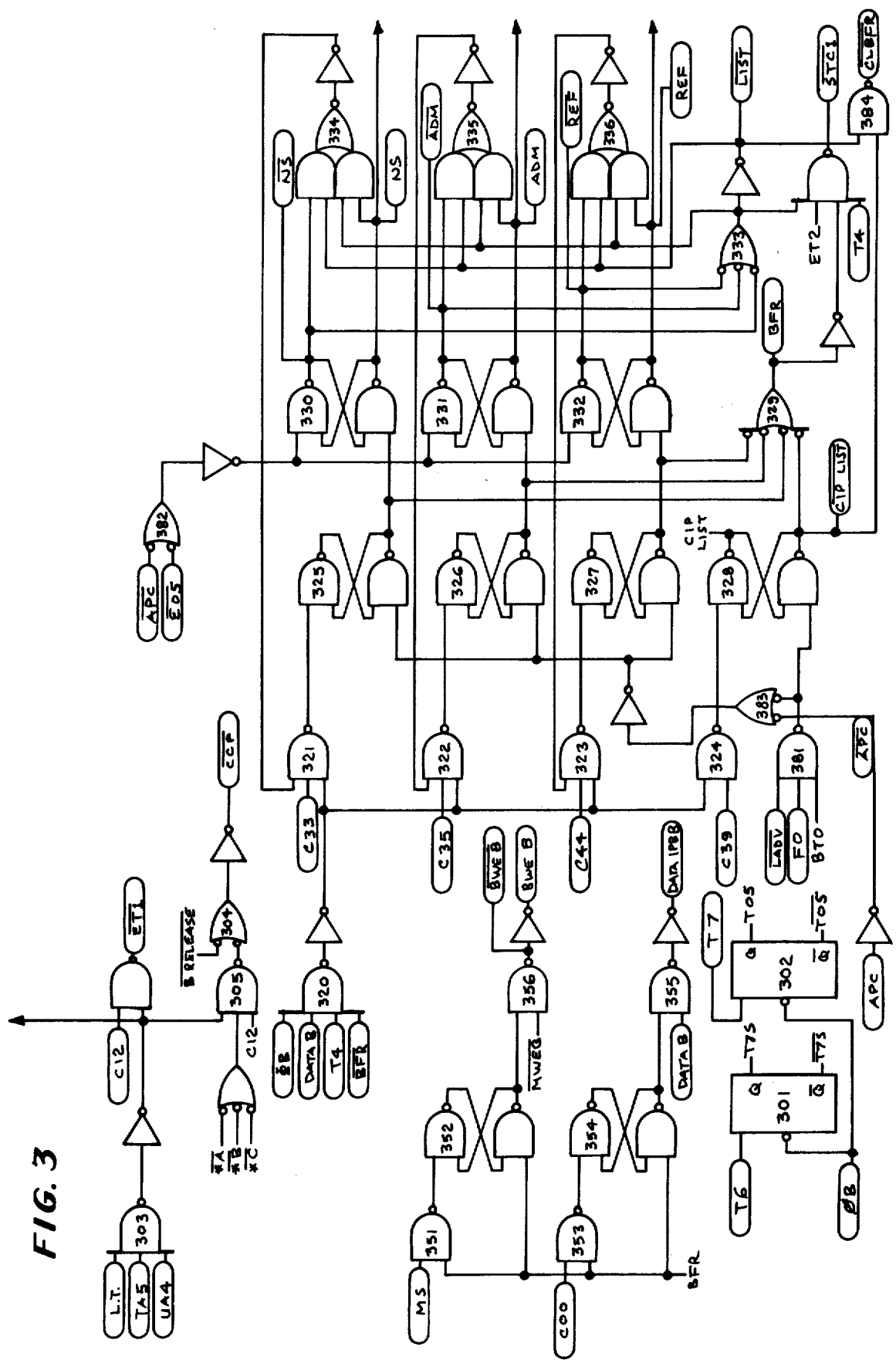

The logic controlling the writing of information into the buffer track of the bed information storage area is located in the lower middle left hand section of FIG. 3. The signal which determines whether information is being written into the buffer track or read from the buffer track is the BWEB (buffer write enable bed) signal. When this signal is positive, information is written into the bed information buffer storage area. The lower right hand portion of FIG. 4 controls the writing of information into the main bed information storage area. The control signal here is called the MWEB (memory write enable bed) signal.

The major portion of FIG. 3 contains logic circuitry which scans the bed information storage area continuously for printout markers whenever information is not being read into the bed information storage area. When a printout marker is found, a BFR (buffer) signal is generated to initiate a transfer of information from the main storage track to the buffer track. This transfer operation is controlled by the logic shown in the central part of FIG. 4.

As mentioned above, a certain amount of data is permanently stored in each of the many bed information storage locations. This information includes a nursing station number, stored in characters 1 and 2; a bed number stored in characters 3 to 7; and a bed price stored in characters 9 to 12. When the system is first put into operation, this information is fed directly to the drum through a gate 201 in the form of a DATA-BS signal. During this time, the drum head is enabled to write by a WEBS signal which passes through a gate 401 and a gate 402 and becomes the MWEB signal.

When a patient is assigned a bed, the admission office transmits into the system a card containing patient information, and a card containing a V control character and a D control character. These control characters cause VC and DC signals to be generated, as explained in the concurrently filed application. The VC control signal is fed into a gate 101. A second input to the gate 101 receives a BRO signal which is generated by the system 3700 after all the input data has been fed into the core memory, as will be explained below. These two signals cause the gate 101 to generate a BED signal. The BED signal passes through a gate 102 and partially enables a gate 103. The lower input to the gate 103 receives a BTO signal. This signal is positive when the bed information track counter is set to the first track and during the duration of a BT (beginning of track) signal that is positive just before the end of the head delay period. This BTO signal indicates that the bed track counter and the drum are in position to perform a complete scan of the entire bed storage area.

A CX1 signal is fed into the remaining input gate 103. This signal is generated by a 1 to 4 count counter 104 during this same period. The counter 104 advances very rapidly in response to the PHASE A signal during each BT (beginning of track) period, except when a TINH signal is present. The TINH signal disables a gate 105 and prevents the PHASE A timing pulses from reaching the counter 104 whenever the bed control logic begins a search.

When all of the inputs to the gate 103 receive signals simultaneously, the gate 103 sets a bistable 104 which generates 8 bit assembly shift register 209 to the output gate 201 and on to the bed information storage area. Thus, the flip-flop 207 actually controls the flow of data into the bed information storage area.

The WEA signal will first go high during the latter portions of C13. This C13 signal is fed into a gate 209 along with the signal from the gate 206, and causes a bistable 210 to enable the next PHASE B pulse to toggle the flip-flop 207 into the Q state. The inverted RSV signal, which is also fed into the gate 209, is not present at this time, and does not disable the gate 209. This RSV signal will be explained more fully below.

The T7S timing signal applied to the gate 206 prevents the flip-flop 207 from toggling until the very end of the C13 timing interval. This T7S timing signal is generated by a flip-flop 301. A similar T0S timing signal is generated by a flip-flop 302. The T7S timing signal occurs just before the commencement of the T7 bit timing pulse and is used to initiate the writing of data upon the drum. Data returns from the drum storage area one bit later in time than when it is recorded, so the T0S timing signal, which occurs one T interval after the T7S timing signal, is used as an indication of when a new character is about to be read from the drum.

The output of the flip-flop 207 thus goes positive at the commencement of the C14 character timing pulse. (Actually during the last bit of the C13th teleprinter character so that data is read onto the drum one bit early.) This enables bed status information (OCD, CLN, RDY, ETC.) to be written into the 14th through 17th character positions of the bed information storage location a *A signal. This *A signal initiates a search of the bed information storage area for a location containing the bed and nursing station numbers included in the patient information data stored within the core memory. The *A signal enables a gate 105 to pass a C00 character timing signal to a gate 106. This signal arises when the drum head reaches the beginning of each storage location within the bed information storage area, as explained above. The output of the gate 106 is inverted by a gate 107 and sets a bistable 202, causing the generation of a CK signal. The bistable 202 controls the operation of the data comparator. When the CK signal is present, data retrieved from the bed storage area is compared with data retrieved from the core memory. The exact details of this comparator will be described below.

The comparison operation continues until finally a storage location is found that contains a nursing station number and bed number that match the nursing station and bed number which were fed into the system on the patient information card. When this happens, a 0 to 6 counter 203 generates a CC5 signal. This CC5 signal, a C08 character timing signal, a T0 bit timing signal, and a B+R signal generated by the gate 102 are all fed into a gate 204. The gate 204 sets a bistable 205, and initiates the generation of a UL signal. This UL signal causes data to be read into the bed information storage location currently being read. The UL signal is combined with a T7S timing pulse by a gate 206. The output of the gate 206 enables a whole series of gates which control the state of a flip-flop 207. The WEA signal output of the flip-flop 207 enables a gate 208 (along with the B+R signal generated by the gate 102) to pass core data from an before the drum write head, and also allows the control D character, which is stored in core right after the bed status number, to be written into the 18th character position. The writing process is then terminated by a signal generated by a gate 211. The gate 211 causes the bistable 210 to reset at the end of the T6 bit of the C18th character. This causes the flip-flop 207 to terminate the WEA signal one bit before the beginning of the C19th character, thus temporarily terminating the process of writing data into the bed information storage area.

The storage process is recommenced during the character timing pulse C20 by a gate 212 which is enabled by the DC (D control character) signal. The DC signal goes through gates 213 and 214 to the gate 212. Thus, the write-in of data into the storage area recommences during the C21 character timing pulse (actually during the last bit of the C20 pulse) and does not terminate until a B RELEASE signal is generated during the T0 part of the C47 character timing pulse. The B RELEASE signal is generated by a gate 215 and is fed directly into the bistable 210 to terminate the writing process.

The output of the bistable 210 is fed directly to the gate 402 to generate an MWEB (memory write enable bed) signal whenever the flip-flop 207 is feeding data into the memory, thus enabling the drum to write data.

To prevent false printout markers from being generated, the feeding of data to the drum is suppressed during C33, C35, C39 and C44 by an INH D signal generated by a gate 403. The INHIBIT D signal is fed directly to the gate 208 to inhibit the flow of data into the bed information storage area. The inputs to the gate 403 are the outputs of the four gates 404 to 407. These gates are enabled by the UL signal and by the character timing signals C33, C35, C39, and C44. These same character timing signals are used to prevent the BR0 signal from advancing the core address register during these intervals, as is shown by the core address register circuitry disclosed in the concurrently filed application. It is necessary to inhibit the operation of the four gates 404 to 407 during T7 bit timing intervals so that the first bit of information in each of the following characters, which are read out of the core memory during the T7 timing interval, are not eliminated. This is done by applying an inverted T7 bit timing signal to an input of each gate.

It is necessary to coordinate the operation of the various circuits within the bed information storage area control logic with the operation of the core storage area location counter 3726 so that data can be fed from the core storage area 3720 in a proper sequence for comparison and for reading into the bed storage area. The BR0 signal initiates a serial parallel read out of data from the core memory during T5, as is shown by the core read out circuitry disclosed in the concurrently filed application. This same BR0 signal also enables the core address register to advance during each T3 bit timing interval. The circuitry for doing this is also disclosed in the concurrently filed application.

Data from the core memory is fed through the gating circuitry disclosed in FIG. 29. In response to a GCP signal the data is gated in parallel form into an eight bit assembly shift register 209. The GCP gating signal is generated by a flip-flop 217 and passed through a gate 216. The gate 216 also receives an inverted RF signal, which for the moment can be assumed to be positive.

The flip-flop 217 initiates the generation of the GCP signal when it receives an enabling signal from the gate 218 through the gate 219. This input is used when information is to be read into the bed information storage area. The three signals which enable the gate 218 are the WEA signal generated by the flip-flop 207, the UL signal generated by the bistable 205, and the T7S data read in timing signal. These signals cause a new 8 bit data character to be shifted into the 8 bit assembly shift register 209 at the start of the T7 bit of each character timing interval. This is the proper timing for loading the register when writing data into the drum storage area.

When information is to be read out of the bed information storage area for comparison, the timing of the data coming from the core memory must be slightly delayed to compensate for the 1 bit delay in drum output timing as compared to drum input timing. This delay in generation of the GCP signal is produced by enabling the flip-flop 217 with the gate 220, rather than the gate 218. The gate 220 input signals are the T0S output data timing pulse signal, the CK signal generated by the flip-flop 202 whenever a comparison is in progress, and the output signal from the gate 107 which also includes T0S timing pulses. Thus, whenever a comparison is in progress, data is transferred from the core memory into the 8 bit assembly shift register 209 at the very end of the T7 bit of each character signal.

Data is shifted out of the 8 bit assembly shift register 209 by shift pulses generated by either of two gates 221 and 222. The output of these two gates are combined by a gate 223 and are fed into the shift terminal of the 8 bit assembly shift register 209. The gate 221 initiates the shifting of data during comparisons. Two input signals to the gate 221 are the signals fed into the gate 220, which controls the readout of data from the core memory during comparison. The remaining two inputs of this gate are the T0S timing pulse signals and a PHASE A timing signal. The PHASE A timing signal actually advances the data through the assembly shift register. The T0S timing signal prevents the generation of the shift pulse while data is loaded into the register. The gate 222, similarly, includes as its inputs the PHASE A timing signal, T7S timing signal and the two other signals which enable the gate 218. The two gates 221 and 222 function in the same manner.

The data output of the 8 bit assembly shift register 209 is called the DSR signal. It is fed into the gate 208. It is also fed into the comparison gate 224, where it is compared with the DATA B signal coming from the bed information storage area. The DATA B signal is fed through two gates 225 and 226 during the PHASE B timing signal and into the remaining inputs of the comparison gate 224. The gates 225 and 226 are enabled by the CK comparison signal generated by the bistable 202, and also by the signal generated by the gate 107. A pulse appears at the output of the gate 224 each time the bit from the core memory is identical to a bit supplied by the DATA B signal. The resulting train of pulses is then fed into the comparator counter, which will be explained in more detail below.

Whenever data is read out of the core memory 3720 either for comparison purposes or for data transferring purposes, it is necessary to initially set the core address counter 3726 to some predetermined value where the first item in the list of desired information is stored. This operation is performed by the gates 227 through 230 and by the gates 408 and 409. For example, the gate 230 causes the core address location counter to be set to the address where the first digit in the nursing station number of the patient charge information is stored. This gate is enabled during the C00 character when the 0 to 6 counter 203 is at a count of CC0, indicating no comparison has been carried out, and when the B+R signal generated by the gate 102 is present, indicating a QC or VC control operation. Once the core address register counter 3726 is set to an initial address, it automatically advances serially through the core, so no additional control signal need be used until a new block of data stored in a different location is desired. The operation of the remaining gates in this group are all similar to the operation of gate 230.

The comparator is located in the upper portion of FIG. 2. This comparator counts the pulses generated by the comparison gate 224. Flip-flops 231, 232, and 233 together comprise an 8 bit counter. When 7 bits have been counted, the flip-flops present a full house count to a gate 234 and cause the gate 234 to generate a pulse. This pulse is passed through the gate 235 when that gate is enabled by a shift register advance pulse generated by the gate 221. The resulting pulse passes through the gate 236 and advances the counter 203. The pulse generated by the gate 235 also sets a bistable 237 which enables the gate 238 to generate a PARITY (comparator reset) pulse during the PHASE A part of the T0S timing signal. This PARITY reset pulse is fed to a gate 239 and is used to reset the three flip-flops 231, 232, and 233. When the three flip-flops are cleared, they enable a PHASE B signal to pass through a gate 240 and to reset the bistable 237. Thus, each time 7 bits within a character supplied by the DATA B signal match 7 bits supplied by a core memory, the counter 203 advances by one count. The resulting count can therefore be used as an indication of the number of characters which have been successfully matched in the two signals.

If all the bits in the two characters that are compared do not match up, the full house count condition is not reached. In this case, the gate 234 enables a gate 299 which clears the counter 203, erasing the record maintained in that counter of successful comparisons.

The comparison procedure is controlled by the bistable 202 and by the CK signal. When the CK signal is absent, no comparison is performed, and the counter 203 retains its count. Thus, by toggling the bistable 202 in and out of the set state, different sections of the two masses of data can be compared for different purposes. Examples given below will explain how this feature adds great flexibility to the types of searches which can be performed by the system.

It was mentioned before that a VC control character causes the bistable 104 to generate a *A signal, and that the *A signal initiated a search through the bed information storage area for a nursing station number and a bed number which matched the one included in the patient charge information stored in the core memory. This search is performed in the following manner. As data from each sequential location within the bed information storage area is presented to the comparator, the bistable 202 initiates a comparison. The comparison gate 224 compares the first and second characters supplied by the DATA B signal to the nursing station number stored in the core memory. If the comparison of these two characters are successful, the counter 203 advances to a count of CC2. The comparison procedure continues, but the counter 203 is prevented from advancing for two character counts by a bistable 250 which disables the gate 236. The bistable 250 is toggled by a C03 signal whenever a *A signal is present. The counter 203 is enabled again during the time when the fifth character is compared. A C05 character is used to reset the bistable 250, thereby re-enabling the gate 236. In this manner, the two digit nursing station number and the five digit bed number are compared to data in the core memory. If the comparisons are all successful, the counter 203 will advance to a count of CC5. If any comparison was unsuccessful the counter 203 will have been cleared, and the CC5 signal will not be present. The CC5 signal, when present, enables the gate 204 so that the bistable 205 can initiate the UL signal and the data storage process. Thus, the above search is performed by comparing the nursing station number and the bed number within each storage location to data stored in the core memory. Other types of searches will be explained below. They differ in details from the above search, and in the particular characters which are compared. However, the general procedure is identical to that described above.

If the system input data included an S control character rather than a D control character, patient information is erased from the location found. The SC signal generated by this control character is applied to a gate 252 along with the BR0 signal. The resultant DIS (discharge) signal generated by the gate 252 passes through the gate 214 and into the gate 212, where it initiates loading of information into the bed information storage area in exactly the same way that the DC control signal initiated loading of information into the area. The DIS signal also enables a gate 410. This gate clears the flip-flop 411 during the 7th bit of the 20th character. The output of the flip-flop 411 passes through the gate 403 and initiates an INHD signal. This signal prevents any information from being read into the bed storage area. The MWEB signal erases the information previously stored in this area, so this procedure effectively erases all old patient information from the storage location. The flip-flop 411 is then reset by C47 character timing signal.

If an input data card contains a Q control character instead of a V control character, a gate 108 generates an RSV (reserve) signal in response to the QC (Q control)

signal which causes a reservation mark supplied along with the input data to be written into the nineteenth character slot within the location containing the specified bed and nursing station number. The RSV signal is fed through the gates 102 and 103, and initiates a *A search that is identical to the search performed in response to the V control character. The RSV signal causes a different set of gates feeding into the bistable 210 to be energized, and therefore causes a reserve character to be written into the core memory rather than patient information. The RSV signal enables the gates 253 and 254 to set the flip-flop 207 at the beginning of the C19 and to clear the flip-flop 207 at the beginning of C21. The only information read into the core memory is the reservation mark, which ends up in character slot 19. The gates 209 and 211 are inhibited by the RSV signals.

That completes the description of the circuitry which reads information into the bed information storage area. The following paragraphs will describe how searches are initiated, and how marker bits are written into those areas containing information which is to be printed out.

Four different kinds of searches are performed within the bed information storage area. In response to a U1 control character, as indicated by a U1C signal, a search is made for all bed numbers in locations contining a specified nursing station number and control characters indicating a need for special attention or service. This list is called a nursing station work list. In response to a U3 control character, as indicated by a U3C signal, a search is made for bed numbers in storage locations containing a given set of status characters. This search is initiated by the admitting office, and the results of this search are fed directly back to the admitting office. A NEXT CHRG search is commenced in response to a NEXT CHRG signal generated during the all patient charges printout procedure. This search scans the bed information storage locations for a patient case number for which the day's charges have not yet been printed out. When such a patient number is found, a mark is placed in the data and a search for charges relating to that patient is commenced in the charge information storage area of the system, as will be explained below. The final bed area search is the REF # LIST search initiated by the business office to find all bed storage areas which contain a given reference number or date. Usually this number is the date on which the patient was admitted to the hospital. This search is useful for finding where patients admitted on certain dates are located within the hospital. This search is initiated by push button. The desired reference number is set up on a set of dials, and a button is depressed which generates a REF # LIST signal. The results of this search are transmitted directly to the business office teleprinter.

Two different forms of searching mechanisms are provided by the present system. The first is the comparator, which has been described above. The comparator compares certain data within each bed storage location to data supplied by the core memory or by some other input register, and marks for printout all locations containing data identical to the reference data. Except for the marking procedure, the nature of this type of search has been fully described above.

The second form of search involves examining the 18th character in each location to detect the presence or absence of certain bits. If the specified bit is present, then the information in that storage area is included in the lists; otherwise, the information in that storage area is passed by. Location C18 can contain any one of four characters—a control D character, a control S character, a control P character, or a space. These control characters are fed into the storage location along with other input data as if they were a fifth character in the four character bed status number. The control D and the control F character are detected by the system 3700, and are used to initiate the insertion or the deletion of the patient number from a particular bed storage area, as was explained above. The control P character and the space have no special control functions in the present embodiment, although the system does generate a PC signal when it receives a control P character. All four of these characters, however, contain characteristic bit arrangements which can cause the contents of a location to be included or excluded from a particular list. In particular, the control D character contains a positive T2 bit. All other bits in this character are "0"s. The control D character causes the information in a location to be included in the patient charge number search during an all patient charges printout. Locations in the bed storage area not containing a control D character are bypassed during the patient charge number search. Since the control D character contains "0"s in bit position 5, areas containing a control D character are not included in the nursing station work list.

The control S and P characters contain a "1" in bit position 5, and a "0" in bit position 3. Locations containing a control S or control P character are included in the nursing station work list search (U1), but are not included in the patient charge number search. If a space is included as a control character, the location is not included in either of the above lists. The reference list search and the admitting office U3 search do not make use of these control characters, and are not affected by the particular control character present.

The counter 199 scans all of he different search control inputs at the beginning of each bed information storage area scanning cycle to determine if any searches are to be made. CX1, CX2, CX3, and CX4 signals are generated repeatedly for a short period of time. If there is a search to be made, of if there is data to be written into the bed information storage area, the counter 104 will enable one of the gates 103, 109, 110, 111, or 112, and will cause one of the bistables 104, 113, 114, 115, or 116 to cause a gate 117 to generate the TINH signal. This TINH signal stops the counter 104 and prevents any other searches from being initiated until the current search is completely carried out. The search which is to be carried out is determined by the particular bistable which was set. The bistable 113 generates a *B signal and initiates a U1C or nursing station work list search. The bistable 114 generates a *C signal and initiates a U3C, or admitting office search. The bistable 115 generates an NC signal which initiates a new patient number search. The bistable 116 generates an RF signal which initiates a reference number list search.

Searches are terminated when the corresponding bistable is reset. This resetting is accomplished by a gate 118 when the last storage location in the bed information storage area has been scanned. The gate 118 is enabled to generate an ET2 signal by a C17 signal, and a last track address 54 signal generated by a gate 303. Since a write-in search (control Q or V) can be terminated as soon as data has been written in, the *A signal is terminated early by the B-RELEASE signal generated by the gate 215. If no bed is found, then the bistable 104 is reset by the ET2 signal.

The nursing station work list search is initiated by a *B signal. The resultant list includes all bed numbers containing a specified nursing station number and containing a "1" in the 5th bit of the character C18 (areas including a control S or a control P character). The *B signal enables the gate 119 to pass a C00 character through the gate 106 and a gate 107 to set the bistable 202 causing it to generate the CK signal and initiate a comparison during charcter timing intervals C01 and C02 (nursing station number comparison). If the comparison is successful, a CC2 signal is fed back to a gate 120. The other inputs to the gate 120 are the *B signal, a T4 timing signal, a C18 character timing signal, and the output data from the bed information storage area combined with a PHASE B signal by a gate 121. If the 4th bit of the 18th character is a "1", the gate 120 is enabled and sets a bistable 122. The bistable 122 in turn enables a gate 123 to pass a C33 character timing signal to a gate 124. The gate 124 is thus induced to generate a DOR signal during character count 33. This DOR signal enables a gate 298 to transmit a mark to the 4th bit position within the 33rd character slot of the storage location currently being scanned. The output of the gate 298 is called the DATA A signal. This signal is also applied to the gate 402 to cause the drum logic to write this mark into the bed information storage area. This printout mark can later be detected by printout marker detection logic, and the information can be fed into the buffer storage track for printout. In this manner, all items which are to be included in a given nursing station work list are marked for printout in response to the *B signal.

The admitting office list printout is initiated by a *C signal. The *C signal enables the gates 130 and 131. A C00 signal flows through a gate 132 and into the gate 131 to initiate the comparison of nursing station numbers. If a nursing station number comparison is successful, a CC2 signal fully enables the gate 130 to restart the comparison procedure at C13, which is the timing character that occurs just before the bed status characters are read out of the storage location. A four character comparison is then carried out on the bed status characters. If this comparison is also successful, the counter 203 ends up at a count of CC6. The CC6 signal partially enables a gate 133. At the first bit in the 18th storage slot, the gate 133 is fully enabled and toggles a bistable 134. The bistable 134 enables the gate 135 to cause a printout marker to be placed into the fourth bit of the 35th character slot. In this manner, each item in the admitting office list is marked for printout.

A search for a new patient charge number does not make use of the comparator. A check is made of the contents of the third bit within the 18th character in each storage location. If a "1" is found, then this location contains a control D character, and is a candidate for inclusion in the search. The gate 136 is then enabled to generate an OCP signal, which causes the patient charge number to be read out of the bed storage location and into a patient number shift register 3118 (FIG. 31) which will be described in a later section of this specification. The OCP signal also sets a bistable 137. The bistable 137 initiates a check of the second bit within the 39th character slot, to see if this charge number has already been fed to the APC (all patient charges search) circuitry. If it has, a "1" will be found in this location. The gate 138 is then enabled to clear the bistable 139, disabling the gate 140. The output of the bistable 137, which was originally intended to pass through the gate 140 and place a mark in the fourth bit position of the 39th character slot, is disabled, and this item is not marked. If the third bit within the 39th character does not contain a "1", a mark is placed in the fourth bit position of the 39th character. Additionally, the output of the gate 140 enables the DATA A signal to pass through a gate 260, generating an NOCP signal. This NOCP signal is used to reset the bistable 115. The bistable 139 is reset by an inverted C47 pulse.

The reference list search is initiated by the bistable 116 which generates an RF signal. This RF signal enables the gate 180 to pass a C39 character timing pulse to the bistable 202, initiating a comparison between the reference number, which is stored in character locations C40 through C43, and a reference number which is manually placed into a reference list input unit 2901 (FIG. 29) located in the business office. The comparison is carried out in the usual manner, and a successful comparison is indicated by a CC4 signal generated by the counter 203. The CC4 signal enables a gate 181 to set a bistable 182, in turn enabling a gate 183 to initiate the marking of the T4 bit within the character C44. The RF signal also enables a gate 280 which is connected to the output of the flip-flop 217, and disables the gate 216. Now, instead of data being read into the eight bit assembly shift register 209 from core, data is read into the same register from a buffer 2902 (FIG. 29) that contains the desired reference number. The output of the gate 280 enables a series of gates 281, 282, 283, and 284 which read out individual digits from the buffer 2902 and transfer these digits into the eight bit assembly shift register 209. The gate 281, for example, is enabled when the counter 203 generates a CC0 signal during character count C40. Similarly, the gate 282 is enabled during character count C41, the gate 283 is enabled during character count C42, and the gate 284 is enabled during character count C43. The output signals from these gates are fed to the logic shown in FIG. 29, which will be described more fully below.

When a search for items which make up a list is completed, or when the B RELEASE signal is generated by the gate 215, a CCP signal is generated to indicate that the search is completed. This signal is generated by a gate 304. One input to the gate 304 is the B RELEASE signal; the other input is the output of the gate 305. The gate 305 generates a pulse whenever an *A, a *B, or *C search reaches the twelfth character location within the fifth-fourth storage location of the last track in the bed information storage area.

Figure 4:
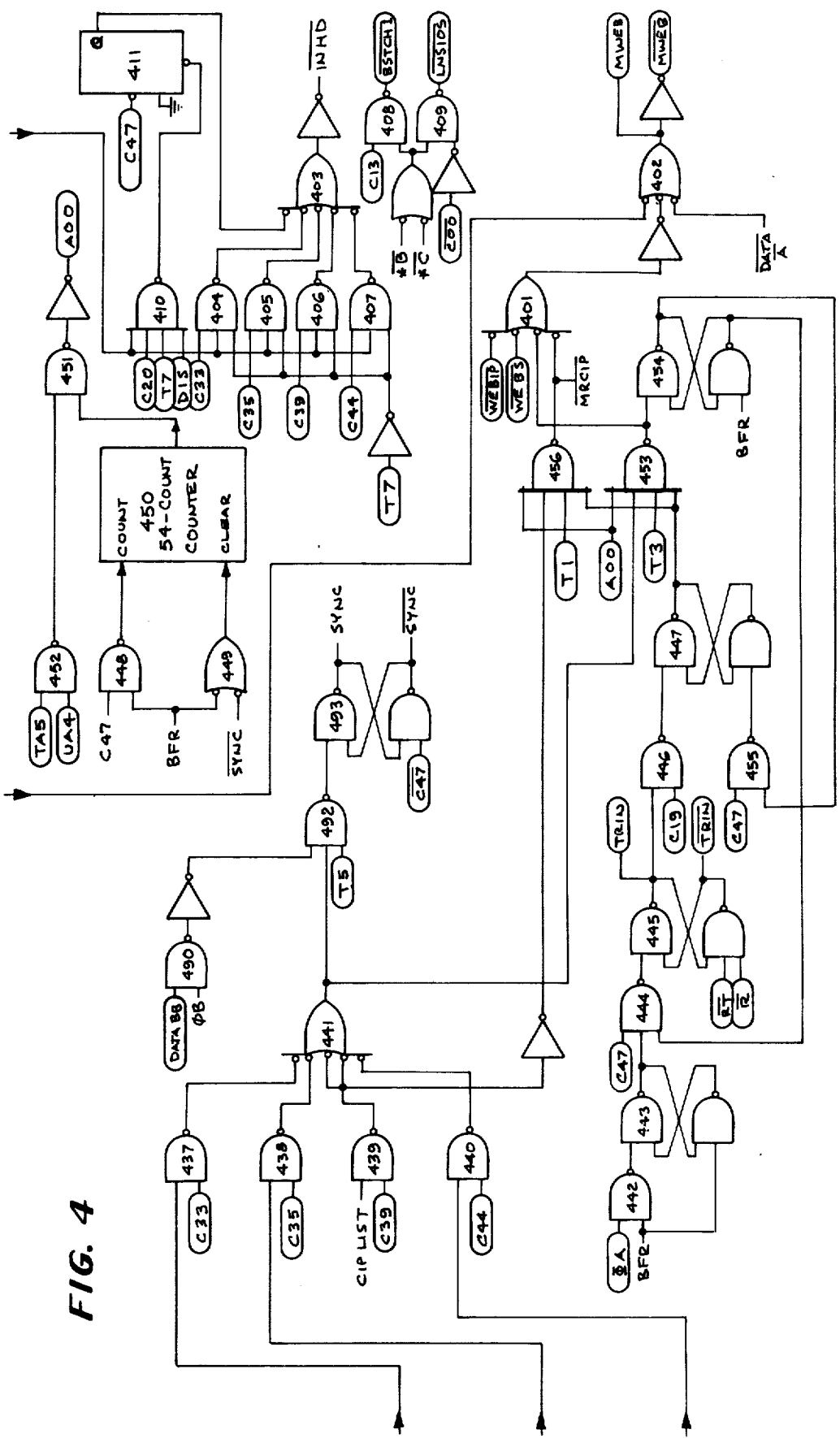

The remaining logic circuitry shown in FIGS. 3 and 4 is used to detect printout markers, to transfer the marked data from the main storage area to a buffer storage area, and then to transmit the data from the buffer storage area to the proper output teleprinter.

Whenever a list search of some form is not in progress, data from the bed information storage area is fed to a gate 320 along with a PHASE B timing signal, a T4 bit timing signal, and an inverted BFR signal. For the moment, the inverted BFR signal can be assumed to be absent, enabling the gate 320. When a location in the bed information storage area is found that contains a "1" in the fourth bit of a character slot, the gate 320 partially enables the four gates 321-324. The gate 321 is totally enabled when such a mark is found in a 33d character slot. Such a mark indicates an item in a nursing station work list, and sets a bistable 325. Similarly, other printout marks set the three bistables 326-328. The output signal from any one of these bistables enables a gate 329 to generate a BFR (buffer) signal. This signal, in inverted form, is fed back to the gate 320 to prevent any other printout markers from being detected until this first one is completely processed.

The output signal from the set bistable, at least if it is one of the bistables 325–327, sets a second bistable 330–332. The output of the set bistables 330–332 then causes a gate 333 to generate a LIST signal. This LIST signal is compared with the output of each of the three bistables 330–332 by three comparison gates 334–336. The comparison gate associated with the printout marker generates a signal that enables the corresponding input gate 321–323. The other input gates are disabled by their respective comparison gates. Note that before a marker was encountered, all of the three comparison gates generated enabling signals for their respective input gates.

The three bistables 330–332 generate respectively an NS (nursing station) signal, an ADM (admitting office) signal, and an REF (reference number seearch) signal. Only one of these signals is positive at any one time, the one associated with the marker that was found. That signal, or the CIP LIST signal generated by the bistable 328, enables one of the four gates 437–440 to pass an appropriate character timing signal to a gate 441.

The BFR signal, which had previously been holding a bistable 443 in the clear state, now enables a gate 442 so that a PHASE A timing pulse can set the bistable 443, enabling another gate 444. The character timing pulse C47 then passes through the gate 444 and sets a bistable 445, thus generating a TRIN (bed storage area track counter advance inhibit) signal. This signal stops the bed storage area drum logic from advancing to scan another track for one revolution. This signal also enables a gate 446 to pass a C19 character pulse and set a bistable 447.

The BFR signal is also fed to gates 448 and 449 which are associated with a 54 count counter 450. Before the BFR signal was initiated, it passed through the gate 449 and cleared the counter 450. After the signal is initiated, it enables the gate 448, to pass C47 timing pulses to the counter, advancing the counter. The counter 450 counts 54 C47 timing pulses, which is one complete revolution of the drum, and then enables a gate 451 to generate an A00 signal. This A00 signal continues to be generated during the time when the location on the drum track containing the information which is to be printed out is being read by the drum head. The A00 signal is regenerated with each drum revolution, and serves as an indication of when the marked location is below the drum read head. The gate 452 prevents the signal from being generated while the 55th location in the track is scanned.

During the next revolution of the drum, the marker bit is erased. This erasure is accomplished by a gate 453 which generates an erase signal. This erase signal is passed through the gate 401 and becomes the MWEB signal. The gate 453 is enabled during the A00 period of the next revolution, while the fourth bit of the location containing the marker bit is below the drum head, as determined by the character signal gate 441. The output of the gate 453 also sets a bistable 454 which enables a C47 timing pulse to pass through a gate 455 and reset the bistable 447. The termination of the BFR signal then clears the bistable 454. In the case of a CIP LIST marker, it is also necessary to mark the second bit of the 39th character so that the logic circuitry will know that this particular patient number has already participated in the APC search. This is accomplished by a gate 456 which is enabled in almost exactly the same way as the gate 453, but which is enabled at an earlier time by a T1 bit timing signal, rather than a T3 bit timing signal. This gate also applies a signal to the gate 401 to write a "1" bit on the drum. This signal, called the MRCIP signal, is fed to the gate 201.

The buffer track control logic appears at the lower left hand corner of FIG. 3. The buffer track write enable signal appears at the output of a gate 356. Data for the buffer track appears at the output of a gate 355. The gate 356 is controlled by a bistable 352, and the gate 355 is controlled by a bistable 354. Ordinarily, both of the bistables 352 and 354 are cleared by the BFR signal, so both of the gates 355 and 356 are enabled. Thus, the DATA B signal which contains the output data from the bed information storage area is continuously written and rewritten onto the buffer track. When a marker bit is found, the BFR signal goes positive and enables the two gates 351 and 353. The gate 353 allows a C00 timing pulse to set the bistable 354 after the location containing the marker bit has been completely recorded on the buffer track. This disables the gate 355, and causes a string of zeros to be written into the remainder of the buffer track. Thus, only the single marker bit is to be found within the buffer storage area. This marker bit can be used as a check to insure that the proper data is always read out. The gate 351 allows an MS (master strobe) pulse, which occurs at the end of a drum revolution, to set the bistable 352, thus terminating the erasure process and allowing the data from the buffer track to be read out. The data from the buffer track and the A00 timing signal are both used by the output sections of the system to produce an output signal including the marked information. The main drum storage area is released in the meantime, and is allowed to be used in further searches and data storing operations. Thus, the core memory and the data input sections of the system are never tied up waiting for data to be read slowly out of the bed information storage area to a low speed teleprinter.

When the information has been completely transmitted to the output teleprinter, a reset signal clears the bistables 325–328 and terminates the BFR signal. This reset signal is generated by a gate 381, the inputs to which are the BT0 signal, the BF0 signal from the bed information printout format generator circuit, and an inverted LADV signal which is generated by the clock circuit. The F0 signal indicates that the printout is completed. The LADV maintains the BFR signal until the time and data printout circuitry is available. The BT0 signal is generated when the beginning of the first track in the bed information storage area is first scanned. Thus, the BFR signal is terminated after the printout is complete and when the time and data printout circuitry is available.

After the flip-flops 325–328 are cleared, the inverted BFR signal, the ET2 signal generated by the gate 118, the LIST signal generated by the gate 333, and a T4 timing signal produce an STC1 (set time clock) pulse. This pulse is fed through some gates at the bottom of FIG. 6 and back to the calendar circuit to initiate a printout of the time and the date at the end of the list. When the calendar circuit is done, it generates an inverted EOS signal which passes throgh a gate 382 and clears the bistables 330, 331, and 332. There is no time and date printout during an APC operation. During APC, an inverted APC signal is passed through the gate 382 and is used to hold the bistables 330, 331, and 332 in the clear state, thereby disabling this part of the circuit. An APC signal is also applied to a gate 383 to lock the bistables 325, 326, and 327 in their clear states. This suppresses all searches other than those connected with the all . patient charges search from occurring while the APC signal is present. Note that printout markers can still be applied to the bed storage area during this time. Printout will then occur after the APC operation is terminated.

When no list printout is in progress, a CLBFR signal (buffer is clear) is generated by a gate 384.

To insure that the A00 signal remains exactly in sync, and does not change its positioning, the marker bit is read out of the buffer storage and is used to generate a sync pulse for the counter 450. The marker bit passes through a gate 490 and into a gate 492. The gate 492 is enabled during the character count when the marker should appear, and a T5 bit signal is applied to enable the gate 492 only during the bit timing when the marker should appear. When the marker appears, it sets a bistable 493 and generates a SYNC pulse that clears the counter 450. The bistable 493 is then reset by the C47 timing pulse. Although this sync circuit is only a safety feature when used in conjunction with the counter 450, a similar sync circuit is used in conjunction with the charge information storage buffer track, and is associated with a counter that does not automatically reset when it reaches the desired count. In that section of the system 3700, the sync circuit is absolutely necessary to reset the counter.

FIG. 29 shows the logic used to initiate a reference number search. The desired reference number is set up on a series of dials contained in a business office reference list input unit 2901, and a pushbutton on the input unit is then depressed. The unit 2901 then gates the reference number in BCD form from the dials to a twenty bit buffer 2902 and generates an REF LIST signal to initiate a reference list search of the bed information storage area. Four signals, $10^3$S, $10^2$S, $10^1$S, and $10^0$S gate the information out of the buffer 2902, through the output gates 2920 to 2926, and into the assembly shift register 209. This information is then used as explained above during the reference number search procedure. Core data, called for by the bed search logic, is also gated through the gates 2920 through 2926 by a GCP signal, which enables the gates 2910 through 2917 to pass core memory data to the gates 2920 through 2926.

Figure 28:
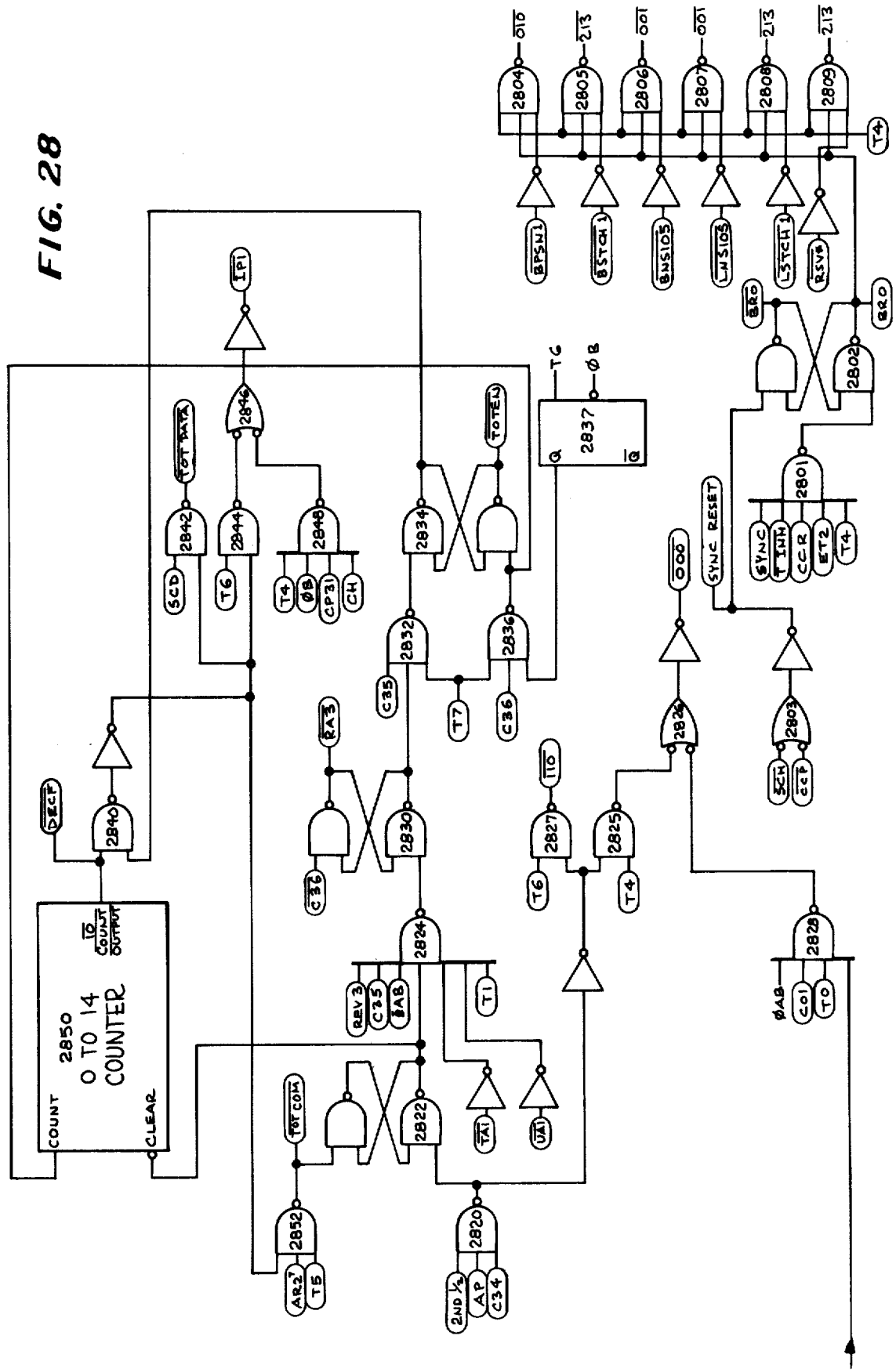
FIG. 28 is a logic diagram of the totals printout control logic, and of the logic circuitry for generating the BRO signal.

The circuitry for generating the BR0 signal which initiates the operation of the bed information control logic is shown at the bottom of FIG. 28. The BR0 signal is generated by a bistable 2802. This bistable is set up by a gate 2801 whenever a set of input data supplied to the core memory indicate that the bed information storage circuitry is to be used in some way. The input signals to the gate 2801 are a SYNC signal, which is generated after a set of input data is completely stored away in the core memory, a CCR signal, which indicates the input data included a control R, Q, E, U1, or U3 character, an ET2 timing signal which indicates the drum is at the end of a revolution, and a T4 bit timing pulse. The TINH signal from the gate 117 is also fed into the gate 2801 in inverted form to prevent the generation of a BR0 signal when a search of the bed information storage area is already in progress. The BR0 signal partially enables a set of gates 2804 to 2809. These gates generate pulses during the T4 timing interval to set the core memory address register to particular octal addresses as required. The gates 2804 through 2809 are enabled by a variety of bed signals generated by the logic shown in FIGS. 2 and 4. The BR0 bistable 2802 is reset by the CCP signal which passes through a gate 2803. It will be remembered that the CCP signal is generated when a bed information search operation is completed. This same CCP signal generates a SYNC RESET signal, which is used to reset a flip-flop that generated the SYNC signal. This flip-flop, and other details of the system input circuitry, are disclosed in the concurrently filed application.

When data is read into a bed information storage location, it is desirable to have a record of that information printed out. A printout of this information is initiated by a PO START signal generated by a gate 2701 after the information has been stored in the bed information storage area. The gate 2701 is enabled by the CCP signal and by a signal generated by a gate 2702 during the time when the fifty-fourth bed storage location on a track is being scanned. The inputs to the gate 2702 are a UA4 timing signal, a TA5 timing signal, and an inverted UC (U control character) signal. The inverted UC control signal prevents a printout of the input data which accompanied a list request, and limits printouts to data sets which include Q and V control characters. The PO START signal initiates an ordinary system printout of the type which is fully described in the concurrently filed application. (Gate 2204, FIG. 22 in Phillips, et al. U.S. Pat. No. 3,597,742).

If the input data accompanying a request to store data in the bed information storage area does not specify a valid bed number and nursing station number, the information will not be stored, and the CCP signal will not arise until the time when the last (54th) location in the last track of the bed information storage area is scanned. In this case, a gate 2703 generates an ERROR 1 signal. This ERROR 1 causes the system to reject the input data as faulty.

Figure 22:
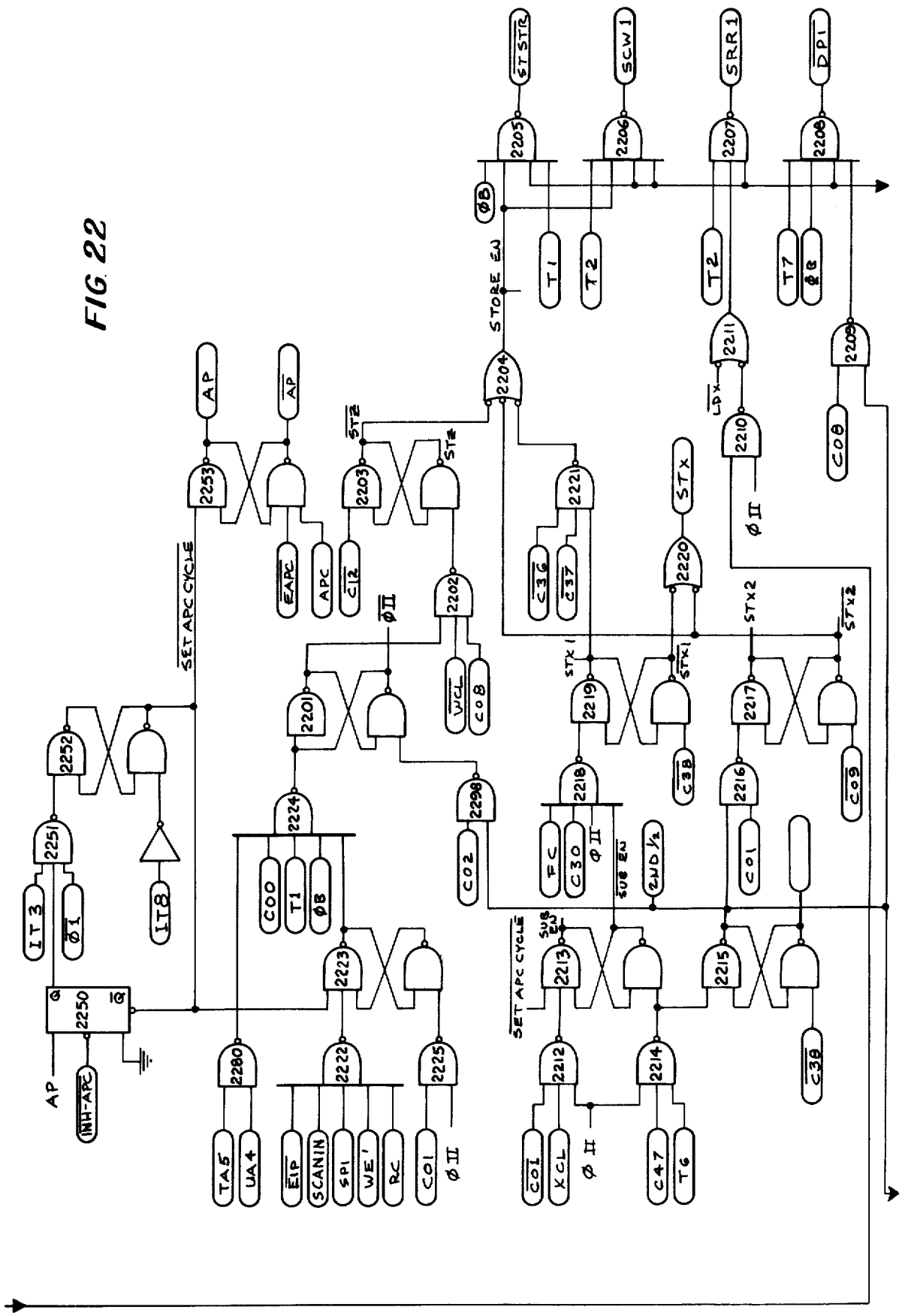

A similar printout of charge information can be initiated by combining the C RELEASE signal generated by a gate 2605 (FIG. 26) with an RC (control R character) signal in a NAND gate to form another inverted PO START signal as is shown in Phillips, et al. patent (Gate 2200, FIG. 22 in Phillips, et al. U.S. Pat. No. 3,597,742)

CHARGE INFORMATION STORAGE LOGIC

Figure 25:
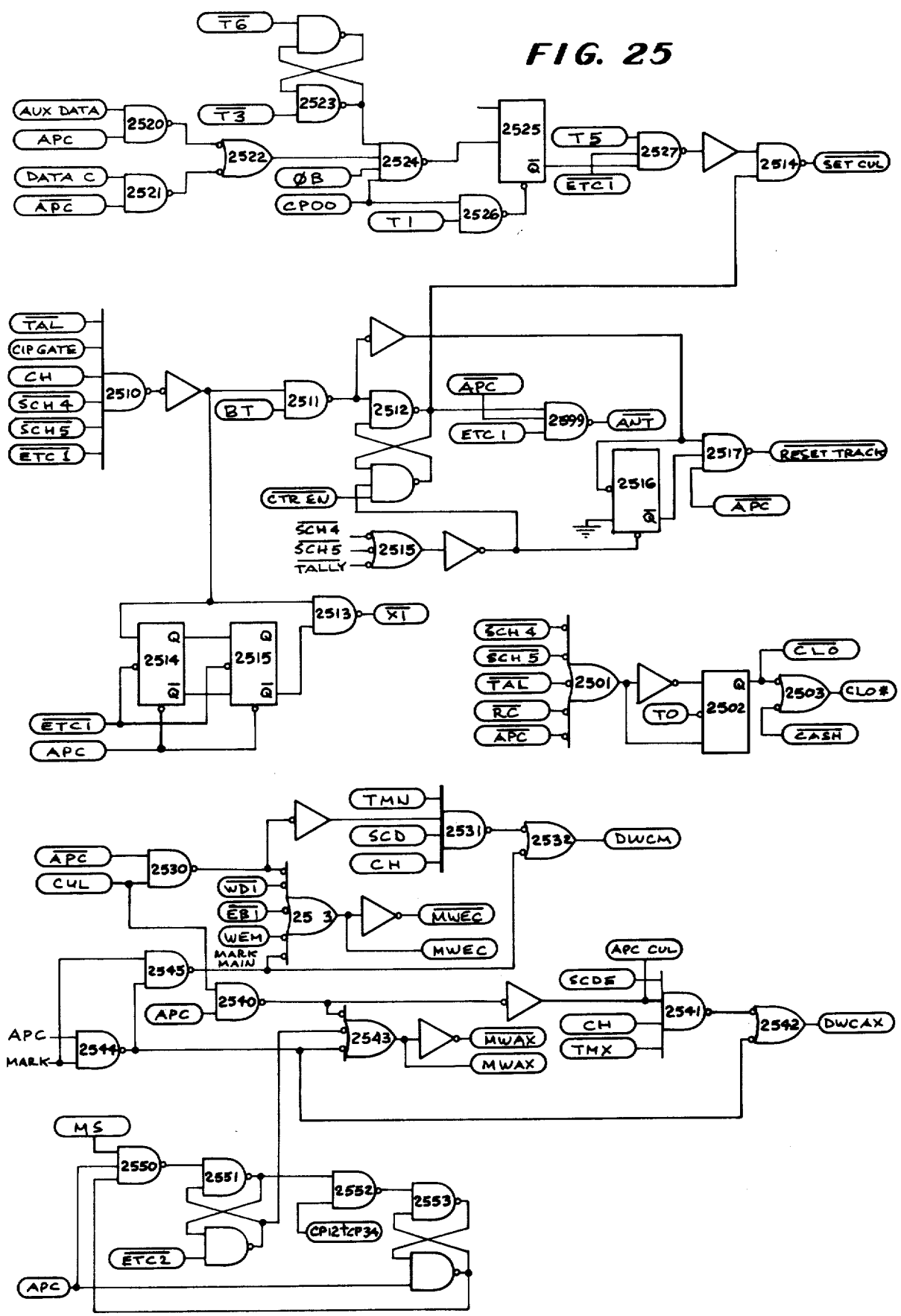
FIG. 25 and FIG. 26 form a logic diagram of the charge information storage logic.
Figure 26:
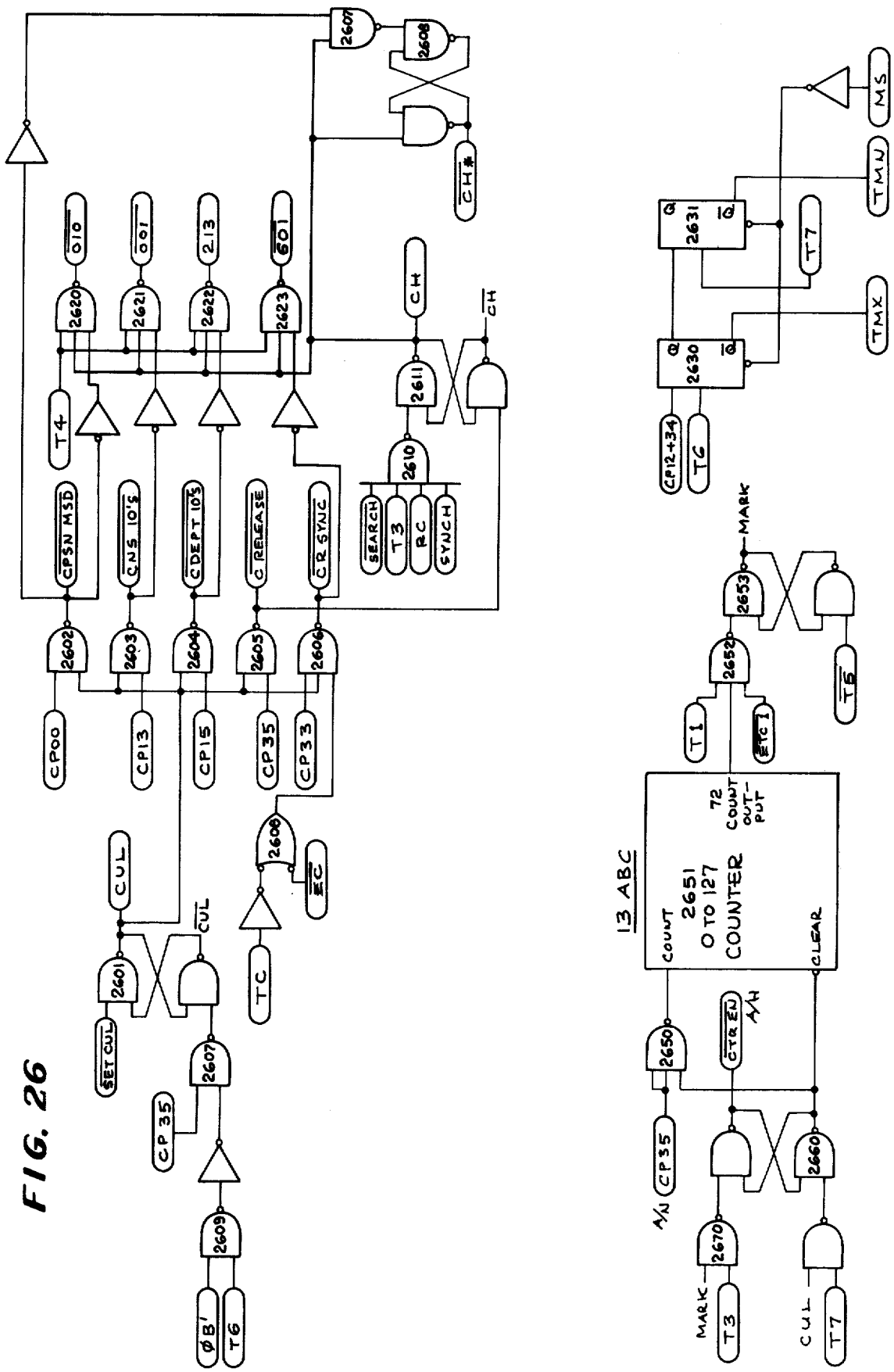

FIGS. 25 and 26 show the logic that is used to search the charge information storage area for an available location and to read charge information out of the core memory and into the location. This process is initiated by a CH (charge) signal generated by a bistable 2611. Bistable 2611 is set up by a gate 2610. The input signals to the gate 2610 are a T3 bit timing pulse, an RC (R control character) signal, and a SYNCH signal that is generated by the system 3700 after a set of input information is stored in the core memory. The gate 2610 is inhibited by a signal generated by a gate 3129 (FIG. 31) when some other search of the charge information storage area is in progress.

The CH signal is fed into a gate 2510. It enables the gate 2510 when the CIP GATE or CX1 signal generated by the counter 199 is positive, so long as TAL, SCH4, and SCH5 signals are not present indicating some other search is in progress. The gate 2510 is also inhibited by the presence of an ETC1 signal. When the CIP GATE signal is positive, the gate 2510 generates a signal which is passed through a gate 2513 to generate an XI signal. This signal if fed back to the bed information control logic and causes the T INH signal to be generated, thus locking the counter 199 so that it continues to generate the CIP GATE signal and maintains the gate 2510 enabled. This T INH signal then disables the gate 2801 shown in FIG. 28 and prevents the generation of a BR0 signal which otherwise might initiate a search of the bed information storage area. At the beginning of a track, the BT (beginning of track) signal and the signal from the gate 2510 enable the gate 2511 to set a bistable 2512. The output signal from the bistable 2512 initiates a search for a location within the charge information storage area that is empty. The output signal from the gate 2511 is also applied to one input of a gate 2517. Normally, the flip-flop 2516 is in the $\overline{Q}$ state and maintains the gate 2517 disabled, so the signal from the gate 2511 has no effect upon the gate 2517. If a SCH4, SCH5, or a TALLY signal has recently been in existence, indicating a search 4, search 5 or tally procedure has just been carried out, these signals will have passed through a gate 2515 and cleared the flip-flop 2516, causing the $\overline{Q}$ output of the flip-flop 2516 to go positive. The output signal from the gate 2511 then passes through the gate 2517 and becomes an inverted RESET TRACK pulse. This pulse resets the track counter so that charge information scanning begins in the first track within the charge information storage area. The trailing edge of the signal from the gate 2511 toggles the flip-flop 2516 and causes it to disable the gate 2517 once more. As mentioned above, ordinarily only one track of the charge information storage area is scanned at a time, and information is stored away serially within that track. After one of the three above-mentioned searches has been performed, the charge information storage area may be scanning the last track within the area. It is therefore necessary to reset the track counter in the above manner and to begin scanning at the first track so that it can be redetermined which track the charge information was previously being stored in. The gate 2517 is disabled by an APC signal during an all patient charge printout to prevent the RESET TRACK signal from interfering with the all patient charges search scanning of the charge information storage area. As will be explained below, charges received during an APC search are stored in an auxiliary track and do not interfere with the operation of an APC search.

The bistable 2512 remains set until a storage location for the new set of charge information is found. Then a CTR EN signal generated by a bistable 2660 clears the bistable 2512. If no location is found before the end of the track currently being scanned, an ETC1 signal is allowed to pass through a gate 2599 and generate an ANT signal, which advances the track counter to the next track. Note that the gate 2599 can allow an ANT signal to be generated only when the bistable 2512 is set. Therefore, the track counter is advanced only when the track currently being scanned is full of data.

The circuitry at the top of FIG. 25 continuously scans the charge information storage area looking for locations containing no data in the 0th character slot. Depending upon whether an all patients charge search is in progress, either data from the main charge information storage area in the form of a DATA C signal, or data from the auxiliary charge information storage area in the form of an AUX DATA signal is passed through one of two gates 2520 or 2521, through a gate 2522, and into a gate 2524. The gate 2524 is disabled except during the bit timing intervals T3 through T6 by a bistable 2523, and it is pusled by PHASE B timing pulses. The gate 2524 is also disabled except during the time when the first character within a storage location is being scanned by a CP00 timing signal. During bit timing interval T1 of character timing interval CP00, a gate 2526 clears a flip-flop 2525. If any data appears at the output of the gate 2522 during bit timing intervals T3 through T5 of character timing interval CP00, the gate 2524 is enabled, and it toggles the flip-flop 2525 into the Q state. This disables the gate 2527 and prevents a T5 timing pulse from passing through the gate 2527 and enabling a gate 2514. When a storage location is found that contains no data in the first character location, the flip-flop 2525 is not toggled, and a T5 pulse is allowed to pass through the gate 2527 and enable the gate 2514. The gate 2514 then generates a SET CUL (set core unload bistable) signal which sets a bistable 2601 shown in the upper left hand portion of FIG. 26 and cause a CUL (core unload) signal to be generated. This signal initiates the process of unloading data from the core and placing it into the location which has just been found.

The CUL signal enables a series of gates 2602 through 2606 to generate signals which control the transfer of data between the core memory and the empty storage location. With the start of the CP00 timing pulse, the gate 2602 generates a signal that enables the gate 2607 to set a bistable 2608 and cause the generation of a CH* signal. This CH* signal is fed to a address register of the core memory 3720, andit causes the address register to advance one position with each character. The output signal from the gate 2602 also enables the gate 2620 to set the address register 3726 to location octal 010 during a T4 timing pulse. This is the location where the first character in the patient number which accompanied the input data is stored. During character counts CP01 through CP12, the patient number is transferred out of the core memory and into the empty storage location. During character count CP13, the core address register is set to the address 001, where the first character in the nursing station or point of the sale number is stored. This number is fed into the charge information storage area during character counts CP14 and CP15. During character count CP15, a gate 2604 and a gate 2602 set the core address register to location 213, which is the first digit of a two-digit department number. During character counts CP 16 through CP33, data is read serially from the core storage area into the empty storage location. This data includes a two-digit department number, an eight-digit item number, the quantity, frequency, or number of items data, and a six-digit price number that includes a decimal point. The decimal point is skipped over in a manner described elsewhere. The gates 2606 and 2603 then set the address register 3726 to location octal 601 where the credit symbol, if any, is stored. This symbol is read into the thirty-fourth character location within the storage location. Character count CP35 then causes the gate 2605 to generate a C RELEASE (core release) signal that resets the bistable 2611, terminates the CH signal, and that initiates a printout of the transaction at the remote stations, as explained in the concurrently filed application. The CH signal, in turn, resets the bistable 2608 and terminates the CH* signal. This completes the process of reading data from the core memory 3720 into a charge information storage location.

The data from the core memory 3720 is translated from parallel into serial form by a gating logic disclosed in the concurrently filed application. The data appears in the form of an SCD (serial core data) signal that is applied to a gate 2531. The gate 2531 normally passes this data to a gate 2532 and on to the magnetic drum in the form of a DWCM signal. The data flow is stopped during character counting periods CP12 and CP34 by a TMN signal that inhibits the gate 2531. This causes blanks to be placed in the two printout marker character slots within the storage location, so that the data is not accidentally marked for printout. The TMN signal is generated by circuitry shown in the lower right hand corner of FIG. 26.

The gate 2531 is normally enabled by the CH signal generated by the bistable 2611, and by the CUL signals generated by the bistable 2601. The CUL signal normally passes through a gate 2530, through a gate 2533, and becomes the MWEC (memory write enable core) signal that causes data to be written upon the drum. During APC operations, the gate 2530 is disabled by the APC signal. The CUL signal then flows through a gate 2540 that is enabled by the APC signal, and enables a gate 2541 to pass core data through a gate 2542 and on to the auxiliary track in the forms of a DWCAX (drum write charge auxiliary track) signal. The output signal from the gate 2540 also enables the gate 2543 in this case to generate an MWAX (memory write auxiliary) signal which enables data to be written onto the auxiliary track. Since data stored on the auxiliary track must belater re-recorded onto the main track, and since one bit of timing interval is lost in this process, it is necessary to have the core data arrive one bit earlier at the gate 2541 than it arrives at the gate 2531. This is done by providing two core data output signals, an SCD signal and an SCDE (serial core data early) signal. The SCDE signal is also generated by circuitry disclosed in the concurrently filed application. A TMX signal disables the gate 2541 and causes blanks to be written into the printout marker character locations.

The TMX and the TMN signals are generated by two flip-flops 2630 and 2631 shown in the lower right hand portion of FIG. 26. The TMX signal begins and ends exactly one bit before the TMN signal begins and ends. A CP12 timin signal ORed together with a CP34 timing signal is applied to the D input of the flip-flop 2630, and is gated into the flip-flop 2630 by a T6 timing pulse. This information is then gated into the flip-flop 2631 by a T7 timing pulse. In this manner, the blanking signals are generated with a one bit difference in timing. The flip-flops 2630 and 2631 are both cleared by the MS (master strobe) signal at the end of each drumrotation.

Once charge data is stored in a charge information storage location, it is necessary to mark the first character slot in the location so that a second set of charge data is not stored in the same location. The CUL signal generated by the bistable 2601 sets a bistable 2660 during a T7 bit timing pulse and enables the gate 2650 to pass CP35 character timing pulses to a counter 2651. The counter was previously held in the clear state by the bistable 2660. The counter 2651 now counts the CP35 pulses until 72 such pulses have been counted. This is the total number of CP35 pulses which occur during a drum revolution, so a 72 count output on the counter 2651 enables a gate 2651 when the drum has just completed one complete revolution and the drum head is ready to scan the same storage location once more. Note that it takes an inverted signal at the input of the gate 2650 to add a count to the counter 2651, so the counter advances at the end of the CP35 timing signal, or at the beginning of a CP00 timing signal. During the T1 bit timing interval of character count CP00, the gate 2652 is enabled to set a bistable 2653 and to generate a MARK signal. This MARK signal is fed into a gate 2544 and a gate 2545, shown in the lower portion of FIG. 25. Depending upon whether the APC signal is present or not, the MARK signal either enables the gates 2533 and 2532 and causes a mark to be placed in the main charge information storage area, or it enables the gates 2543 and 2542, and causes a mark to be placed in the auxiliary storage area. The MARK signal then enables the gate 2670 to reset the bistable 2660 during the T3 timing pulse interval. The bistable 2653 is quickly reset by a T5 timing pulse.

A gate 2501 and a flip-flop 2502 shown toward the center of FIG. 25 are used o generate a CLO signal whenever any one of a number of system operations involving the charge information storage area is in progress. This CLO signal is used to inhibit certain sections of the system from commencing their operations and interfering with a search or a charge storage procedure. The CLO signal is combined with a CASH (cashier) signal by a gate 2503 to form a CLO* signal.

It was mentioned above that the XI signal generated by a gate 2513 is used to prevent any searches from being initiated by the bed information storage logic during the storage of charge information in the charge information storage area. This XI function signal is also used for other purposes during an APC (all patient charges) search, as will be explained below. The flip-flops 2514 and 2515 normally are kept in the $\bar{Q}$ state by th absence of the APC signal, and thus keep the gate 2513 enabled.

At the beginning of the APC mode of operation, the auxiliary track is erased by circuitry shown at the bottom of FIG. 25. The APC signal and the MS (master strobe) signal cause the gate 2550 to set a bistable 2551. The output signal from the bistable 2551 is applied to the gate 2543 and causes blank data to be written upon the auxiliary track. Any convenient timing signal, in this case a CP12 plus CP34 timing signal, is used to enable the gate 2552 and allow the signal generated by the bistable 2551 to set a second bistable 2553. The bistable 2553 then disables the input gate 2550 and prevents the erasure process from continuing for more than one revolution. The ETC2 (end of track) signal resets the bistable 2551 at the end of the track and terminates the erasure process. When the APC search is complete, the APC signal resets the bistable 2553.

PRINTOUT MARKER DETECTOR AND BUFFER TRACK CONTROL FOR THE CHARGE INFORMATION STORAGE AREA

Figure 7:
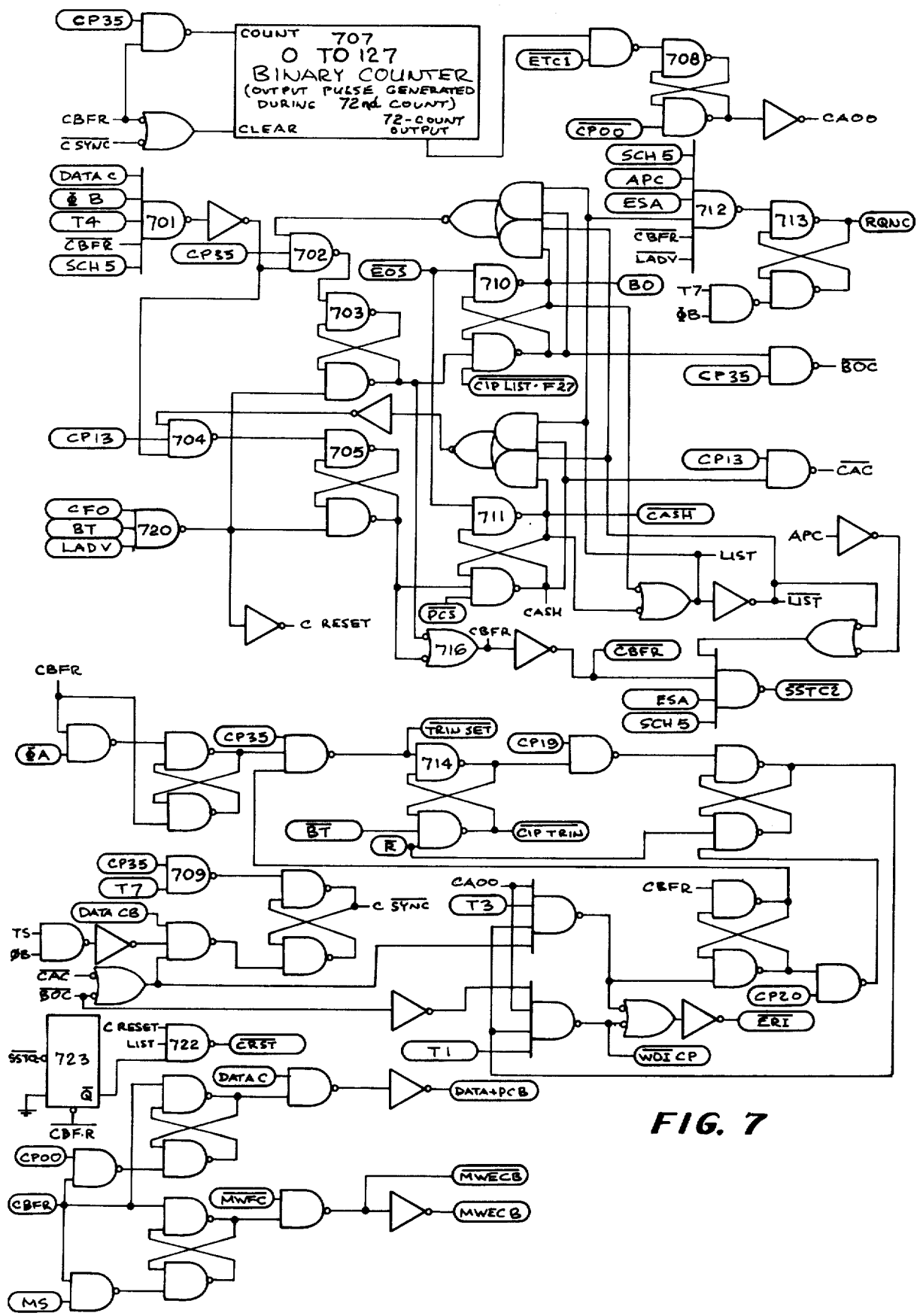
FIG. 7 is a logic diagram of the printout marker detector and buffer track control for the charge information storage area.

FIG. 7 is a logic diagram of the printout marker detector circuitry and the charge buffer track, control circuitry for the charge information storage area. This circuitry is almost identical to the circuitry disclosed in FIGS. 3 and 4 used to detect printout markers in the bed information storage area, and will not be explained again in detail. Unlike the bed information storage area printout marker search, the search for printout markers in the charge information storage area is carried out only when a SCH5 signal is present. This signal enables a gate 701 to sift through the data in the charge information storage area and look for printed markers. The printout markers can be in either of two character slots. Printout markers in the slot corresponding to CP35 indicate an item in a business office list. Such markers are detected by a gate 702 which sets a bistable 703. Printout markers in the slot corresponding to CP13 indicate an item in a patient charge search. Such markers are detected by a gate 704 which sets a bistable 705. When either of the bistables 703 and 705 is set, the gate 716 generates a CBFR (charge information buffer track) signal which initiates a transfer of the contents of the marked location from the main track onto the buffer track. This transfer is accomplished in exactly the same manner as such transfers were carried out between the main bed information storage area and the bed information buffer track, and will not be described again at this point. The counter 707, with the help of a CP00 signal and a bistable 708, generates a CA00 signal which functions in exactly the same manner as the A00 signal generated within the bed information storage area. Since the counter 707 does not automatically reset at the end of 72 counts, a synchronizing circuit is included which is exactly analogous to the synchronizing circuit used in the bed information printout logic. Printout markers in the charge information storage area are erased in exactly the same manner that printout markers were erased in the bed storage area. In the case of an APC search, a special character is written into the printout marker storage area is exactly the same manner as special characters were written into analogous printout marker areas within the bed information storage areas during APC searches.

There are several differences between the logic diagram of FIG. 7 and that of FIGS. 3 and 4. First, the two bistables 710 and 711 can be set by external signals as well as by the bistables 703 and 705. The inverted CIP LIST signal, ANDed together with an F27 bed printout format timing signal, can set the bistable 710. Similarly, an inverted PCS signal can set the bistable 711. Thus, the search circuitry of FIG. 5 can be set up prior to the discovery of a marker bit in the manner specified. When a CIP LIST printout is initiated, the bistable 710 is set up immediately after printout of a patient number is complete so that no PCS information will separate this number from the list of charge allocable to that patient. Similarly, when a PCS (patient charge search) is initiated, the bistable 711 prevents the recognition of business office printout markers.

Another difference between FIG. 7 and FIGS. 3 and 4 is the gate 712 and th bistable 713. The gate 712 is enabled at the end of the last track of an APC search when a printout marker has not been encountered. It sets a bistable 713 and generates an RQNC signal. The RQNC signal is sent back to the APC control logic and is used to initiate a search of the bed information storage area for a new patient number The generation and use of this signal will be explained more fully below.

A bistable 714 generates a signal to inhibit the advance of the charge information storage area track counter while a printout marker is erased. This signal is called the CIP TRIN signal. It performs exactly the same function as the analogous TRIN signal generated in FIG. 4.

In place of the STC 1 signal generated in FIG. 4, the logic in FIG. 7 generates an SSTC 2 signal. This signal is initiated by an ESA (end of the last track) signal when the CBFR and LIST signals have terminated. This signal is also generated by the APC signal even though the LIST signal is still present. The signal is not fed directly to the time and date circuitry but is fed to the logic circuitry at the bottom of FIG. 6, where it is channeled by a switching gate 601 either to the calandar circuit in the form of an STC signal, or to the logic circuitry of FIG. 5 in the form of an EOSS signal. If an APC search is in progress, the gate 601 will generate a negative potential and will rotate the SSTC 2 signal out through the gate 603 as the EOSS signal. If a tally is initiated during an APC search, the TAL signal locks the flip-flop 602 in the $\overline{Q}$ state and causes the SSTC signal to add a time and date line to the tally search results printout.

The STC signal goes to the time and date calendar circuit in the form of an STC2 signal generated by a gate 699. Other input signals to the gate 699 include a TOT COMP signal which causes a time and date line to be added to a printout of the day's total charges, credits, and payments on account, and a HLT1 signal which has been ANDed together with a T2 timing signal. This latter signal initiates a time and date printout at the end of one part of the APC (all patient charges) printout.

The bistables 703 and 705 are reset by a C RESET signal generated by a gate 720. This signal is generated when the BT signal indicates that the track counter is at the beginning of the track, when the CF0 signal is positive indicating that the charge printout format counter is at CF0 count, and when the LADV signal is not present, indicating that the time and date calendar circuit is not occupied with some other part of the system.

The C RESET signal is passed through a gate 722 along with the LIST signal and becomes a CRST signal. This CRST signal can be suppressed by the SSTC2 signal, which toggles a flip-flop 723 and disables the gate 722, but usually the CBFR signal clears the flip-flop 723. The CRST signal normally sets a bistable 3140 (FIG. 31). When the CRST signal stops, indicating the printout is complete, the bistable 3140 enables a gate 3141 to set a bistable 3142 and start a new search of the charge information storage area for more printout markers. The bistable 3142 sets a bistable 3144 that generates the SCH5 signal. This signal, it will be remembered, enables searches for printout markers to be carried out in the charge information storage area. Thus, once a printout marker search is begun, the search continues until all markers have been found. When a complete search of the charge information storage area does not locate any new printout markers, the CBFR signal does not clear the flip-flop 723, and the gate 723 is never enabled to generate a CRST signal. The search for printout markers then terminates. During an APC search, the LADV signal then is generated to tell the APC logic that all charges marked have been printed out.

LIST OUTPUT CONTROL

Figure 5:
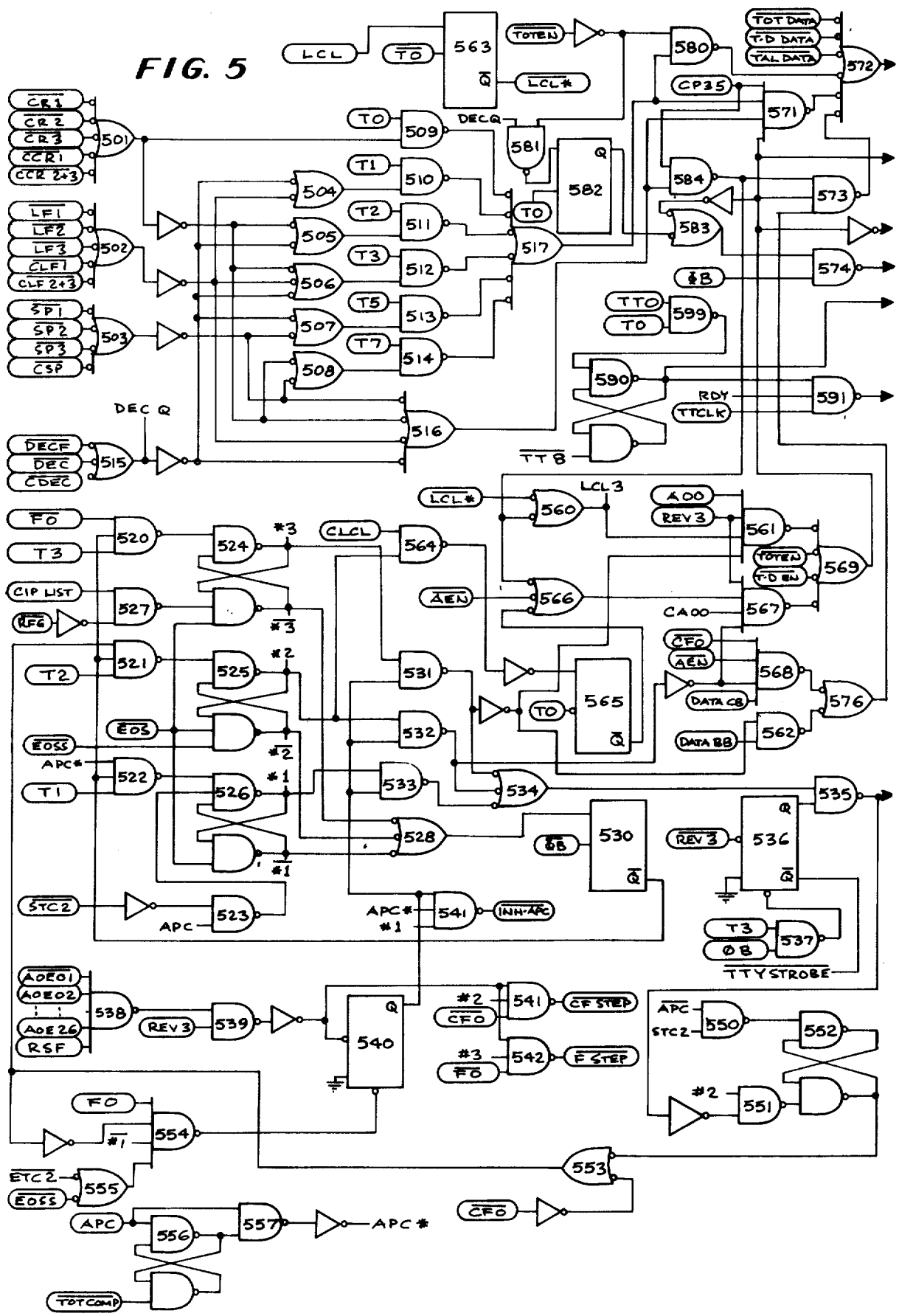
FIGS. 5-6 form a logic diagram of the list output control.
Figure 6:
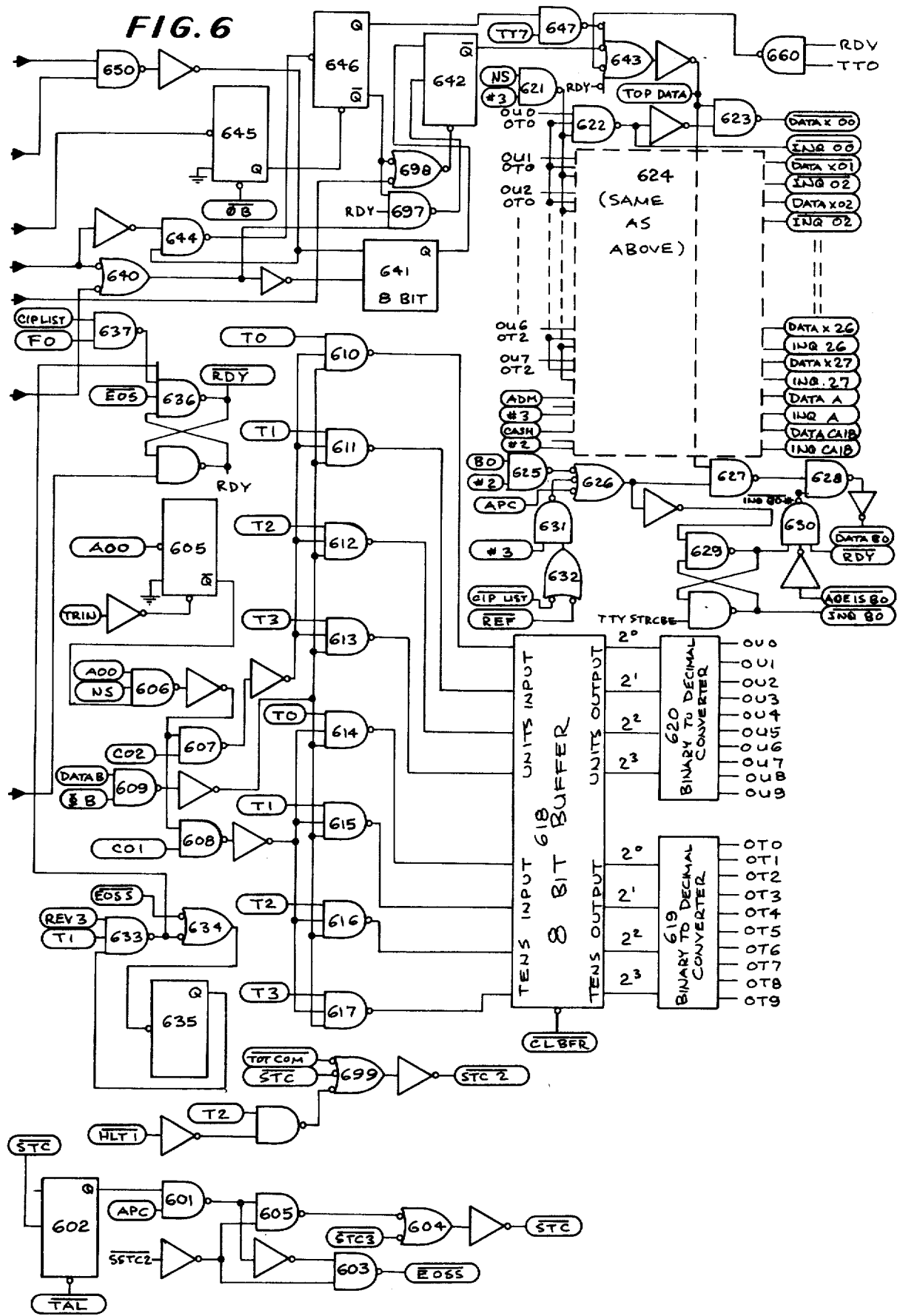

FIGS. 5 and 6 are logic diagrams of the circuitry used to control the outputting of lists to the various remote stations. FIG. 5 and the upper half portion of FIG. 6 both deal with the compilation, formating, and assembly of output data messages. The resulting output signal is the TOP DATA signal generated by a gate 643 located in the upper right hand corner of FIG. 6. The central portions of FIG. 6 address the messages to the remote stations and also interrogate the remote stations to find out if they are busy with other messages.

The three primary sources of data for list printouts are the buffer track of the bed information storage area, the buffer track of the charge information storage area, and the core memory. When information is to be read off the buffer track of the bed information storage area, an F0 signal generated by the bed information printout format generator is terminated. This signal, and a T3 timing signal, enable a gate 520 to set a bistable 524, generating a *3 signal. The *3 signal initiates a printout of data from the bed information storage area buffer track. When the information is to be read off the buffer track of the charge information storage area a CF0 signal generated by the charge information printout format generator is terminated, enabling a gate 553 to enable a gate 521 along with a T2 timing signal. The gate 521 then sets a bistable 525 and causes the bistable to generate a *2 signal. This *2 signal initiates a printout of information from the charge information storage area buffer track. When the days total charges, credits, and payments on account are to be printed out, the APC signal and the output signal from a bistable 556 enable a gate 557 to generate an APC* signal. This signal, along with a T1 timing pulse, enables a gate 522 to set a bistable 526. The bistable 526 generates a *1 signal, which initiates a printout of the days total data which is stored in the core memory. When this data has been completely printed out, a TOT COMP signal resets the bistable 556, and terminates the APC* signal.

If any of the three bistable 524 to 526 is set, a gate 528 toggles a flip-flop 530 into the Q̄ state. The flip-flop 530 disables the three gates 520 to 522 and prevents two or more list printouts from occurring simultaneously.

The * signals initiate an inquiry as to the availability of the remote station to which the list is addressed, using circuitry shown in the upper right hand portion of FIG. 6. The *3 signal, and the NS signal generated by the bed information storage area printout marker detection circuitry, enable a gate 621 to initiate an inquiry as to the availability of the teleprinter in a particular remote station. The *3 signal also enables a gate 631 to initiate an inquiry as to the availability of the business office teleprinter when a patient charges or a reference list is being processed. The CIP LIST signal and the REF signal are combined in a gate 632 and are also fed into the gate 631. The *2 signal can initiate an inquiry either to the cashier's office or to the business office. The business office inquiry is made by a gate 625, while the cashier's office inquiry is made by a gate at the bottom of the logic circuitry 624. An admissions office inquiry in response to a *3 signal is also handled by a gate within the logic circuitry 624.

In the case of information which is to be transmitted to a nursing station from the bed information storage area, it is necessary to determine which nursing station the information is to be sent to. In every case, the information is sent to the nursing station that includes the bed which the information relates to. The number of this nursing station is stored in the first and second character slots within the bed information storage location containing the data to be printed out. The circuitry in the center of FIG. 6 scans the data on the buffer track, obtains this nursing station number from the data, and generates appropriate signals for initiating the transmission of the data to the nursing station.

The process of searching for the nursing station number is initiated by a gate 606 which is under the control of a flip-flop 605. The inquiry is initiated by the TRIN (track counter advance inhibit) signal, which clears the flip-flop 605 and partially enables the gate 606. The NS (nursing station) signal and the A00 information location signal complete the task of enabling the gate 606. The trailing edge of the A00 signal then toggles the flip-flop 605 into the Q state and permanently disables the gate 606, thus preventing the gate 606 from acting a second time. The output signal from the gate 606 enables a gate 607 to pass a C02 timing signal to the four gates 610 to 613, and also enables a gate 608 to pass a C01 timing signal to the four gates 614 to 617. The individual gates 610 through 617 are then enabled to T0 to T3 timing signals to sample the data flowing from the buffer track (DATA B signal) and presented by a gate 609 during the two character timing intervals C01 and C02. In this manner, the nursing station number is transmitted from the buffer track into an 8 bit buffer storage 618. The buffer 618 comprises eight bistables having a common clear line. The buffer 618 is eventually cleared by a CLBFR (clear buffer) signal generated by the bed information control logic gate 384. The output of the buffer 618 is translated by two binary-to-decimal convertors 619 and 620 into two sets of ten signals. One set of ten signals represents the units digit in the nursing station number, and the other set of ten signals represents the tens digit of the nursing station number. In each set of ten, only one signal is ever energized at one time. These signals are used to selectively enable the pair of gate 622 and 623, and an array of identical pairs of gates 624. These signals, together with the signal generated by the gate 621, enable only one pair of gates within the array, and thereby determine the nursing station to which the printout is routed. The enable pair of gates generates an INQ (inquiry) signal which is transmitted to the remote station. When the teleprinter at the remote station is available, an AOE signal is generated by the remote station and is transmitted back to a gate 538 shown in the lower left hand corner of FIG. 5. The signal generated by the gate 538 is then timed to coincide with REV3 by a gate 539, and is used to toggle a flip-flop 540 into the Q state. The flip-flop 540 then generates a signal which enables the three gates 531 to 533 and allows the generation of the output message to commence. Inquiries to places such as the admitting office, the cashier's office and the business office are handled in a similar manner, except addressing signals are not needed. These signals also result in AOE signals which are transmitted back to the gate 538 in the manner described above. The inquiry circuits for admitting office and cashier's office are identical to those for the nursing stations, and are included within the block 624. The business office inquiry circuitry is somewhat different, and is shown below the block 624. A gate 626, having three inputs, is required because the business office must be able to receive four different types of lists, as shown. The inquiry signal is generated by a bistable 629 which partially enables a gate 630 at the same time it generates an inquiry signal. TTY STROBE signals generated by the flip-flop 536 at the start of every third revolution of the drum attempt to reset the bistable 629, and can actually rest the bistable 629 if the source of the inquiry is terminated. This controls the exact time when an inquiry is terminated and maintains the INQB0 signal even during short discontinuances in an INQB0* signal generated by the gate 626. The output signal generated by the bistable 629 is combined with the AOE 15 B0 (answer to inquiry from the business office) signal. When both of these signals are positive, a gate 630 inhibits the flow of data through a gate 628 to the business office until a RDY signal is generated by a bistable 636, when the message is ready for transmission.

Once it has been determined that the teleprinter is available at the location to which a message is addressed, the process of transmitting information to the remote teleprinter can begin. The enabled gate 531, 532, or 533 transmits a signal through the gate 534 and enables the gate 535 to pass a TTY STROBE (teleprinter strobe) pulse to the bistable 636, causing the bistable to generate the RDY (ready) signal. This RDY signal enables a gate 643, and thus allows data to flow to the selected remote station teleprinter. If data is to be transmitted to a nursing station, the INQ signal enables the output gate corresponding to the gate 623 through which the data flows on its way to the remote station. In the case of a business office, the INQB0* signal enables the gate 627, and the RDY signal causes the gate 630 to enable the gate 628. In this manner, a data path is established from the gate 643 to the chosen remote teleprinter. A gate 660 is also enabled by the RDY signal. This gate passes a TT0 timing signal. This TT0 timing signal is the teleprinter start signal, and is transmitted to the remote teleprinter at the start of each character.

The data from the various sources flows into a data collection gate 572, through a gate 650, and into an eight-bit shift register 641. The data then flows through the flip-flop 642, which is connected in shift register manner to the output of the shift register 641, through the gate 643, and on to the remotely located teleprinter. Data is clocked into the 8 bit shift register 641 by PHASE B timing pulses under the control of a gate 574. The PHASE B timing pulses pass through a gate 640 to the shift pulse input of the shift register 641. As information is shifted into the shift register 641, it is also gated by the same PHASE B timing pulses through a gate 644 to the clock terminal of a flip-flop 646. A pulse is applied to the clock terminal of the flip-flop 646 for each "1" data bit included in the data that enters the shift register 641. The ultimate state of the flip-flop 646 is therefore $\overline{Q}$ if the parity of the information is even, and Q if the parity of the information is odd. Thus, the flip-flop 646 performs an automatic parity check on the data flowing into the shift register 641. If the parity is even and proper, the flip-flop 646 does not interfere with the flow of data out of the shift register 641 through the flip-flop 642 and into the gate 643. If a parity of the data is odd and improper, the flip-flop 646 causes the gate 698 to disable the flip-flop 642 by locking the flip-flop 642 in the $\overline{Q}$ state. The flip-flop 646 then enables a gate 647 to apply a TT7 teleprinter timing pulse to the gate 643. This pulse, together with the TT0 pulse passed by the gate 660, causes the teleprinter code for a question mark to be transmitted to the data output terminal. Thus, characters which do not pass a parity check are replaced by a question mark in the printed output. This gives printed indication of the parity mismatch, but does not interfere with the transmission of data. The flip-flop 646 is initially cleared by the flip-flop 645 just before information data is read into the shift register 641.

Data is shifted out of the shift register 641 and through the flip-flop 642 at the teleprinter timing signal rate of speed. This process is controlled by a bistable 590 which is set at the beginning of the first teleprinter character TT0 by a gate 599. The bistable 590 causes the gate 698 to release the clear terminal of the flip-flop 642, and also enables the gate 591 to pass TTCLK (teleprinter timing clock pulses) through the gate 640 to the shift register 641, and also through the gate 697 to the flip-flop 642. The TTCLK pulses then advance the data out of the 8-bit shift register 641, through the flip-flop 642, and through the gate 643.

The data transmission process is usually terminated by an EOS signal generated by the time and date calendar circuitry after the time and date have been printed out at the end of each message. The EOS signal resets the bistable 636 and also the bistables 524, 525, or 526. During an all patient charges (APC) printout, the EOSS signal is used to terminate a printout, because the time and date is not printed after each entry. This signal is applied to a gate 634 and toggles a flip-flop 635. The flip-flop 645 enables a gate 633 to generate an output pulse at the beginning of the third drum revolution (REV 3). This pulse is then used to reset the bistable 636. The EOSS signal is also used directly to clear the bistable 525. In the case of a new in-patient number printout during APC, printout is terminated by a gate 637 in response to the CIP LIST signal and the F0 signal. The latter signal indicates that the bed information printout format generator has finished formating the output message and is standing by for another message. The CIP LIST signal also enables a gate 527 so that an RFG signal can reset the bistable 524 at the end of such a printout. The RFG signal is generated by the bed information printout format generator simultaneously with the F0 signal, but is of short duration and does not interfere with the resetting of the bistable 524 at a later time.

List data is collected by a gate 572 and is then fed through the gate 650 and into the shift register 641. There are basically six sources of data which are all fed into the gate 572. The first is the TOT DATA (Totals Data) signal. This data signal is derived directly from the core memory when the totals of all charges, credits, and payments on account are printed out. The second data signal is the TD DATA (time and date data) signal. This signal is generated by the time and date calendar circuitry. The third data signal is the TAL DATA (tally data) signal. This signal is generated by the tally search control logic. It carries the number of items found in a tally search. The fourth data signal is the special character data signal. This includes carriage return characters, line feed characters, space characters and decimal point characters. The last two data signals come from the two buffer tracks on the magnetic drum. The data (DATA BB) from the bed information storage area buffer track comes through a gate 562 which is enabled during any *3 search by the gate 531. This data flows through the gates 576 and 573, and into the gate 572. The data (DATA CB) from the charge information buffer storage track comes through a gate 568, which is enabled during any *2 search by the gate 532. This data signal flows through the gates 568, 576 and 573, and into the gate 572.

The special characters are generated by the circuitry shown in the upper left hand corner of FIG. 5. Any one of the five signals fed into a gate 501 will cause a carriage return character to be generated at the output of the gate 517. Any one of the five signals fed into the gate 502 will cause a line feed character to be generated at the output of the gate 517. Any one of the four signals fed into the gate 503 will cause a space code character to be generated at the output of the gate 517. Any one of the three signals fed into the gate 515 will cause a decimal point character to be generated at the output of the gate 517. Gates 504 through 508 couple the input gates 501 to 503 and 515 to appropriate timing gates 509 to 514 which pass the necessary T timing signals to form the desired characters. For example, the gate 501 is connected directly to the gate 509, the gate 511, and the gate 512. Thus, the character generated at the output of the gate 517 will include "1" bits in the timing positions T0, T2, and T3. This produces the teleprinter code for a carriage return character at the output of the gate 517. The output signals from the gate 517 are usually fed into the gate 572 through the gate 571 during the character count CP 35. The gate 571 is enabled whenever a special character is being generated by a gate 516. The gate 516 collects signals from all the gates 501 to 503 and 515, and generates a signal whenever a special character is requested. The final enabling signal for the gate 571 is generated by the gate 569, as will be explained below.

The process of loading data into the 8-bit shift register 641 is initiated by a signal generated by a gate 569. This signal passes through the gate 583 and enables the gate 574 to pass PHASE B timing pulses through the gate 640 and on to the clock terminal of the shift register 641. Thus, it is necessary for this signal to be positive when data is to be read into the shift register 641. Data is read into the shift register 641 during REV 3, the third revolution of the drum. During revolutions 1 and 2, the data is fed to the teleprinter. In the typical case of a printout from one of the buffer tracks in one of the drum storage areas, data is continually transmitted to one or the other of the gates 562 or 568 and out through the gate 576. It is necessary to enable the gate 569 only during the brief interval when the desired signal character is being presented to the gate 562 or 568. As discussed more fully above, the time when the storage location containing the desired data appears at the gate 572 is indicated by the A00 and the CA00 signals. The A00 signal appears when the desired storage location on the bed information buffer track is scanned, and the CA00 signal is generated when the desired storage location on the charge information buffer track is scanned. These signals are used to partially enable the two gates 561 and 567 at the proper times. The outputs of these two gates, when fully enabled, cause the gate 569 to generate a signal that loads the eight bit shift register 641.

The A00 and the CA00 signals determine which storage location data is retrieved from, but they do not determine which individual character within the location is loaded into the shift register 641. This task is carried out by format generating logic circuits which will be described in more detail below. The bed information printout format generator logic generates an LCL signal which passes through a flip-flop 563, a gate 560 and into the gate 561. The gate 561 is partially enabled by the gate 531 whenever a *3 printout is in progress, and is also partially enabled by the A00 signal. The gate 561 is completely enabled only during the time when a particular individual character, as indicated by the LCL signal, within a particular storage location, as indicated by the A00 signal, is being fed into the gate 573, and only during REV 3. The output signal from the gate 569 thus only enables the gates 573 and 574 long enough to load one character into the shift register 641.

The flow of data from the charge information storage area is controlled in an identical manner, as shown in FIG. 5, during a *2 printout. The particular character is determined by the CLCL format signal, the particular location in the buffer track is determined by the CA00 signal, and the process is again allowed to occur only during REV 3.

Whenever a special character is to be generated, the gate 516 generates a signal that enables the gate 571 to pass data from the gate 517. Signals from the format generators are fed into the gates 501, 502, 503, and 515 whenever it is desired to add a special character to those retrieved from the buffer track storage areas. The gate 517 repeatedly generates the special character desired, and the special character is fed into the gate 571 arbitrarily during character count signal CP35. The A00 and the CA00 signals are still operative, and these signals determine the exact time when a special character is loaded into the shift register 641. During the periods when special characters are generated, the LCL and the CLCL signals are absent, so some special means is needed to enable the gates 561 and 567. This means is provided by a gate 584, which generates a pulse whenever a special character is fed out of the gate 517 and through the gate 571. This pulse is fed through the two gates 560 and 566 and is used to partially enable the gates 561 and 567 during CP35, just as the LCL and CLCL signals partially enables these gates. To insure that no data flows from the buffer tracks during such a period, the output of the gate 584 is also used to disable the usual data path through the gate 573.

Tally printouts are partly read directly into the gate 572 and are partly extracted from the charge information buffer storage track in accordance with the usual *2 list printout procedure. Those parts of the tally printout which come from the buffer are printed out in exactly the manner described above, under the control of the charge information printout format generating logic. When numerical results of a tally search are to be read out, an AEN signal is generated. This signal disables the gate 568 and prevents the flow of data from the buffer track, and also passes through the gate 566 and enables the gate 567 to allow the passage of data into the shift register 641 during the CA00 time interval. The tally numerical data is then repeatedly presented to the gate 572. During the time interval when the CA00 signal is present, the tally data is read into the shift register 641. The AEN signal is of only one character duration, and therefore it determines the exact time within the CA00 time interval when the tally data is read into the shift register 641.

The logic circuitry which generates the time and date data and the totals data signals also generate their own enabling signals. These enabling signals are fed directly into the gate 569 to enable a passage of data into the shift register 641. When the T-D DATA (time and date data) signal is presented to the gate 572, a T-D EN signal causes the gate 569 to read this data signal into the shift register 646. When the TOT DATA (totals data) signal is presented to the gate 572, a TOTEN signal causes the gate 569 to read this data signal into the shift register 641. the TOTEN signal also partially enables the two gates 580 and 581. This is done so that decimal points may be added to the totals printout. When a decimal point is required, a DECF signal is generated by a counter 2850 (FIG. 28). This signal enables the gate 515 and causes the code for a decimal point to be repeatedly generated at the output of the gate 517. Since the total enable TOTEN signal is not synchronized with the CP character timing signals, but is rather synchronized with the C character timing signals, the gate 571 cannot be depended upon as a passageway for the decimal point to flow through. Therefore, the decimal point signal flows through the gate 580 on its way to the gate 572. In the meantime, the gate 581 causes the flip-flop 582 to pass a signal through the gate 583 to enable the gate 574 and to insure that PHASE B timing signals will be present to read the decimal point signal into the shift register 641.

The flip-flops 563, 582, and 565 are needed to insure that the signals arrive at their destinations at exactly the right time so as not to cut off bits from other signals and so as not to add extraneous bits to other signals.

The totals printout is a *1 printout, initiated by the APC* signal.

The gate 550 and the bistable 552 provide an alternate way of initiating a *2 list printout. The gate 550 is enabled by an STC2 signal which is generated by the gate 669 shown at the bottom of FIG. 6. The gate 550 cannot be enabled during an APC operation. When the gate 550 is enabled, it sets the bistable 552. The output signal from the bistable 552 passes through the gate 553 and enables the gate 521 to pass a T2 timing signal to the bistable 525 to initiate a *2 search. The bistable 551 is then reset by an output signal generated by the gate 535 when the printout is finally commenced. This output signal is combined with a *2 signal in the gate 551 to insure that the bistable 552 is not reset in response to a *3 or a *1 search.

Figure 13:
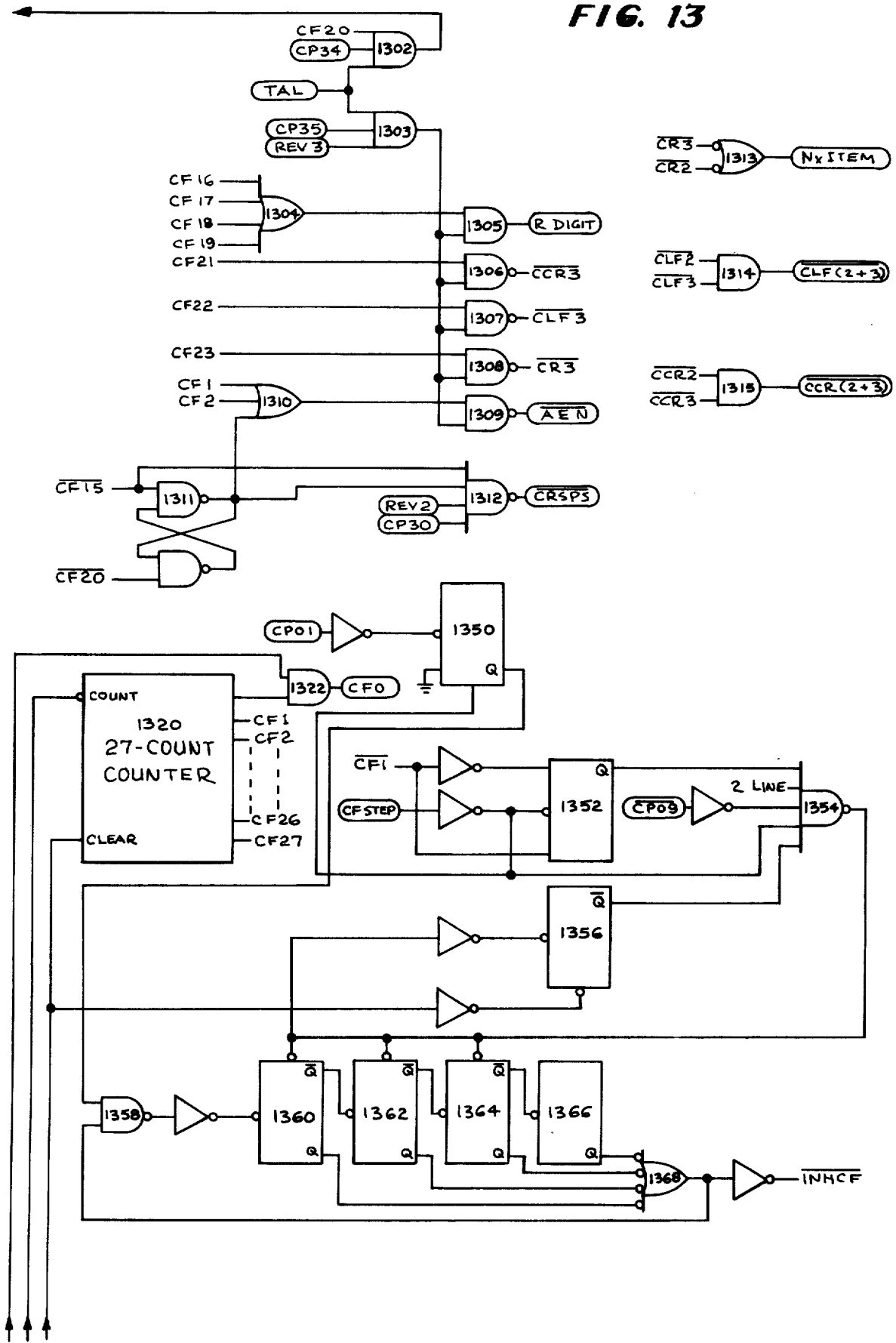

During the outputting of the list information, REV3 timing signals pass through the gate 539 and through one of the two gates 541 and 542. The gate 541 is enabled whenever *2 list is being printed out, as indicated by the absence of a CF0 signal (the CF0 signal is generated by a gate 1322 shown in FIG. 13). Thus, during a *2 search, REV3 pulses pass through the gates 539 and 541 and become the CF STEP signal. This signal is used to advance the counter 1320 (FIG. 13). Similarly, during a *3 search, when the F0 signal (generated by a gate 822 shown in FIG. 8) is absent, the gate 542 is enabled, and the REV 3 pulses become the F STEP signal which is used to advance the counter 821 (FIG. 8). The functions of these counters will be explained below in the sections describing the circuitry of the format generators. When a list printout is completed, a gate 554 clears the flip-flop 540 and disables the gates 531 to 533 and 541. The gate 554 is enabled when both the F0 and CF0 signals are present, indicating the format generators have finished their tasks, when the *1 signal is absent, when the bistable 552 is cleared, and when either an ETC2 timing signal or the EOSS signal is present.

BED INFORMATION PRINTOUT FORMAT GENERATOR

FIGS. 8 through 11 show the circuitry used to generate the LCL signal, which determines the order in which characters are read out of the bed information buffer storage area. Various format signals are generated in the various figures and are collected by a gate 1020 and fed through a gate 1021 to form the LCL signal. The gate 1021 is enabled whenever a *3 (bed information printout) signal is present.

FIG. 11 at the top shows the circuitry which is used to control the format generating process. The BFR signal, which is normally absent, normally maintains bistables 1102 and 1104 in the clear state, and normally disables the gate 1101. The BFR signal is initiated when data is to be fed out of the bed information buffer storage track. It then enables the gate 1101 and allows a C47 timing pulse to set the bistable 1102. The bistable 1102 then generates a BFI signal which inhibits gate B22 at the F0 signal output of a counter 821 (FIG. 8). This terminates the F0 signal. The termination of the F0 signal is used by other sections of the system as an indication of when a bed information printout is ready to begin. The bistable 1102 also enables a gate 1103 and allows a C01 timing pulse to set the bistable 1104. The bistable 1104 disables the gate 1101 and prevents any more C47 timing pulses from setting the bistable 1102. Nothing else happens until F STEP pulses begin to come from the circuitry of the FIG. 5, as explained above. These F STEP pulses are REV 3 timing pulses, and one occurs during each third revolution of the drum. This corresponds to the time it takes to transmit one complete teleprinter character to an output unit. The F STEP signal causes the outputs of the counter 821 to be energized sequentially — first the F1 output, then the F2 output, and so on. The F count thus advances with each three revolutions of the drum.

The particular printout format is determined by control signals generated by circuitry described above. In the case of a nursing station or admitting office printout, the circuitry of FIG. 3 generates an NS or an ADM signal which controls the output format. An NS or an ADM signal passes through a gate 820 and partially enables the gates 812 through 815, and also the gate 817. This connects the circuitry of FIG. 8 to the LCL signal generated by the gate 1021. As the F count advances, the gates 801 through 811 sequentially allow the different character timing signals to enter and to become a part of the LCL signal. During the first three revolutions of the drum, the gate 801 is enabled by the F1 signal to feed C01 timing signals into the LCL signal. During the next three revolutions of the drum, the gate 802 is enabled to feed C02 timing signals into the LCL signal. These signals are used in the manner described above to determine exactly which character is printed out during each set of three drum revolutions. The gates 801 to 807 cause the nursing station number and bed number to be printed out. Then the gate 814 causes a space character to be formed. The gates 808 to 811 then cause the bed status information to be printed out. Finally, the gates 812 and 813 generate carriage return and line feed signals. The gate 815 then generates an R1 signal and sets the bistable 1105 in FIG. 11. The bistable 1105 enables the gate 1106 to form an RFG pulse during the first C01 character timing signal to occur during REV 3 (the third drum revolution). A C47 character timing signal then resets the bistable 1105. The bistable 1105 resets the bistable 1102, terminating the BFI signal and allowing the gate 822 to generate an F0 signal again. The F0 signal is used as an indication that the printout of data is finished.

Figure 9:
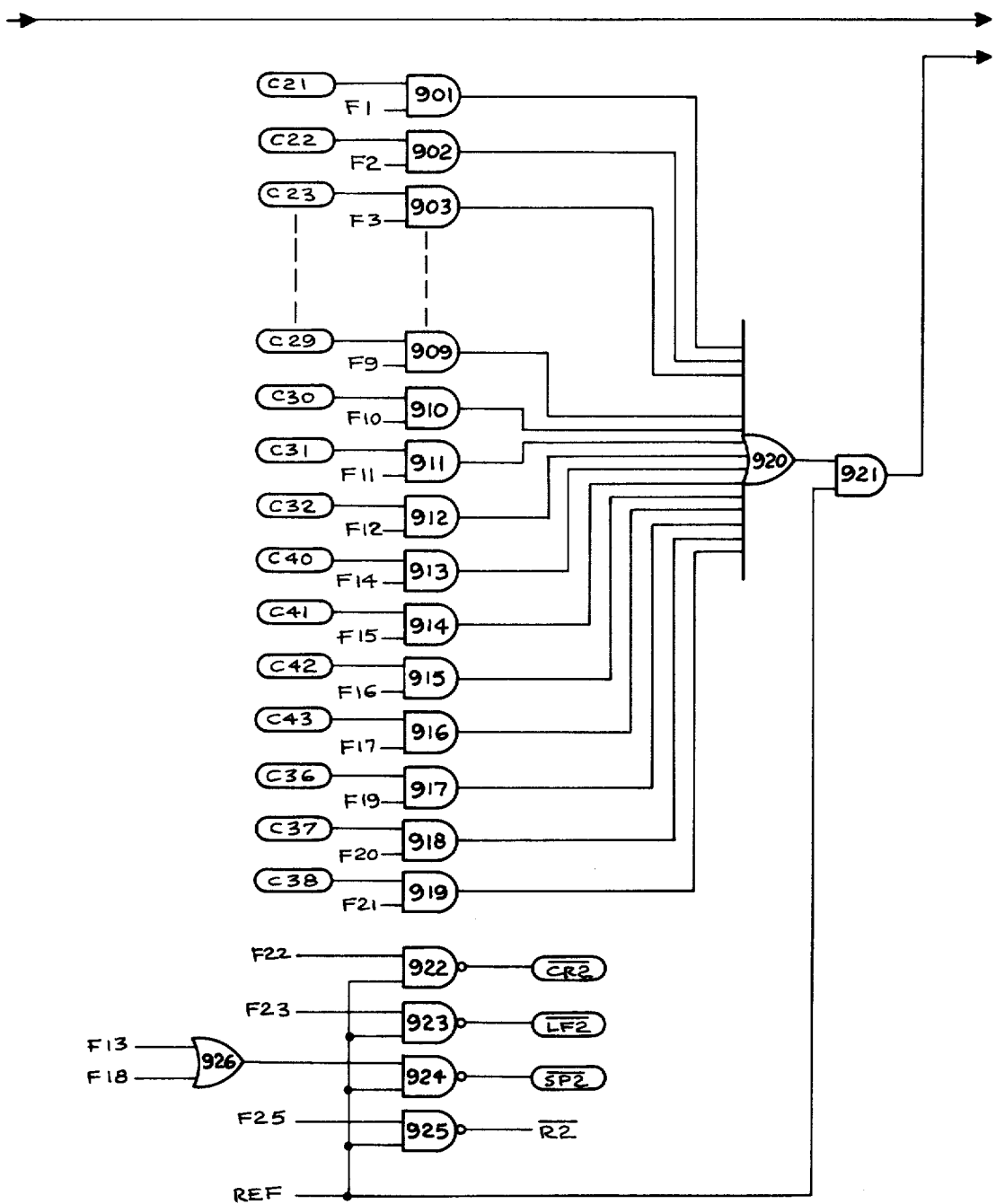

When a reference number search is requested, the circuitry of FIG. 9 is enabled by an REF signal. This circuitry functions in the same manner as the circuitry shown in FIG. 8. It causes the patient case number, the reference number or date, and the doctor number to be printed out.

Figure 10:
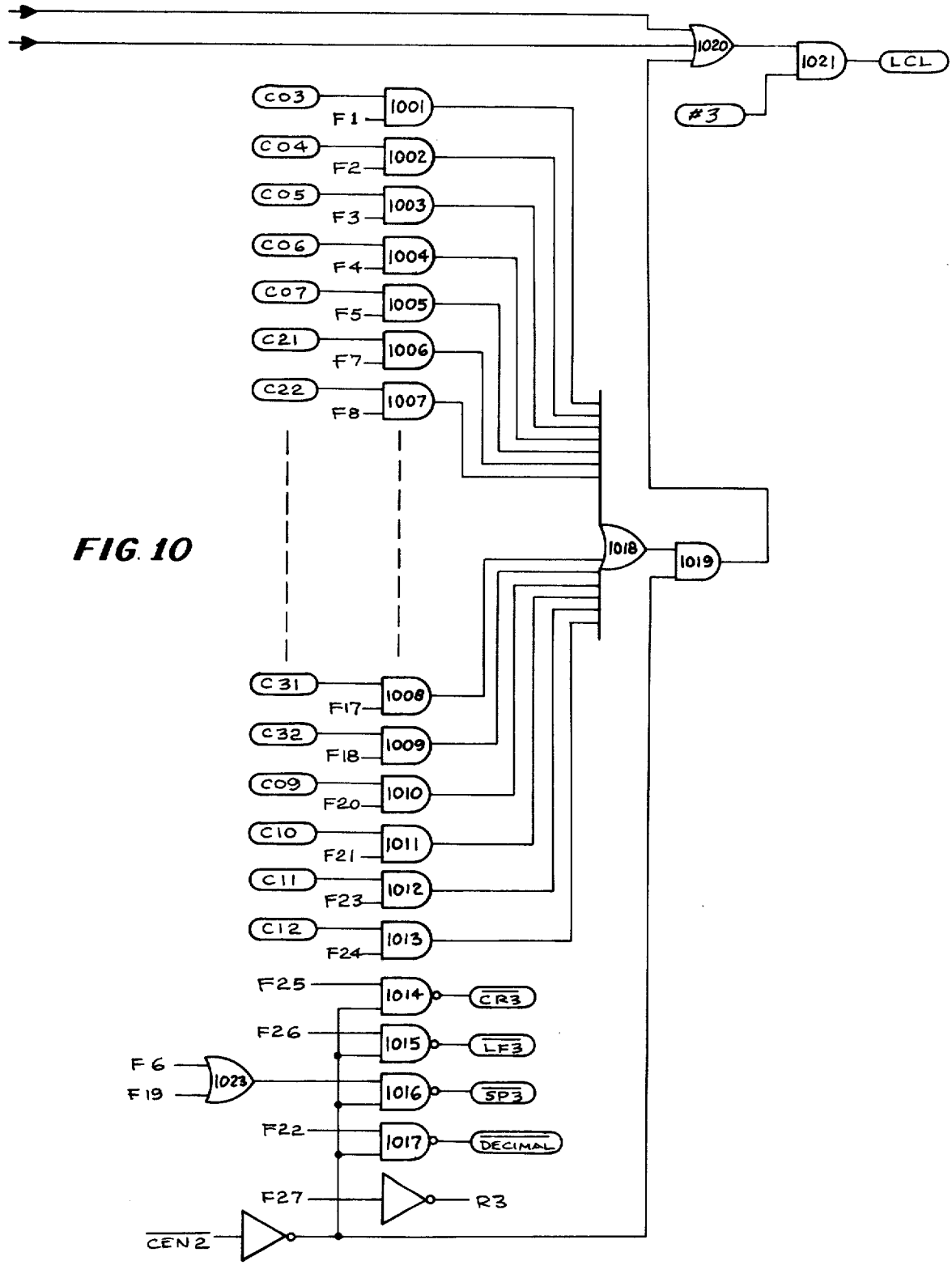

In the case of a CIP bed information printout, part of the circuitry of FIG. 8 is used, and the circuitry of FIG. 10 is also used. The particular part of the circuitry which is used at any given time is determined by the circuitry shown at the bottom of FIG. 11. The CIP LIST signal enables a gate 1107 and allows a REV 3 timing signal to be counted by a four count counter comprising the flip-flops 1108, 1109, and 1110. These flip-flops are enabled by the F1 signal when the counter 821 first begins to advance. When the count reaches four, the four count counter enables the gate 1111 to pass a C01 character timing pulse and to toggle a flip-flop 1112. The flip-flop 1112 initially is in the clear state, because its clear terminal is connected to the BFR signal. When the flip-flop 1112 is toggled, it terminates the generation of a CEN1 signal, and causes a CEN2 signal to be generated. The output pulse from the gate 111 also passes through the gate 1115 and becomes part of the R4 signal which clears the counter 821.

This circuitry functions in the following manner. At the beginning of a CIP printout, a CEN1 signal is generated. This signal passes through a gate 820 and enables the outputting circuitry of FIG. 8. The output then proceeds in the same manner as in the case of a nursing station or admitting office printout, but only through the third count of the counter 821. This is long enough to print out the nursing station number and a space. At the beginning of the fourth count, the CEN1 signal is terminated and the counter 821 is reset by an R4 pulse. The CEN2 signal is now generated, and this signal enables the circuitry of FIG. 10. This circuitry prints out the bed number, the patient number, and the price of the bed. The gates 1014 to 1017 generate special characters as they are needed. The gate 1017 inserts a decimal point between the dollars and cents part of the bed price, for example. Finally an 3 reset pulse terminates the printout in the manner described above.

CHARGE INFORMATION PRINTOUT FORMAT GENERATOR

Figure 12:
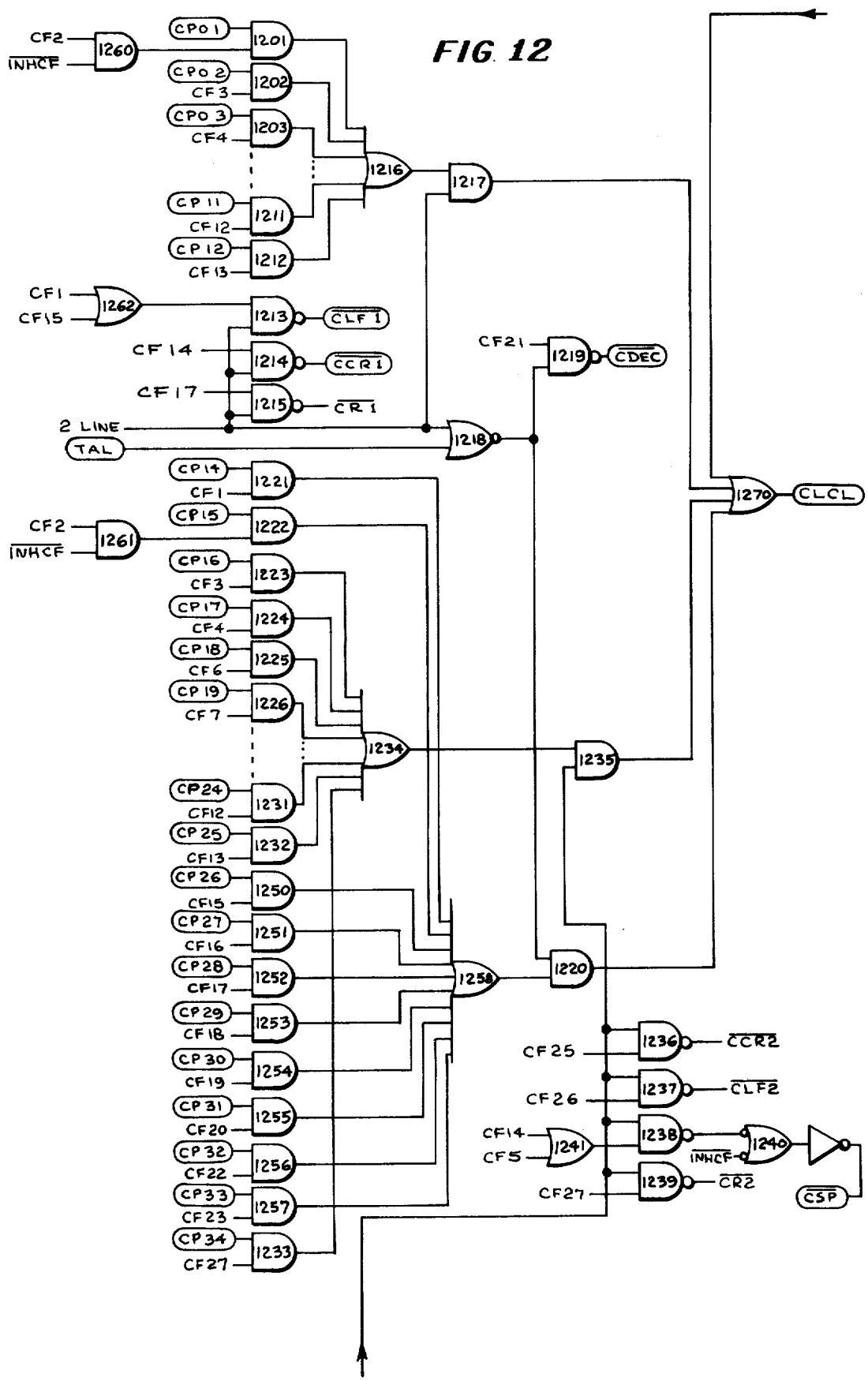
Figure 14:
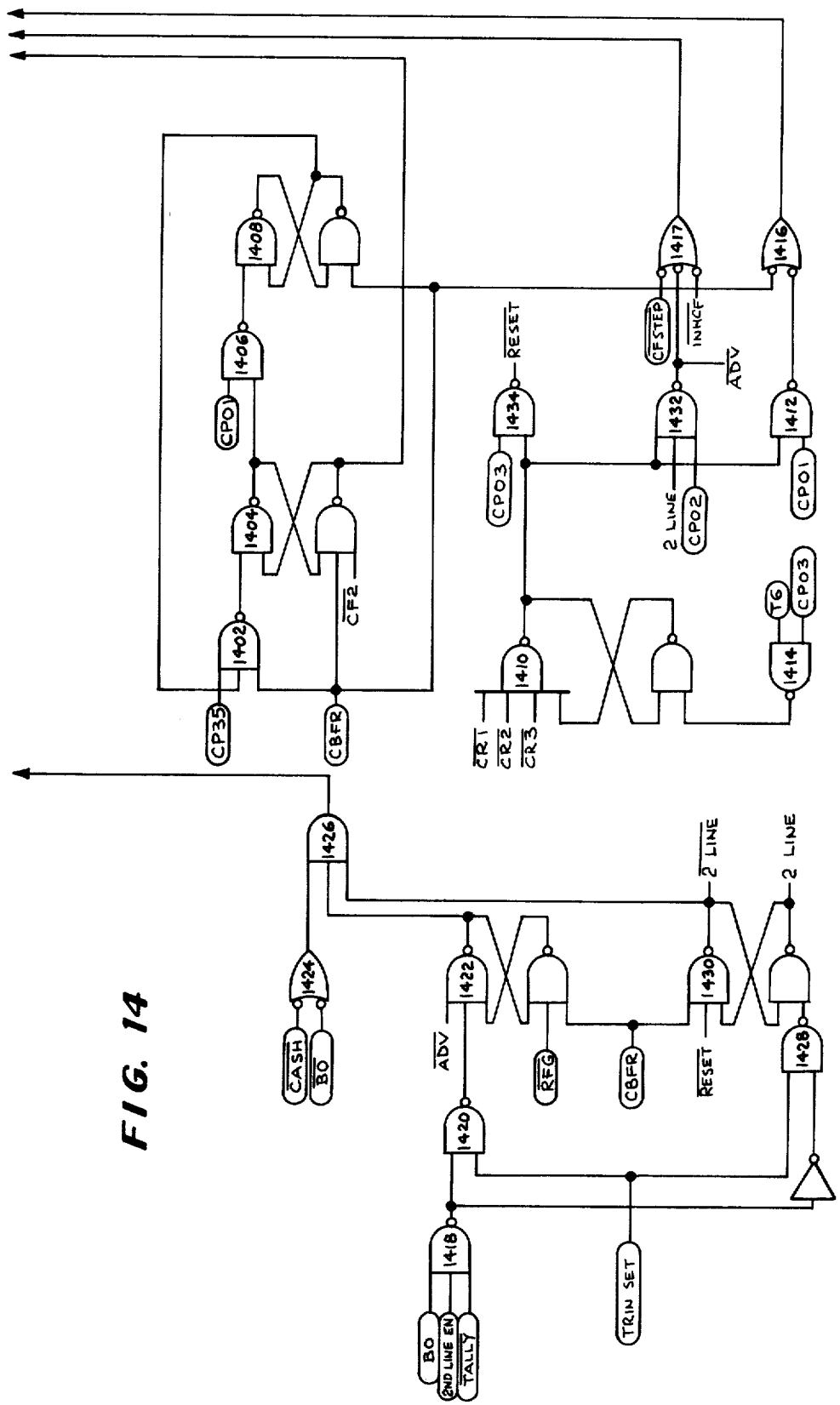
Figure 16:
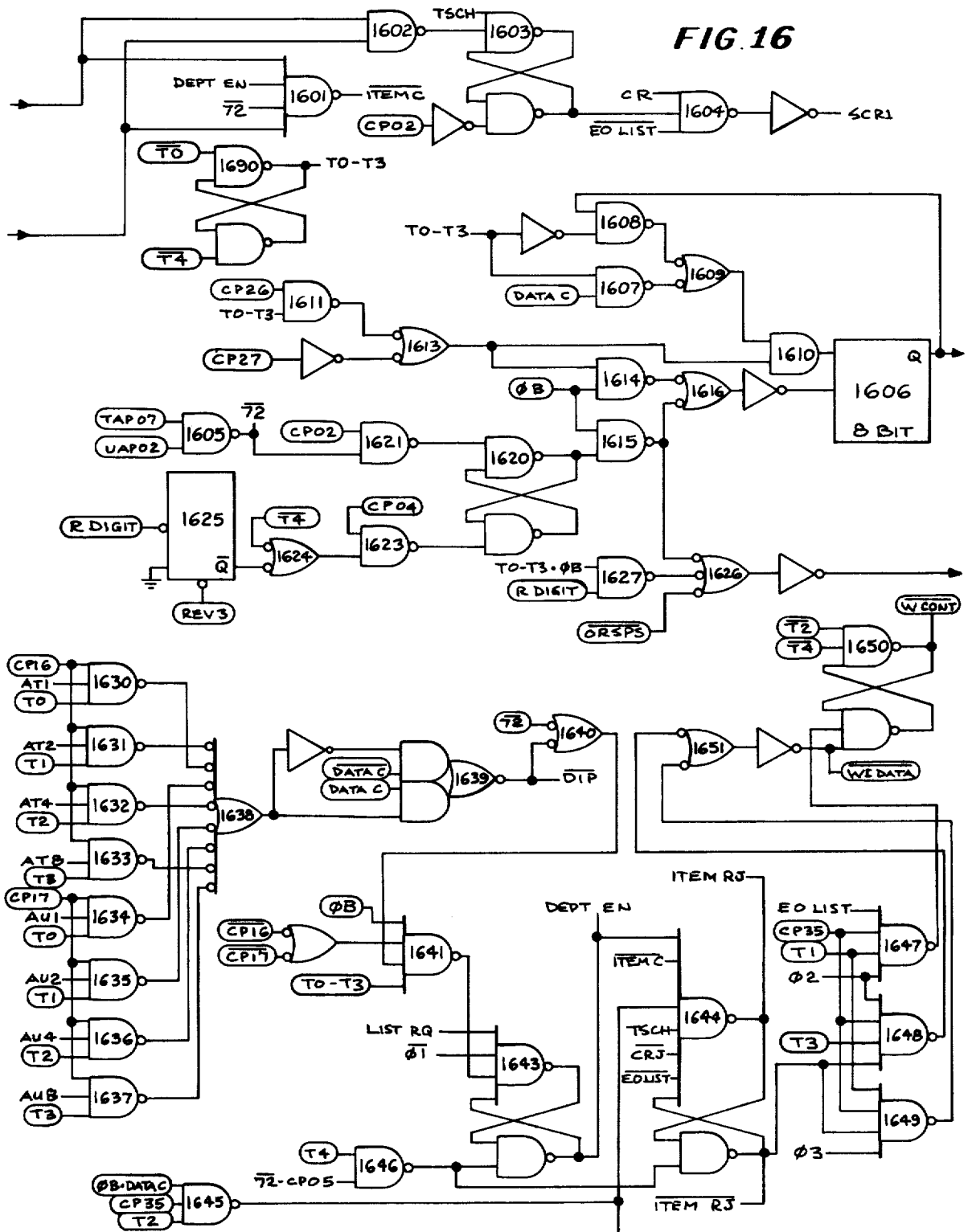

FIGS. 12 through 14 illustrate the logic circuitry used in the format generator for controlling the printout of data from the charge information storage area buffer track of the magnetic drum. In general, the circuit is identical in function and in mode of operation to the bed information printout format generator described above.

When information for printout is stored in the charge information buffer storage area, the CBFR signal generated in FIG. 7 is initiated. The CBFR signal releases bistable 1404 and 1408, and also releases the clear terminal of a counter 1320, thus allowing the counter to begin to count. The CBFR signal is connected to the clear terminal of the counter 1320 by a gate 1416. The CBFR signal also enables a gate 1402 (FIG. 14) and allows a CP35 timing pulse to set a bistable 1404. The output signal from bistable 1404 disables a gate 1322 and thus terminates a CF0 signal previously generated by the counter 1320. The termination of this CF0 signal is used by other parts of the system as an indication that information from the charge information storage area buffer track is ready to be printed out. The bistable 1404 enables a gate 1406 which then allows a CP01 timing pulse to set the bistable 1408. The bistable 1408 disables the gate 1402 and prevents any further CP35 timing pulses from reaching the bistable 1404.

At the end of a printout, one of three gates 1215, 1239, or 1308 generates a reset pulse CR1, CR2, or CR3 which sets the bistable 1410. The output of a bistable 1410 enables a gate 1412 to pass a CP01 timing signal to the clear terminal of the counter 1320, clearing the counter and reinstating the FO output signal. The bistable 1404 was previously reset when the counter 1320 reaches the count of CP2, so the gate 1322 is now enabled to pass the CF0 signal. This CF0 signal is used by other parts of the system as an indication that the printout is finished. The CR2 and CR3 signals are also combined in a gate 1313 to form a NX-ITEM signal. This signal is used by the tally search control logic as an indication of when a printout is finished. The bistable 1410 is then reset by gate 1414 during the T6 part of the next CP03 timing pulse.

Four different printout formats can be generated by the circuitry of FIGS. 12 through 14. A first format is used for transmitting charge information to the cashier's office. A second format is used during the first part of an APC (all patient charges) printout to send charge information to the business office. A third, two section format is used during the latter portion of an APC printout to transmit both charge information and patient numbers to the business office. A fourth format is used for the printout of tally search results.

When a printout is to be directed to the cashier's office, the printout format is generated by the gates 1221 through 1233, and by the gates 1250 to 1257. The output signals from these gates are combined by the gates 1234 and 1258, and are then passed through the gates 1235 and 1220 to the output gate 1270 where they become a part of the CLCL format signal. The gates 1221 and 1222 cause the point of sale number to be printed out. The gates 1223 and 1224 cause the department number to be printed out. The gates 1225 through 1232 cause a printout of the item number. The gates 1250 and 1251 cause a printout of the quantity of items. The gates 1252 through 1257 cause a printout of extended price for all items included in the transaction. The gate 1233 causes the credit symbol to be printed, if any is present. The gates 1236 through 1239 are also enabled during the cashier's printout, and these gates insert the various special characters into the printout in the appropriate places. The manner in which these gates are enabled by the counter 1320 is identical to the manner in which the analogous gate in the bed printout format logic circuitry were enabled by the counter 821.

The gates 1220 and 1235 are enabled during the generation of the cashier printout CLCL signal.

The gate 1220, and also the decimal point gate 1219, are enabled by the output signal from a gate 1218. The gate 1218 generates an enabling output signal because neither of its inputs is receiving a signal. The gate 1235, and also the gates 1236 through 1239, are enabled by a signal generated by a gate 1426. The gate 1426 is enabled because all three of its inputs receive signals. A CASE signal, which is generated during a cashier information printout, passes through the gate 1424 to the first input of the gate 1426. The bistable 1430, which is left in the clear state during a cashier information printout, supplies a signal to the second input of the gate 1426. The bistable 1422, which is set during a cashier information printout, supplies a signal to final input to the gate 1426. The bistable 1422 is set by a TRIN SET signal, which passes through a gate 1420. The TRIN SET signal is generated shortly after the CBFR signal by the circuitry shown at the bottom of FIG. 7. This TRIN SET signal either sets the bistable 1422 or the bistable 1430, depending upon whether a signal is generated by a gate 1418. If all the inputs to the gate 1418 receive positive level signals, the output of the gate 1418 disables the gate 1420 and enables the gate 1428, thus allowing the TRIN SET pulse to set the bistable 1430. During a cashier information printout, only the input to the gate 1418 which is receiving an inverted TALLY signal is enabled, so the gate 1418 disables the gate 1428 and enables the gate 1420 to pass the TRIN SET pulse to set the bistable 1422.

A simple APC business office printout uses exactly the same format as a cashier information printout described above. The gate 1418 enables a TRIN SET pulse to pass through the gate 1420 and to set up the bistable 1422. The inverted BO (business office) signal passes through the gate 1424. The signal from the bistable 1422 and the BO signal combine with the signal from the bistable 1430 to enable the gate 1426. Once again, the lack of any input signals to the gate 1218 causes this gate to enable the gate 1220 and the gate 1219.

During the latter portion of an APC (all patient charge) search it is necessary to search the charge storage area for patient numbers not found in the bed information storage area. These patient numbers must be printed out under the control of the charge information printout format generator. To initiate such a printout, a 2ND LINE EN (second line printout enable) signal is generated in another part of the system. This signal, plus the BO signal and the inverted TALLY signal, enable the gate 1418. The output signal from the gate 1418 disables the gate 1420 and enables the gate 1428. The TRIN SET pulse then passes through the gate 1428 rather than the gate 1420, and sets the bistable 1430 instead of the bistable 1422. The bistable 1430 generates a 2 LINE signal. This signal enables the gates 1213, 1214, 1215, and 1217 to print out the patient case number. The patient case number format is established by the gates 1201 to 1212. The signals from these gates flow through a combining gate 1216, through the enabled gate 1217, and out through the output gate 1270 to become the CLCL signal. While this is happening, the 2 LINE signal causes the output of the gate 1218 to disable the gates 1220 and 1219, thus suppressing half of the usual business office printout. The 2 LINE signal also disables the gate 1426 and suppresses the other half of the usual business office printout.

When the patent number has been printed out, the gate 1215 generates a CR1 reset signal which sets the bistable 1410 in the usual manner. Printout does not stop at this point, however. The output of the bistable 1410 is combined with the 2 LINE signal and with a CP02 timing signal by a gate 1422 to form an ADV (counter advance) pulse which is fed through the gate 1417 to advance the counter 1320 from a count of CF0 to a count of CF1. This prevents the CF0 signal from being generated, and thus prevents the usual printout termination procedure from being carried out. This same ADV pulse also sets the bistable 1422. The output signal from the bistable 1410 is then combined with a CP03 timing signal by a gate 1434 to generate a RESET pulse. This pulse clears the two line bistable 1430. The format generator is thus returned to its usual business office printout state, and a conventional business office printout then occurs. Thus, when the 2ND LINE EN signal is present, the patient case number is printed out ahead of the usual charge information printout.

During a tally search printout, the department or revenue number, the item number, and the credit symbol are printed out. The remainder of the tally information is supplied by the tally search control logic circuitry, which will be described in more detail below. During a tally search, the gate 1426 enables the gates 1235 and 1236 through 1239, to allow a printout of all the above information, with the exception of the credit symbol. The printout of the credit symbol is initiated by a gate 1302, which is enabled directly by a TAL (tally) signal. This same TAL signal causes the gates 1218 to disable the gate 1220 and 1219, thus suppressing the printout of quantity and price information.

The logic circuitry shown at the top of FIG. 13 is used to control the printout of tally information supplied by the tally search control logic circuitry, and will be described below when the tally search control logic circuitry is described.

TALLY SEARCH CONTROL LOGIC

The tally search control logic is shown in FIGS. 15 through 18. A tally list is a complete listing of all items relating to a particular department of the hospital that are received or dispersed during a given day. A tally search is initiated by setting a pair of dials to the number of a department, and then by depressing a tally search pushbutton. The department number is then read into a pair of buffers 1512 and 1514 shown in FIG. 15, and a tally search begins. The tally search logic scans the locations within the charge information storage area looking for the specified department number. When a location containing the specified department number is found, the item number stored in the location is retrieved and is stored in a 64 bit shift register 1504 shown at the top of FIG. 15. The number indicating the quantity of items involved in the transaction is fed into an 8 bit shift register 1606 shown at the top of FIG. 16. Then the charge information storage location is marked for printout by the circuitry shown in the lower right hand portion of FIG. 16.

The tally search control logic then continues to scan the information in the charge information storage area, looking for other locations containing the same department number and item number. When such a location is found, the location is marked as having been printed out, and the quantity of items involved is fed into the shift register 1606. A serial adder circuit shown at the top of FIG. 17 keeps a running total of the quantity of items encountered. When the entire drum has been scanned, the tally search procedure stops temporarily, and the results of this first tally search is printed out. The department number and item number are printed out by the usual output list control circuitry in the manner described above. The total quantity of items encountered is then fed out of the adder circuit at the top of FIG. 17 in the form of a TAL TATA signal. This signal is transmitted to the business office teleprinter under the control of the charge information printout format logic. When printout is completed, the NX ITEM signal generated by the charge information printout format logic initiates a new search for another item.

This searching procedure continues until finally a complete scan of the charge information storage area is made during which no further new items are found. At this point, the logic circuitry shown at the bottom of FIG. 18 terminates the tally search and initiates an erasure of printout markers from the charge information storage area.

Figure 17:
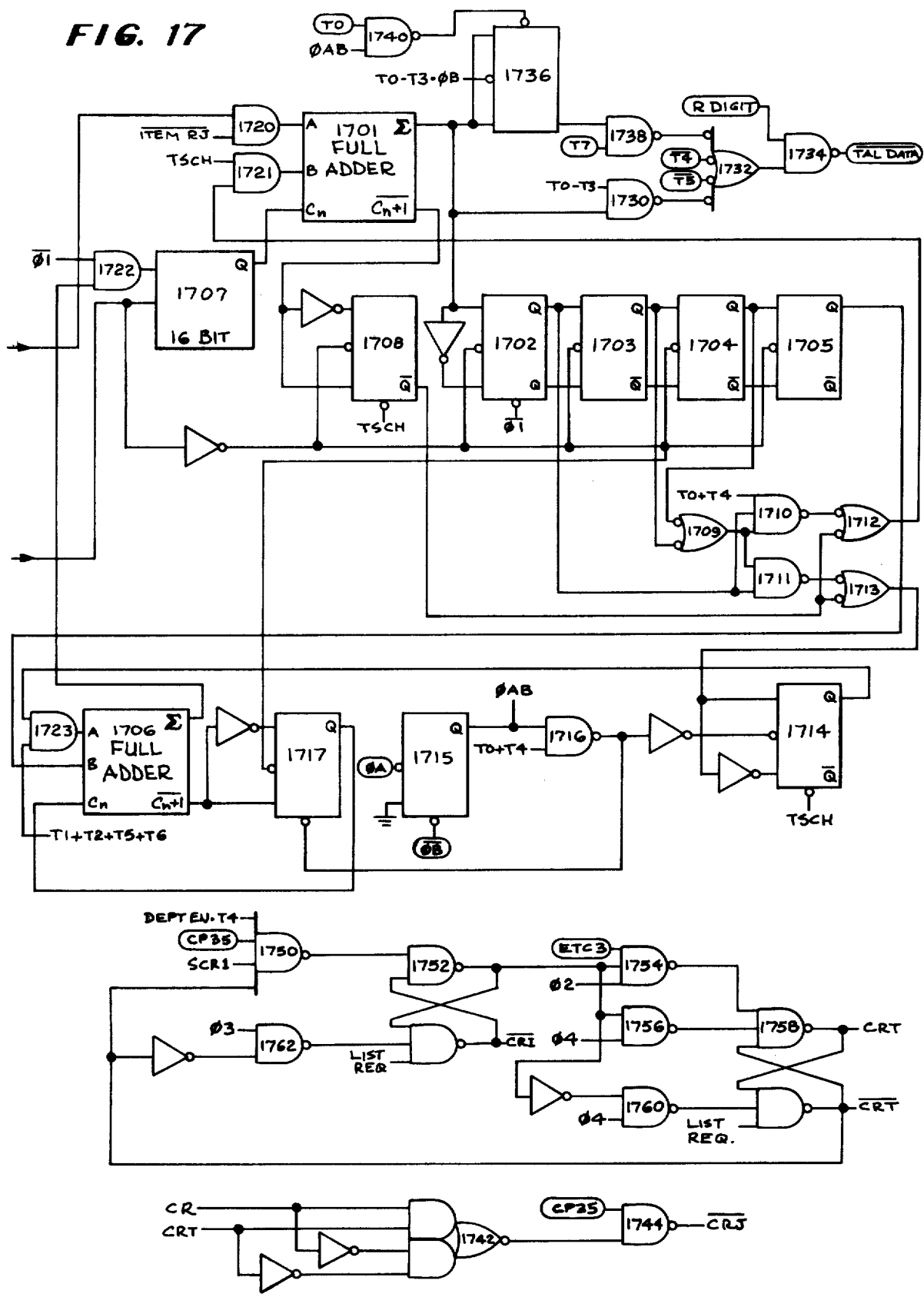
Figure 18:
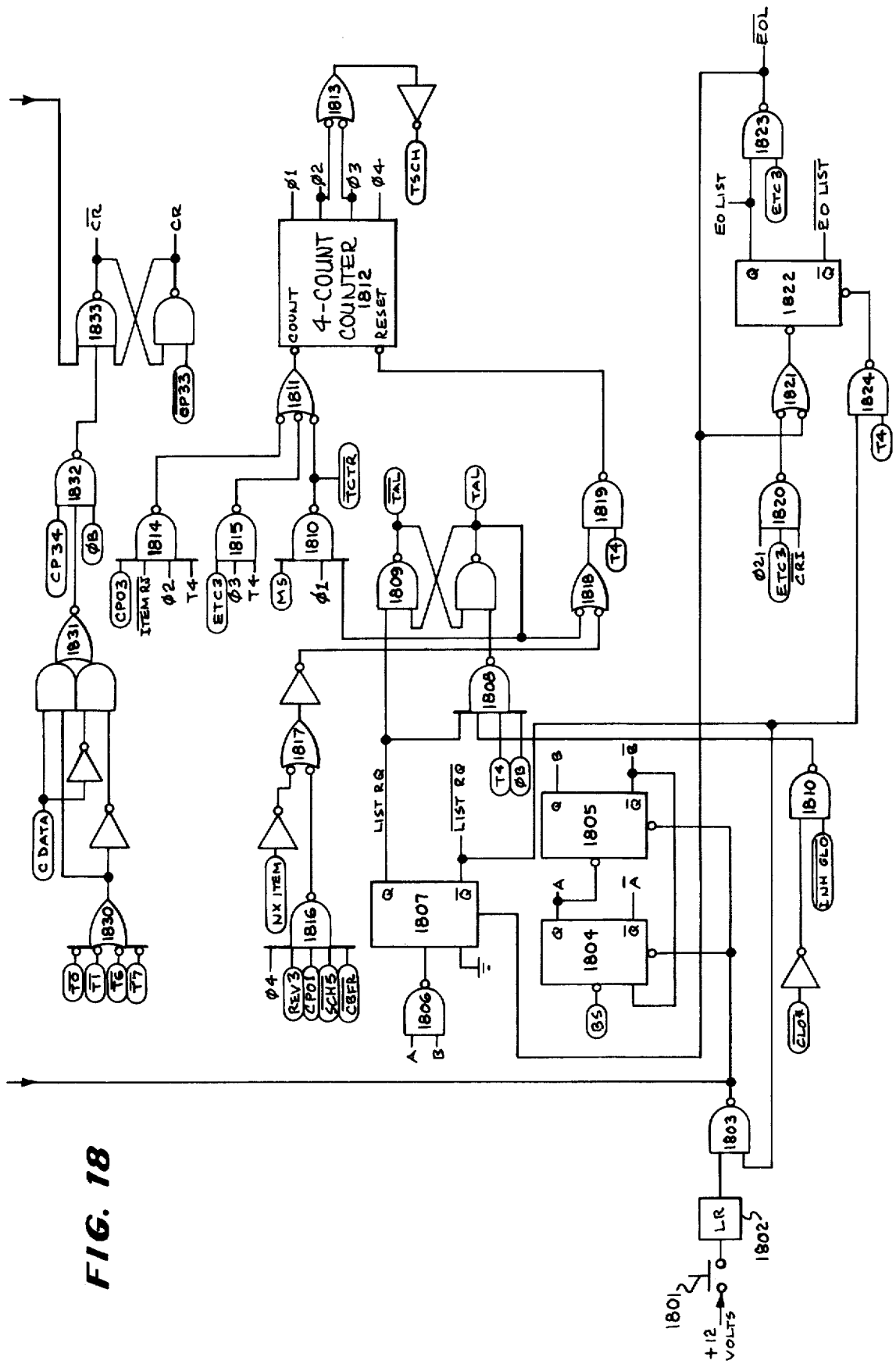

Credit items are detected by the circuitry shown at the top of FIG. 18. These items are not included in the usual tally listings. When a credit item is encountered, this fact is remembered by a flip-flop 1752 located at the bottom of FIG. 17. A special tally search is then initiated for credit entries, and a credit printout is initiated. Thus, tally debits and credits are summed separately.

A tally search is initiated by depression of a tally pushbutton 1801 (FIG. 18). The signal generated by this pushbutton is passed through a transient filter and level converter 1802 and enables a gate 1803 to clear two flip-flops 1804 and 1805, and also the two buffers 1512 and 1514. When the pushbutton is released, BS timing pulses begin to toggle the flip-flops 1804 and 1805. The flip-flops 1804 and 1805 are connected together to form a four count binary counter initially set to zero count.

When the counter reaches a count of 1, the outputs from the two flip-flops enable a gate 1518. The gate 1518 generates a signal and transmits it to the tens digit output enable terminal of a department number manual switch input circuit 1510. The circuitry 1510 contains two ten position switches, and suitable logic circuitry for generating two four bit binary numbers. It is similar to the switch input that is located in the cashier's office and disclosed in the concurrently filed application. The switches are set up to display the number of the department for which the tally search is being carried out. In response to the signal from the gate 1518, the tens digit of the department number indicated by the switches appears at the BCD output of the unit 1510. The next BS pulse enables a gate 1516 and causes this number to be loaded into the tens digit buffer 1512 (the buffers 1512 and 1514 are sets of four bistables each equipped with an input gate having one terminal connected to the load terminal).

The trailing edge of the BS pulse toggles the flip-flops 1805 and 1505, advancing the count to 2. The outputs of the flip-flops 1804 and 1805 now enable a gate 1522 and cause a units digit to be loaded into the units digit buffer 1514 when the next BS pulse enables a gate 1520. The trailing edge of this BS pulse again toggles the flip-flops 1804 and 1805, and advances the count to 3. The output of these two flip-flops now enables a gate 1806 and causes the gate 1806 to toggle a flip-flop 1807 into the Q state. The flip-flop 1807 generates a LIST RQ (list required) signal. This signal is applied to one input of a gate 1808. Two other inputs of the gate 1808 are periodically enabled by a T4 timing pulse and a phase B timing signal. If the output signal from a gate 1810 is high, gate 1808 will set a bistable 1809, causing the bistable 1809 to generate a TAL (tally) signal. This signal initiates the tally search.

The output of the gate 1810 is normally positive. It goes negative whenever any form of CIP storage area search is in progress, as indicated by a CL0* signal. This signal is generated by circuitry shown in FIG. 25. When an APC operation has reached the point where a tally search can begin, and INH CL0 signal defeats the action of the CL0* signal and allows the gate 1810 to set the bistable 1809.

The operation of the tally search logic is controlled by a counter 1812. This counter generates sequential count signals called PHASE 1, PHASE 2, PHASE 3, and PHASE 4. Each count applied to the counter 1812 causes the PHASE signal currently generated to terminate and causes the next sequential PHASE signal to be generated. When the counter 1812 is cleared, the PHASE 1 signal is generated.

Initially, the counter 1812 is cleared, and generates a PHASE 1 signal. When the TAL signal arises, it is combined with the PHASE 1 signal and the MS end of drum rotation timing signal by a gate 1810 to generate a counter advance pulse. This pulse is fed to the counter 1812 through a gate 1811. This same pulse is given the name TCTR and is fed to the drum control logic, to cause the charge information scan to commence on the first track in the charge information storage area.

The signals generated by the counter 1812 determine the mode of operation of the tally search logic. PHASE 1 is merely a standby condition of the tally logic circuit during which the circuit waits until the drum is at the beginning of a new revolution. PHASE 2 is the phase of operation during which the circuit looks for a new item number. When a new item number is found, the tally logic shifts into PHASE 3 and looks for other locations containing the same item number. When the charge information storage area has been completely scanned, the system shifts into PHASE 4. This phase is again a standby phase during which the tally logic waits for data to be printed out. When printout is completed, the NX ITEM signal passes through the gates 1817, 1818, and 1819 and clears the counter 1812, recommencing PHASE 1. Alternatively, the counter 1812 can be cleared by a signal generated by a gate 1816. This gate generates a pulse whenever both the SCH 5 signal and the CBFR signal are terminated. Thus, if no item is marked for printout during a search, the mere termination of the search will automatically return to counter 1812 to PHASE 1 and will continue the tally search. This can happen when only credit items are found during a PHASE 2 search. The system remains in PHASE 2, but a CRT signal prevents a gate 1820 from terminating the tally search in the usual manner, as will be explained below.

The end of PHASE 2 is indicated by the absence of an ITEM RJ signal during any CP03 character count. The ITEM RJ signal is generated by a bistable 1644. It represents the cumulative results of several tests. If the data in a storage location item fails to pass any item reject test, an ITEM RJ signal is generated. This signal disables the gate 1814 and prevents a CP03 timing signal from advancing counter 1812 into PHASE 3. If all the tests are passed, the ITEM RJ signal is not generated and the counter 1812 advances to PHASE 3. A search for further items having the same item and department number is then commenced. PHASE 3 is automatically terminated when the entire charge information storage area has been searched as indicated by an ETC 3 signal. The ETC 3 signal is applied to a gate 1815. The output signal from the gate 1815 advances the counter 1812 to PHASE 4 and puts the tally logic on standby awaiting printout.

During PHASE 2, the information stored in the charge information section of the drum is scanned, and an attempt is made to find an item that has a department number which is identical to the number stored in the two buffers 1512 and 1514. The DATA C signal coming from the charge area storage is fed into a comparison gate 1639. The other input to the comparison gate 1639 is a signal presented by a gate 1638 and bearing the data from the two buffers 1512 and 1514. The timing gates 1630 through 1637 are so arranged that the information from the buffers 1512 and 1514 is presented in the form of two four digit teleprinter signals, one occurring during CP16, and one occurring during CP17. For example, the AT1 output bit from the buffer 1512 appears at the output of the gate 1638 during the T0 portion of CP16, and the AT2 bit presented by the same buffer appears at the output of the gate 1638 during the T1 portion of CP16. These two signals flow respectively through the gates 1630 and 1631. In a similar manner, the other bits from the two buffers are also presented at the output of the gate 1638 just as though they were part of an incoming teleprinter signal. Only four bits of the 8 bit teleprinter code are presented, so the comparison of this data with the data flowing from the charge information storage area must be limited to the first four bits of the teleprinter characters. Whenever the output signal from the gate 1638 matches the signal presented by the DATA C signal, a DIP signal generated by the gate 1639 will not be present. No signal flows from the gate 1640, and the gate 1641 remains disabled. Any time the comparison fails, a DIP signal is immediately generated, passed through the gate 1640, and used to partially enable the gate 1641. The other inputs to the gate 1641 prevent this gate from being enabled except during bit counts T0 through T3 of characters CP16 and CP17, and only during a PHASE B timing pulse. This limits the comparison to a comparison of the first four bits of the numbers stored in characters 16 and 17. This is where the digits of the department number are stored. If the comparison fails, the gate 1641 is enabled and clears a bistable 1643, terminating a DEPT EN signal which the bistable 1643 normally generates. Two other imputs to the bistable 1643 allow it to be cleared by a PHASE 1 signal and by a LIST RQ signal when a tally search logic is in the PHASE 1 mode of operation, or when no tally search is being carried out. When the DEPT EN signal terminates, it sets the bistable 1644 and causes the ITEM RJ (item reject) signal to be generated. As mentioned above, this signal prevents the logic from entering PHASE 3. The bistable 1643 is then reset by a gate 1646 during the T4 bit of the next CP05 timing signal, except when the address count for the charge information storage area reaches a count of 72. One input to the gate 1646 is a T4 timing signal. The other input receives a CP05 signal which has been ANDED together with an inverted 72 signal. The inverted 72 signal is generated by a gate 1605 located at the top of FIG. 16. This inverted 72 signal is also used to force the gate 1640 to generate a false DIT signal during the scanning of address location 72, to insure that any random data encountered there will not initiate a PHASE 3 operation.

The department number comparison test is only one of several tests which can cause the generation of an ITEM RJ signal during PHASE 2. The gate 1645 can also cause the item reject. This gate detects the presence of a marker in the second bit of character 35. Such a marker indicates that an item has already been included in part of the tally search, and therefore can now be overlooked. A CRJ signal can also cause the item reject. This signal is generated by a gate 1744 whenever the credit symbol contained within the storage area indicates that this item should not be included in the tally. As explained above, debit and credit tallys for items bearing the same item number are carried out separately. A TSCH signal causes an item reject to occur whenever the system is in PHASE 1 or PHASE 4. This signal is actually a combined PHASE 2 and PHASE 3 signal, generated by a gate 1813. The bistable 1644 is reset by the same signal which resets the bistable 1643 during every CP05 character timing pulse.

When an item reject does not occur in PHASE 2, the output of the bistable 1644 enables a gate 1648 during T3 of CP35 and causes the gate 1651 to generate a WI DATA signal, which causes a printout marker to be written into the fourth bit of the 35th character of the storage location currently being scanned. This marks the location for printout under the control of the charge information printout format generator during the next LIST 5 search. This data is combined with the results of the tally search to produce the tally printout data. The output signal from the gate 1651 also sets a bistable 1650 and causes a W CONT signal to be generated. The W CONT signal causes the WI DATA signal to be written onto the drum.

As mentioned above, the ITEM RJ signal causes the gate 1814 to generate a counter advance pulse during the character count CP03. This pulse passes through the gate 1811 and causes the counter 1812 to advance to a count of PHASE 3. The tally logic now looks for charge information storage locations containing the same department number and the same item number as the location marked for printout, and adds up the quantity numbers retrieved from the locations found.

As each area of the charge information storage section of the drum is examined during the PHASE 2 portion of the tally operation, the item number found in each location is read into a 64 bit shift register 1504 shown at the top of FIG. 15. Data from the output of the shift register 1504 normally recirculates through the gates 1502 and 1503. During PHASE 2, the gate 1501 disables the gate 1502 and enables the gate 1506. The gate 1506 allows data from the charge information storage section of the drum to flow directly through the gate 1503 and into the shift register 1504. The data is clocked into the shift register 1504 by PHASE B pulses which pass through a gate 1509. The gate 1509 is controlled by a bistable 1507. The bistable 1507 is set only during the 8 character counts starting with the 18th and ending with the 25th. Thus, only the information contained in these character locations is read into the shift register 1504. Characters 18 to 25 contain the item number. As each location within the charge information storage area is scanned, the item number contained within that area is read into the shift register 1504 and is stored. When PHASE 2 terminates, the gate 1501 causes the shift register 1504 to function as a ring counter. Thus, during PHASE 3, the item number data is recirculated and is not lost.

During PHASE 3, we wish to find all charge information storage locations containing an item number identical to the one found during the PHASE 2 search and stored in this shift register 1504. When the item number for each successive storage location is presented by the DATA C signal, it is compared to the number stored within the shift register 1504 by a comparison gate 1505. The output of the gate 1505 remains low so long as the comparison is successful. If any bits in the two signals do not match up, the output of the gate 1505 goes high and partially enables a gate 1601. Other inputs to the gate 1601 are the DEPT EN signal generated by the bistable 1643, the inverted 72 signal generated by the gate 1605, and a PHASE B and CP18 to 26 timing signal generated by a gate 1508. These signals prevent comparison except during times when the item number data is presented by the DATA C signal, and also prevent a comparison when the department number contained within the area being searched does not match the department number stored in the buffers 1512 and 1514. Again, the inverted 72 signal prevents the comparison from occurring at an address 72 location. This address location is not used.

If the comparison is not successful, an ITEM C signal is generated by a gate 1601. This ITEM C signal is fed to the bistable 1644 and causes an ITEM RJ signal to be generated. The bistable 1644 then disables a gate 1649, and the item encountered is not marked as print out. If the comparison is successful, and if all other item reject tests are passed, the ITEM RJ signal is not generated and the bistable 1644 enables the gate 1649. The gate 1649 causes a mark to be placed in the second bit of the 35th character, thus marking the location as having already been printed out. The ITEM RJ signal then allows the quantity information stored in this location to be added to the tally count, as will be explained in detail below.

Whenever information is read out of the charge information storage section of the drum, bits 1 to 4 of the 26th and 27th characters are continuously read from the DATA C signal line, through gates 1607, 1609, and 1610, and into an 8 bit shift register 1606. This is the quantity information, or information as to how many items are involved in the transaction. Therefore, the shift register 1606 always contains two 4 bit BCD numbers representing the quantity or number of units involved in each transaction. At the beginning of CP26, a gate 1611 is enabled by CP26 timing signal and by a T0-T3 timing signal generated by a bistable 1690. The output signal from the gate 1611 passes through a gate 1613 and enables both the input to the shift register 1606 and also a gate 1614. The gate 1614 controls the flow of PHASE B timing signals to the clock terminal of the shift register 1606. Simultaneously, the T0-T3 signal enables a gate 1607, and allows the DATA C signal to flow into the shift register 1606. The gate 1611 maintains its output signal only long enough for four PHASE B pulses to pass through the gates 1614 and 1616, so only four bits of data are fed into the 8 bit shift register 1606. This data is stored until the beginning of the immediately following CP27 timing signal. This signal then is passed through the gate 1613 and enables the two gates 1610 and 1614 for a count of 8 PHASE B timing pulses. During the first four of these timing pulses, four bits of data are read out of the 27th character of the charge information storage location and into the shift register 1606. The T0-T3 signal then terminates, disabling the gate 1607 and enabling the gate 1608 which allows shift register data to recirculate. Four more PHASE B pulses now reverse the order of the two BCD numbers within the shift register 1606, so that the units digit is closest to the shift register output.

Tally data is summed and stored in the circuit shown at the top of FIG. 17. This circuit comprises basically a ring counter circuit into which a serial adder is inserted, or a ring counter and serial adder circuit. The main adder logic unit is a full adder 1701 shown at the top of FIG. 17. Data flows out of the 16 bit shift register 1707, through the adder 1701, through the four flip-flops 1702 through 1705, through the BCD correction full adder 1706, and back into the 16 bit shift register 1707. The total storage capacity of the ring counter is 20 bits, providing sufficient room to store a binary coded decimal number as great as 9,999 while still leaving four bits of buffer track available for overflow.

Data is caused to recirculate by shift pulses generated by a gate 1626. Usually these recirculation pulses are PHASE B pulses supplied by a gate 1627. The other input signals to the gate 1626 are used only when data is read out during printout. These signals will be discussed more fully below.

After each area of the charge information storage section of the drum is scanned for tally data, whether or not tally results were found, the data stored in the ring counter at the top of the FIG. 17 is shifted once around the loop. This requires 20 shift pulses. A bistable 1620 enables the gate 1615 just long enough to pass exactly 20 PHASE B timing pulses to the ring counter serial adder circuit to produce this circulation. The bistable 1620 is set by the leading edge of a CP02 timing signal which passes through a gate 1621. The other input to the gate 1621 serves merely to prevent circulation when the 72nd location on a track is scanned. The bistable 1620 remains set until the second half of a CP04 timing pulse when it is cleared by a gate 1623. The inputs to the gate 1623 are a CP04 timing signal and a T4 timing signal which normally passes through a gate 1624.

If the various tests performed upon a given section of the storage area do not result in an item reject, a gate 1720 at the A input to the full adder 1701 is enabled to pass data from the 8 bit shift register 1606 into the ring counter and adder circuit by the inverted ITEM RJ signal. Bits of information flow into the full adder 1701 from the shift registers 1606 and 1707 during the next 20 bit counting period. The gate 1615 provides counting pulses both to the gate 1616 and to the gate 1626 so that both sets of data advance simultaneously into the full adder 1701. Initially, the output of both shift registers is presented to the A and to the Cn inputs of the full adder 1701. The full adder 1701 calculates the binary sum of these two bits and applies this sum to the input of a flip-flop 1702. A carry bit, if there is any, is applied to the input of a flip-flop 1708. The first counting pulse advances this data into the flip-flops 1702 and 1708, and also causes new bits to be presented at the outputs of the two shift registers 1606 and 1707. These new bits are now presented at the A and Cn inputs of the full adder 1701, and the carry bit from the first summing operation is presented to the B input by the flip-flop 1708, via gate 1712, and a second bit addition is performed. In a like manner, the remaining bits in the first BCD characters are added together and the binary sum is stored in the flip-flops 1702 through 1705. A carry bit resulting from the summing of these two characters may be present in the flip-flop 1708.

Since these numbers are in BCD form rather than in binary form, it is necessary to check the resulting sum to see if it exceeds 9. If it does, then it is necessary to add the BCD number six (0110) to the resulting sum so that the sum is in BCD form, rather than in binary form. It is also necessary to generate a BCD carry signal if the sum is greater than 9. If the sum is greater than 9, a signal will appear at the outputs of the two gates 1712 and 1713. These two gates each receive an input from the flip-flop 1708 when the sum is 16 or greater, and they each receive an input from one of the two gates 1710 and 1711 when the sum is between 10 and 15. The gates 1710 and 1711 are partially enabled by the flip-flop 1702 when the sum is greater than 8 but less than 16, and are disabled by a gate 1709 when the sum is less than 10, as indicated by "0"s in both the flip-flops 1703 and 1704. The gates 1710 and 1711 perform identical functions, but the gate 1710 is disabled except during T0 and T4 bit timing intervals so that the nine detection logic affects the carry to the full adder 1701 only when a complete BCD character is contained in the flip-flops 1702 to 1705.

The output of the gate 1713 is applied to the flip-flop 1714. This flip-flop 1714 is toggled by a special PHASE AB timing pulse generated by a flip-flop 1715 and allowed to pass through a gate 1716 only during the T0 and T4 timing intervals. This special timing pulse toggles the information presented by the gate 1713 into the flip-flop 1714 at the leading edge of a PHASE B timing pulse. Since the trailing edge of the PHASE B timing pulses are used to clock data through the ring counter and serial adder circuit, this means that the output signal generated by the flip-flop 1714 arises early enough to affect the next addition operation. This signal controls a gate 1723 which controls the flow of an artificially generated BCD number 6 (0110) into the A input of the full adder 1706. This BCD number is actually a T1 + T2 + T5 + T6 timing signal. If the binary number stored in the flip-flops 1702 through 1705 is greater than 9, the flip-flop 1714 allows this number 6 to flow into the A input of the full adder 1706 while the BCD number from the flip-flops 1702 through 1705 flows into the B input. The sum generated by the full adder 1706, now in the BCD form, then flows back into the shift register 1707 through a gate 1722. If there is an overflow carry from the adder 1706, it is stored temporarily in a flip-flop 1717 and is added into the next serial bit through the Cn full adder input.

This circuit continues to function in the above manner until twenty successive shift pulses from the gate 1716 have circulated the data all the way around the ring counter and back into the 16 bit shift register 1707. At the termination of this period, the updated tally sum is stored in the 16 bit shift register 1707, still in BCD form, with the least significant character adjacent the output of the shift register 1707.

The ITEM RJ signal, when present, disables the gate 1720. When this happens, no data is added to the circulating signal. The 20 counts then merely cause the 16 bits of data within the shift register 1707 to flow around the ring counter and back to the shift register.

At the end of each PHASE 3 scan, the shift register 1707 contains a number equal to the quantity of a particular type of item that was sold during a given day. The tally logic then enters PHASE 4 and then remains on standby until a record of this tally number can be printed out, along with the item number.

One of the tests performed by the item reject circuitry during PHASES 2 and 3 is a credit reject test. A credit symbol comparison circuit checks each item to see if the credit symbol location contains the letter C. If it does, a bistable 1833 generates a CR signal and causes a gate 1744 to generate a CRJ or credit reject signal. This signal causes an item reject, and also enables a gate 1604 shown at the top of FIG. 16. If the comparison of the item number in this location to the item number stored in the shift register 1504 is successful, this fact is noted by a bistable 1603. The bistable 1603 is initially set by a CP02 timing signal. The failure of the comparison test causes a gate 1602 to clear the bistable 1603, and the bistable then prevents the CR signal from passing through the gate 1604. If the item number comparison test is successful, the gate 1604 will pass the CR signal and generate an SCR1 signal. This signal is gated through a gate 1750 by a CP35 timing pulse, and sets a bistable 1752, which generates a CRI signal. The CRI signal immediately disables the gate 1501, thus preventing the loss of the item number currently stored in the 64 bit shift register 1504 even if PHASE 2 is still in progress. Later on the function of this CRI signal is taken over by a CRT signal generated by a bistable 1758 and also applied to the gate 1501. The bistable 1752 remembers the fact that a storage area bearing the item number stored in the shift register 1504 contained a C credit symbol and causes the tally control logic to initiate a second tally search for credit symbols based on this same item number.

During PHASE 4, the PHASE 4 signal toggles the bistable 1758 into the same state as the bistable 1752, and initiates the CRT signal. As mentioned above, this signal preserves the present item number within the shift register 1504 and causes the tally control logic to run a credit search for items of this type. If credit items are present but no debit items are present, it is necessary to set up the bistable 1758 without the use of a PHASE 4 signal. This is done by the gate 1754, which combines the PHASE 2 signal with an ETC 3 signal that is generated when the end of the last track in the charge information storage area is scanned.

The credit symbol check is performed by a comparison gate 1831. The C DATA signal is applied to this gate along with an output character signal generated by a gate 1830. The input signals to the gate 1830 are chosen so that they generate a teleprinter code letter "C" at the output of the gate 1830. This "C" is continuously compared with data coming from the charge information storage area. Whenever the comparison fails, an output signal from the gate 1831 partially enables a gate 1832. The gate 1832 is disabled by a CP34 character timing signal except during the CP34 character count when the charge symbol appears. It is finally enabled by a PHASE B timing signal. The output of the gate 1832 thus remains positive unless the comparison fails. If the comparison fails, the gate 1832 clears the bistable 1833 and terminates the CR signal. The CR signal is set up by a CP33 character timing pulse, just before the credit symbol comparison check is performed. The CR signal can also be terminated by the signal generated by a gate 1645 when an item found has already been marked as having been printed out.

The CR signal is compared with the CRT signal by a comparison gate 1742. During normal tally searches the CRT signal is not present. The gate 1742 then will generate an output signal whenever the CR output signal is present. This output signal produces a CRJ (credit reject) signal at the output of a gate 1744 during the 35th character timing pulse. During a tally search for credit items, the CRT signal is present. The gate 1742 then generates a CRJ signal whenever the CR signal is absent. Thus, the comparison gate 1742 and the output gate 1744 separate debit and credit items, and insure that only debit items are counted in the first listing and only credit items are counted in the second listing.

During a search for credit items, the output of the bistable 1758 enables the gate 1762 to reset the bistable 1752 during the PHASE 3. When the system once again enters PHASE 4, the output of the bistable 1752 is again transferred to the bistable 1758 to terminate the CRT signal. The tally search for debit items then continues as before.

The ultimate end of the tally search procedure is detected by a gate 1820. This gate is enabled when the end of the last track signal ETC3 occurs during PHASE 2 when no CRI signal is present. An output signal from the gate 1820 indicates that a debit search has gone all the way through the entire charge information storage area without finding any new tally items. This output signal is passed through a gate 1821 and toggles a flip-flop 1822, causing the flip-flop 1822 to generate an EO LIST signal. This EO LIST signal is first applied to the bistable 1644, causing the bistable to disable the two printout control gates 1648 and 1649. The EO LIST signal is also applied to a gate 1647, enabling that gate to generate a W CONT signal during T1 of every CO35 character count. This W CONT signal, in the absence of a WI DATA signal, erases all of the markers in the T2 locations of the various 35th character slots throughout the charge information storage area during the next complete scan of the storage area. The next ETC3 signal, which occurs after all printout markers have been erased, is combined with the EO LIST signal by a gate 1823 to generate an EOL signal. The EOL signal clears the flip-flop 1807, thus terminating the LIST RQ signal, and also passes through the gate 1821 and toggles the flip-flop 1822 back into the clear state. As an added precaution, the LIST RQ signal is passed through a gate 1824 during a T4 timing pulse interval to the clear terminal of the flip-flop 1822 to insure that the flip-flop 1822 is cleared.

During PHASE 1, the contents of the circulating ring counter and serial adder circuit are erased by the PHASE 1 signal. This signal disables the input gate 1722 to the shift register 1707, and also locks the flip-flop 1702 in the clear state. This erases and completely cleans out the shift register 1707 and the flip-flops 1702 through 1705. During both PHASE 1 and PHASE 4 the TSCH signal prevents any action within the shift register and serial adder by locking the flip-flop 1708 and 1714 in the clear state, by disabling the gate 1721 and by locking the ITEM RJ signal in such a state that it disables the gate 1720. Thus, during PHASE 4, the 16 bit shift register 1707 is effectively connected in a loop with the four flip-flops 1702 to 1705 to form a conventional 20 bit ring counter circuit, and the arithmetic sections are totally disabled.

The printout of tally data is accomplished during PHASE 4. As was noted above, one location is always marked for a business office printout. The list output control circuitry, described above, automatically initiates a printout of information from this location. The printout is controlled by the charge information printout format generator shown in FIGS. 12 to 14. The data is fed into the circuitry shown in FIG. 5 and is fed out to the business office teleprinter. In the discussion to follow it will be necessary to refer to all of these figures, as well as to FIGS. 16 and 17 which show tally search control logic.

Referring first to the FIGS. 12, 13 and 14, the tally printout is initiated in the usual manner by the CBFR signal enabling the gate 1402. When the business office teleprinter is available, CF STEP pulses begin to advance the 27 count counter 1320 in the usual manner. The TAL signal generated by the tally search control bistable 1809 enables the gate 1302 and 1303 in FIG. 13. This same signal also causes the gate 1218 in FIG. 12 to inhibit any printout from being initiated by a major portion of the gates included in FIG. 12. The only FIG. 12 gates which are allowed to act during a tally printout are the gates 1223 through 1232 in the lower portion of FIG. 12. These gates initiate a printout of a department number, a space, an item number, and a second space. This printout occurs during the time interval spanned by the timing signals CF3 to CF14. Nothing happens during the time intervals spanned by CF1, CF2, and CF15, because the gate 1310 (FIG. 13) causes the gate 1309 to generate an AEN signal, which cancels any buffer track printout during those periods.

The AEN signal is fed back to FIG. 5. This signal prevents any data from flowing to an output from the buffer charge information storage area through the gate 568, and simultaneously enables a gate 566 during all CP35 timing intervals, thus enabling data reaching the gate 572 via the TAL DATA signal to be loaded into the shift register 641 during the CA00 address location timing interval.

The CF15 timing signal sets a bistable 1311 which enables the gate 1309, so the AEN signal is continuously generated during all REV3 CP35 timing intervals which occur during the intervals defined by CF15 to CF19. The CF20 timing signal then resets the bistable 1311 and terminates the AEN signal.

As mentioned above, the department number and the item number are read out during CF counts 3 through 14. A credit symbol, if any, is printed out during CF20 by a gate 1302 in the usual manner. During the CF timing intervals 16 though 19, the two gates 1305 and 1312 generate the signals which control the flow of data out of the tally search control logic and into the data collection gate 572. In order to understand how this outputting of data works, it will be necessary to describe these two signals in detail.

The gate 1312 generates a CRSPS signal. This gate is partially enabled during CF timing intervals 15 through 19 by the bistable 1311, but is disabled during CF15 by an inverted CF15 signal. The gate 1312 is also partially enabled by a REV2 signal, which is generated during the latter portion of the time when a character is transmitted to an output teleprinter. (It will be remembered that it is during the REV3 revolution of the drum that a new character is found and stored in the shift register 641.) Thus, the CRSPS signal is present only during the drum revolution preceding the time when a character is found for printout. A final enabling signal to the gate 1312 is a CP30 timing signal. This signal occurs 72 times while the REV2 signal is present. Hence, 72 pulses appear at the output of the gate 1312 during each REV2 period. These 72 pulses comprise the CRSPS signal.

The R DIGIT signal is quite similar, but it is generated during REV3, when data is loaded into the shift register 641, and during CP35 character timing intervals. Again, this signal occurs once for every location in the buffer charge information storage area, so that 72 output pulses come from the gate 1305 during REV3. Each of these output pulses is exactly 8 bits long.

At the termination of the tally search procedure, the tally data result is stored in a 16 bit shift register 1707, with the least significant digit first in line to be read out of the shift register. It is necessary to shift this data so that the most significant digit is first in line, since the most significant digit must be printed out first. This task is carried out by the CRSPS signal. During REV2, the CRSPS signal transmits 72 pulses to the gate 1626, and causes the ring counter circuit to advance 72 positions forward. This circulates the data three times around the loop plus 12 bit positions, and leaves the most significant digit of the information first in line for printout at the output of the shift register 1707 when the REV2 signal ends and the REV3 signal commences.

During the first CP02 and CP03 timing intervals following the commencement of REV3, the gate 1615 will generate 20 pulses as usual, causing the data to circulate once around the loop. The most significant digit will again end up at the output of the shift register 1707, first in line for printout. During the next CP35 character counting timing interval, the R DIGIT signal will enable a gate 1607 to pass four shift pulses to the ring counter. This special signal comprises a T0–T3 bit timing signal generated by the bistable 1690 ANDed together with PHASE B timing pulses. The resulting four pulses will cause one four bit BCD number to be read out of the shift register 1707, through the full adder 1701 and into a gate 1730. During the same 4 bit interval, the gate 1730 is enabled by the T0–T3 timing signal. The R DIGIT signal enables an output gate 1734. Hence, the BCD number flows through the gates 1730, 1732, and 1734 and becomes a part of the TAL DATA signal. Inverted T4 and T5 timing signals fed to the gate 1732 add "1"s to bit positions 5 and 6 of the resulting output character, and the absence of a T6 timing input to the gate 1732 causes a "0" to appear in the 7th bit position of the output character. A flip-flop 1736, which is toggled by the same timing pulse signal that was applied to the gate 1627, counts the "1"s which occur at the output of the full adder 1701, and generates a parity bit which passes through a gate 1738 and into the gate 1732 during bit timing interval T7. In this manner, the first four bits of data within the shift register 1707 are converted into a complete 8 bit teleprinter character which appears at the TAL DATA output of the gate 1734. This character is repeatedly generated during this and all subsequent REV3 CP35 timing intervals.

When the R DIGIT signal terminates, it toggles a flip-flop 1625 (located in the middle and towards the left hand edge of FIG. 16), and causes this flip-flop to generate a signal which passes through a gate 1624 and permanently enables a gate 1623 to pass the full CP04 timing signal, rather than just the last half of this signal. This shortens the length of time during which the bistable 1620 is allowed to remain in a set position by the time which it takes to generate four PHASE B timing pulses and therefore reduces the number of pulses generated by the gate 1615 from 20 down to 16. Therefore, during the next CP02 and CP03 character timing interval only 16 counts appear at the output of the gate 1615. This is just enough counts to advance the data to the position where the most significant number is first in line at the output of the shift register 1707, ready to be shifted out again during the next CP35 timing interval. In this manner, a teleprinter character carrying the most significant (thousands) digit is generated 72 times during each REV3 CP35 timing interval, once for each storage location in the charge information buffer storage track. During one of these 72 times, the CA00 signal goes positive, and together with the AEN signal enables one of these 72 teleprinter characters to be loaded into the assembly shift register 641. During REVs 1 and 2 this teleprinter character is transmitted to the business office teleprinter.

The last time a teleprinter character containing the most significant digit information is generated, the flip-flop 1625 is cleared by the termination of the REV3 signal before another 16 counts can be applied to the ring counter circuit to restore the data to its original position. Thus, the loop circuit is now left with the most significant digit stored in the four flip-flops 1702 through 1705. The next most significant digit or hundreds digit, which is to be printed out next, is adjacent to the input end of the shift register 1707. During REV2 the CRSPS signal once again applies 72 pulses to the gate 1626 and clocks the data around the ring counter circuit three times plus 12 bit positions. This is just enough to advance the hundreds digit to the output of the shift register 1707, first in line for printout. The printout procedure then proceeds exactly as described above.

The same procedure is then followed to print out the 10's digit and the units digit during CF18 and 19. Thus, all four digits are printed out respectively during CF16, 17, 18, and 19. As mentioned above, the credit symbol, if any is present, is retrieved from the charge information buffer storage area in the conventional way during CF20. A CR3 signal generated by a gate 1308 then terminates the printout during CF23.

During the tally search procedure, the SCH 5 (search for printout markers) procedure is initiated by the TSCH signal. This signal passes through a gate 3129 (FIG. 31) and causes the SEARCH signal to be generated. Any time the TSCH signal is discontinued, the SEARCH signal causes the gate 3146 to begin a search for printout markers in the charge information storage area. The TSCH signal is terminated whenever the tally search control logic is either in PHASE 1 or PHASE 4, and therefore, a search of the charge information storage area for tally printout markers is automatically started when the PHASE 4 mode is entered.

PATIENT CHARGE SEARCH CONTROL LOGIC

Figure 27:
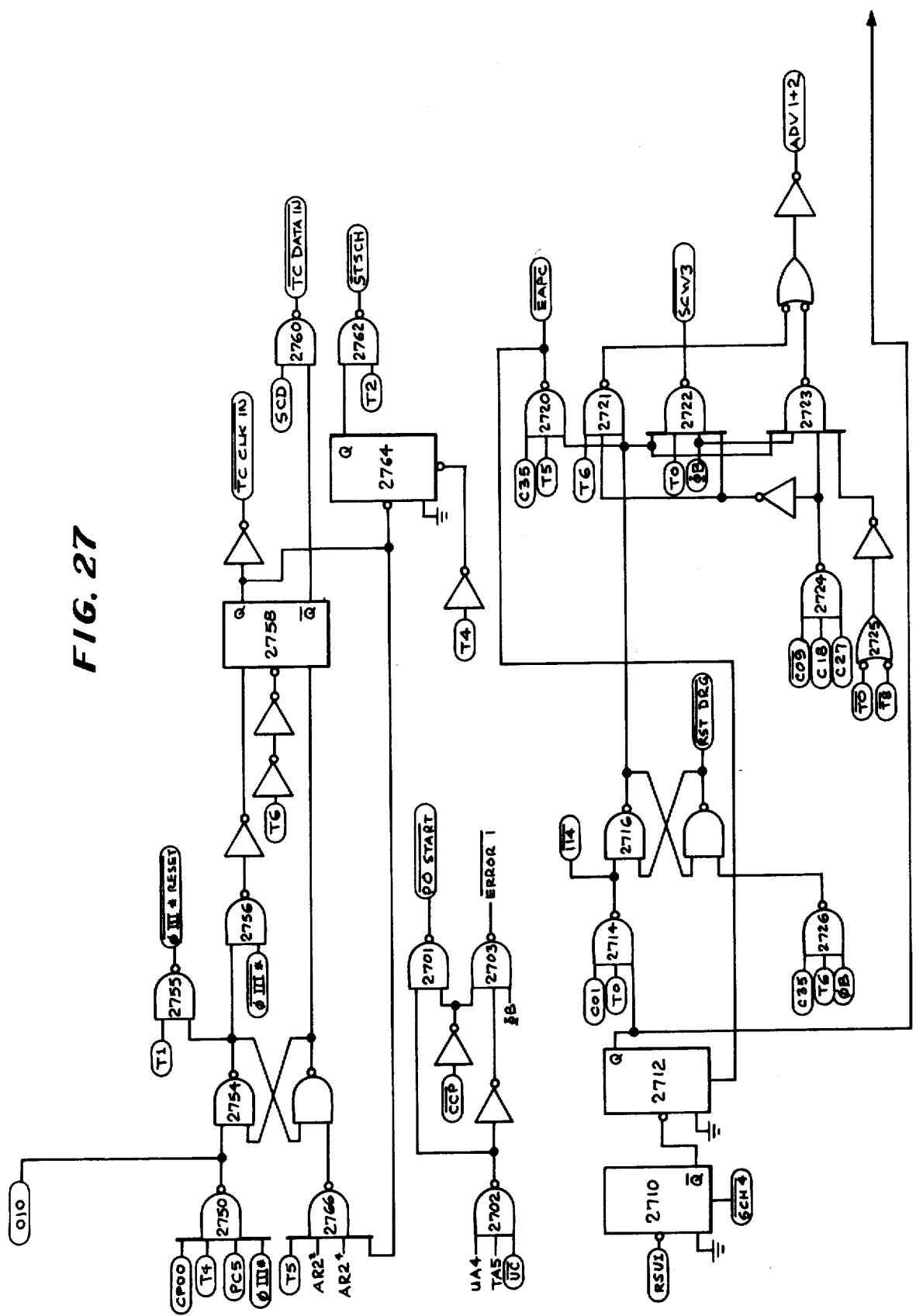
FIG. 27 is a logic diagram of the patient charge search control logic and of the totals data erase logic.
Figure 34:
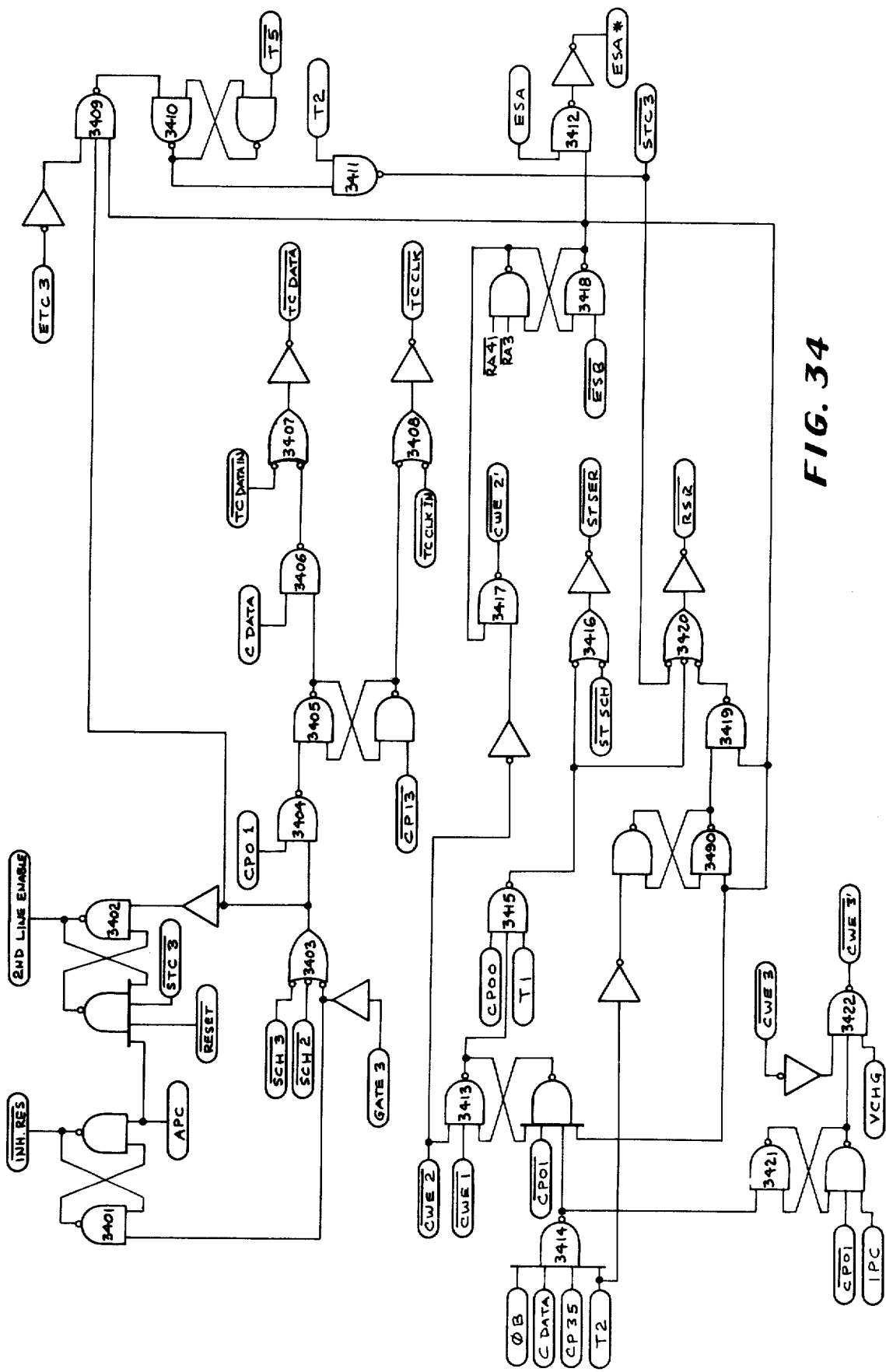
Figure 35:
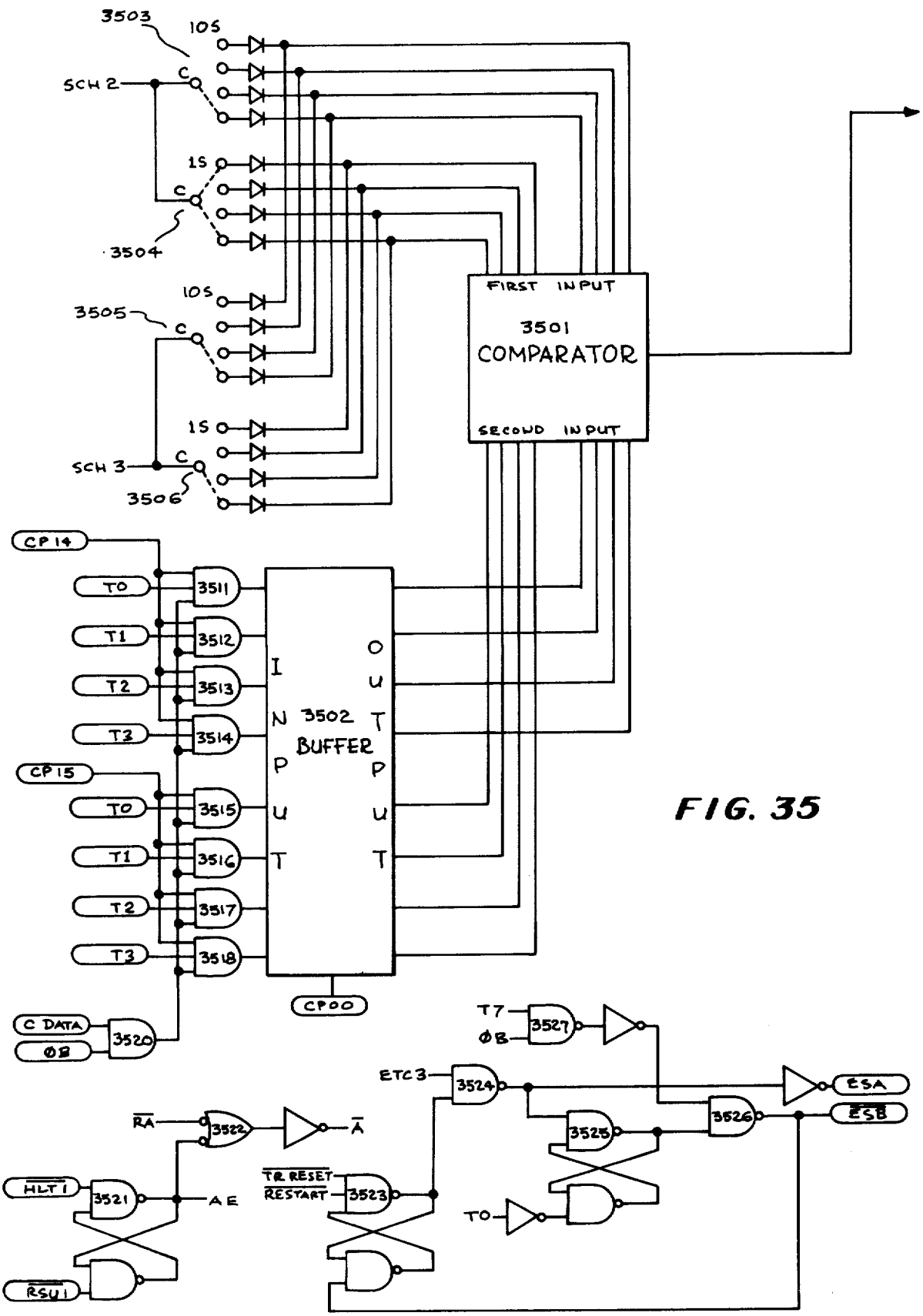

FIG. 27, at the top, shows the logic circuitry which controls patient charge search procedure. A PCS signal, generated by a bistable 3015 (FIG. 30), and a PHASE III* signal, generated by a PHASE III* flip-flop when the patient charge search request has been completely stored into the core memory, enable the gate 2750 during the T4 part of a CP00 timing interval to generate a 010 signal and to set a bistable 27511. The 010 signal sets the core address register to octal location 010. The output signal from the bistable 2754 enables the gate 2755 to generate a PHASE III* RESET signal which clears the PHASE III* flip-flop. This PHASE III* flip-flop is not disclosed in the present application, but is shown in the Phillips, et al. patent (Phillips, et al. U.S. Pat. No. 3,597,742, flip-flop 2116 in FIG. 21). When the PHASE III* flip-flop is cleared, the inverted PHASE III* signal is combined with the output signal from the bistable 2754 by a gate 2756 to produce a signal that enables a flip-flop 2758. The flip-flop 2758 is then toggled into the Q state by the next T6 timing pulse. The output signal from the flip-flop 2758 is called the TCCLKIN signal. This signal causes the patient number stored in the core storage area to be transferred into the shift register 3118 (FIG. 31). The TCCLKIN signal passes through the gate 3408 (FIG. 34) and causes TCCLK signal to be generated. This signal enables the core address register to advance one location during each character timing interval, and also causes the contents of these locations in the core memory to be read out during each timing interval. The TCCLKIN signal generated by the flip-flop 2758 enables the gate 2760 to pass the SCD (serial core data) signal into a TCDATAIN signal. This signal passes through a gate 3407 (FIG. 34) and becomes the TCDATA signal. The TCDATA signal flows through a gate 3117 (FIG. 31) and into a 96 bit shift register 3118. Simultaneously, the TCCLK signal generated by the gate 3408 (FIG. 34) passes through a gate 3112 (FIG. 31) and enables PHASE B pulses to be applied to the shift register 3118 as shift pulses. In this manner, the patient number and data is read out of the core memory and into the shift register 3118. When the patient number has been completely read out of core, the core address register generates signals $AR2^2$ and $AR2^4$, indicating it is at an octal address 022. These signals cause a gate 2766 to reset the bistable 2754 during a T5 time interval, thus terminating the transfer of data into the shift register 3118. When the output signal from the flip-flop 2758 terminates, it toggles a flip-flop 2764 and enables a T2 timing signal to pass through a gate 2762 and generate an STSCH (start search) signal. The flip-flop 2764 is then cleared by a T4 timing pulse.

The patient charge search procedure is initiated by the STSCH signal. This signal passes through a gate 3416 (FIG. 34) and causes an STSER signal to be generated. The STSER signal sets a bistable 3105 (FIG. 31) and initiates a search through the charge information storage area for all charge items containing the patient number stored in the shift register 3118. The details of the search procedure will be described below in the section dealing with the all patient charges search. Whenever a location is found containing the specified patient number, a bistable 3122 generates a signal that partially enables the two printout marking gates 3125 and 3126. The gate 3125 is disabled by the absence of an APC signal, but the gate 3126 is enabled by the flip-flop 3127. This flip-flop is set by a CTR1 pulse which is generated at the start of the all patient charges search by a gate 3106. Flip-flop 3127 is enabled by the PCS signal generated by the bistable 3015. The gate 3126 causes a marker to be placed in the 4th bit position of the 13th character slot of each location within the charge information storage area containing the specified patient number. Locations so marked are routed to the cashier's office teleprinter and are printed out in a list.

The CWE signal generated by the gate 3126 is fed to a gate 3312 which causes a printout marker to be placed in a manner which will be explained in more detail below.

The PCS signal is generated by a bistable 3015, shown in FIG. 30. The bistable 3015 is set up by a gate 3016, when that gate is enabled by the presence of a U2C (U2 control patient charge search request) signal, an inverted CL0* signal which indicates that no other search of the charge information storage area is in progress, and a signal generated by a gate 3013 when the input data which included the U2 control information has been stored in the core memory. If some other search of the charge information storage area is in progress, the CL0* signal is present and inhibits the gate 3016 from causing the bistable 3015 to initiate a patient charge search. In this case, a gate 3012 generates a BYP2 signal. This signal sets a bistable 3025, generating a BYPS1 signal. This signal is fed back to the data collection part of the system and instructs the system to leave this search request stored in the input buffer delay line until a later time when the charge information storage area is no longer occupied with another search.

Two other conditions will cause the BYPS1 signal to be generated. If a U1 nursing station work list search request is received while another U1 search is in progress, a BYP1 signal is generated by a gate 3011 and fed to the bistable 3025. If a charge or inventory information message including an R control character is received at a time when the charge information storage area is completely full, a BYP3 signal is generated by a gate 3024.

When a U1 control nursing station work list request is received by the system, a *B signal is generated by the circuitry of FIG. 1. This signal toggles a flip-flop 3010 and partially enables a gate 3011. If another request for a nursing station work list including a U1 control character is then received, the gate 3011 is enabled by the U1C signal and also by the signal generated by the gate 3013, and causes the second list request to be bypassed temporarily. The flip-flop 3010 remains set until a gate 3014 allows a PHASE A timing pulse to clear the flip-flop 3010. This usually happens at the end of a search when the EOS signal is generated by the time and date calendar circuit. The EOS signal passes through a gate 3005 and enables a PHASE B timing signal to pass through a gate 3006 and clear a flip-flop 3007. The flip-flop 3007 and the signal generated by the gate 3005 then enable the gate 3014 to pass a PHASE A timing pulse which clears the flip-flop 3010. In a case where no beds are found during a nursing station work list search, the termination of the B* signal toggles a flip-flop 3002, partially enabling a gate 3004. A flip-flop 3003 will have been previously set by the *B signal, the U1C signal, and a BT0 beginning of first track timing signal, which all enable a gate 3001. These two flip-flops allow a T1 timing pulse to pass through a gate 3004 to the gate 3005 and initiate a clearing of the flip-flop 3010 unless the flip-flop 3003 is cleared by the DOR signal generated when a location is marked for printout. The gate 3009 allows the flip-flop 3007 to be set by an NS signal when a printout marker is encountered, thus allowing the EOS signal to act immediately upon the gate 3014. Usually, the EOS signal will pass through the gates 3008 and 3009 and immediately toggle the flip-flop 3007 as soon as it is received.

The BYP3 signal is generated by the gate 3024 whenever an R control character accompanies a set of input data at a time when a bistable 3023 is set. The bistable 3023 is set by a gate 3022 whenever an LLA (end of last charge information storage area track) timing signal comes before a CUL (load charge data onto drum) signal, indicating that the charge information storage area is full. Thus, the BYP3 signal causes charge input data to be bypassed when the charge information storage area is filled to capacity. The bistable 3023 is reset by the APC signal when the day's charges are read out and the auxilliary storage track is made available to incoming charge data.

ALL PATIENT CHARGES SEARCH CONTROL LOGIC

An important feature of the present system is the ability to sort out the day's charges by patient and to produce a complete listing of all the charges allocable to each patient at the end of the day. The logic which controls this operation is primarily disclosed in FIGS. 31 to 35, although various small sections of this logic appear in many other figures.

The all patient charges search procedure is initiated by depressing a pushbutton 3201. This sets a bistable 3202 and generates an APCE (APC enable) signal). The APCE signal partially enables a gate 3204. The gate 3204 then sets a bistable 3203 during the first T2 bit timing period when the CL0* signal is not present. It will be remembered that the CL0* signal indicates when some other charge information storage area search in in progress. The CL0* signal is generated in FIG. 25 by the gate 2503.

The bistable 3203 generates an APC (all patient charges) signal. This signal initiates the all patient charges search procedure.

The first step in the all patient charges search procedure is the printout out of the days' totals. The APC signal is fed to FIG. 5, and it causes the gate 557 to generate an APC* signal. This APC* signal sends an inquiry to the business office teleprinter, and initiates a *1 search procedure in the manner described above. This *1 search signal, the output of the flip-flop 540, and the APC* signal are then combined by a gate 541 to form an INH-APC (inhibit APC) signal. This signal is fed to the arithmetic unit, FIG. 22, where it causes the AP signal to be generated and causes the arithmetic unit to perform the necessary calculations to the totals data for printout, as explained data. When the arithmetic unit has finished this task, the 2ND 1/2 signal and the AP signal enable the gate 2820 shown in FIG. 28 to pass a C34 timing pulse to set a bistable 2822 and initiate the printout of the totals data. The output signal from the bistable 2822 enables the gate 2824 to set a bistable 2830 during each REV 3, while the 11th storage location in a track of the charge information storage area is being scanned (as determined by the signals TA1 and UA1), at the start of the 35th character. The bistable 2830 is then reset by a C36 timing signal. Thus, the bistable 2830 is open for exactly 1 character timing interval during REV 3. In generates an RA 3 signal which causes a work of data to be read out of the core memory. The core memory was previously set to the octal address 110 by the gates 2825, 2826, and 2827 which were enabled during T4 and T6 timing intervals by the gate 2820. The gate 2825 and 2826 set the core address register to location 000, and the gate 2827 advanced the core address register to location 110. This two step procedure is resorted to as a way of simplifying the core addressing procedure. The output signal from the bistable 2830 enables the gate 2832 to set a bistable 2834 during the last bit of a C35 timing interval. The bistable 2834 remains set for exactly one character count, and is reset by a gate 2836. During this period, the bistable 2834 generates a TOTEN signal which enables the circuitry of FIG. 5 to read one character out of the core memory and into the shift register 641 (FIG. 6). This bistable also generates a signal that is passed through a gate 2840 and enables the gate 2842 to channel the SCD (serial core data) signal into the TOTDATA (totals data) signal. This signal is fed through the list output circuitry of FIG. 5 and into the shift register 641 (FIG. 6).

As mentioned above, the totals data, and also the various other characters which are printed out when the totals data is printed out, are stored in adjacent locations in core. Thus, the circuitry of FIG. 28 continues to read out one word of core information which each three revolutions of the drum as indicated by the REV 3 signal. When the core address counter reaches the octal address 200 as indicated by an AR $2^7$ signal, a gate 2852 generates a TOT COM (totals printout complete) signal which reset the bistable 2822 and also passes through the gate 699 and initiates a time and data printout.

Since the totals data as stored in core does not include decimal points, it is necessary to provide a way of inserting decimal points into the printout. This task is performed by a counter 2850. The counter starts at a count of 0 when the first character in the total data printout is printed. It advances one count each time is receives a pulse from the gate 2836, and thus counts the characters as printed out. After the 10th character is printed out the counter 2850 generates a DECF signal, which disables the gate 2840 and prevents serial core data from being transferred to the output logic shown in FIG. 5. In its place, the DECF signal causes the output logic circuitry of FIG. 5 to generate a teleprinter character representing a decimal point, as was explained above. The counter 2850 repeats this operation after each 14 characters. The totals data is arranged in core storage so that a decimal point is required every 14 characters.

The core address register is advanced by an IPI signal generated by a gate 2844 and passed through a gate 2846 during the T6 timing interval while data is being transferred to the list output circuitry of FIG. 5. The DECF signal suppresses the IPI signal whenever it occurs. A gate 2848, which also can generate an IPI signal, is used to keep the decimal point which accompanies monetary data into the system from being stored in the charge information storage area. The gate 2848 adds an extra address counter advance pulse just at the right time to cause the decimal character to be skipped.

The TOT COM signal generated by the gate 2852 is sent back to FIG. 32 and sets a halt bistable 3207. The TOT COM signal also initiates a time and date printout. When the time and date printout is complete, the calendar circuit generates an EOS signal which sets a bistable 3205 and causes the generation of a Z signal. The Z signal generated by the bistable 3205, and the signal generated by the halt bistable 3207, are combined by a gate 3219 and used to produce an enabling signal for a gate 3220. The output signal from a gate 3219 is also used to illuminate a halt signal light, indicating to a supervisory employee that the system has stopped and will not restart until commanded to do so. The APC procedure then stops, giving the supervisory employee a chance to study the totals data and to prepare for the next part of the APC procedure.

When the supervisory employee is ready to resume the APC printout, he depresses a resume pushbutton 3223. This button, together with the signals from the bistable 3205 and 3207 enable a gate 3213 to generate a signal which passes through the gates 3214, 3215, and 3217, and toggles a flip-flop 3218. The flip-flop 3218 generates an enabling signal which is fed to four different gates in FIG. 33. This signal passes through the gate 3301 because this gate is enabled by the APC signal and by the absence of an IPC signal. The gate 3301 then generates a RSU1 signal. This signal initiates a search for all charges relating to hospital in patients as indicated by the information stored in the bed information storage area. This signal sets the bistable 3302 and causes the generation of a NEXT CH signal. It also passes through a gate 3206 and clears the halt bistable 3207. The flip-flop 3218 is toggled back into its normal state by a T2 timing signal which passes through the gates 3216 and 3217. The $\overline{Q}$ signal from the flip-flop 3218 then clears the Z bistable 3205.

The RSU1 signal also causes the totals figures to be erased from the core memory. The RSU1 signal toggles a flip-flop 2710 (FIG. 27) which in turn toggles a flip-flop 2712. The flip-flop 2712 initiates the erasure of the previous day's totals. The flip-flop 2710 remains set for the rest of the APC procedure so that the new totals data for the next day cannot be accidentally erased. At the end of the APC procedure, a SCH4 signal clears the flip-flop 2710. The details of this erasure procedure are described elsewhere in this specification.

The NEXT CH (next charge) signal is fed back to the bed information search logic, and initiates a search through the bed information storage area for a patient number, as described above. Each time a new patient number is encountered, the bed information search logic circuitry of FIG. 1 generates a UCPN (update patient charge number) signal which passes through a gate 3114 at the start of a C21 character timing signal and sets the bistable 3113. The bistable 3113 remains set until it is cleared by a C33 character timing signal. The bistable 3113 causes a gate 3115 to pass data from the bed information storage area through a gate 3117 and into a patient number shift register 3118. Simultaneously, the bistable 3113 sends a signal through the gate 3112 that enables the gate 3119 to pass PHASE B timing pulses to the shift register 3118. These pulses cause data to be read into the shift register. If the patient number is one for whom charges have not been printed out before, the logic of FIG. 1 generates an NOCP signal which clears the bistable 3302, thus terminating the NEXT CH signal. The NC signal is also terminated, thus disabling a gate 3303. If the charges for this patient have already been printed out, the NOCP signal is not generated. In this case, the next patient number is read into the shift register 3118, and the search continues until a patient number is found for whom the charges have not bee printed out.

When a new patient number has been found, the location where it was found in the bed information storage area is marked for printout, as explained above. The printout includes the patient number, the bed number, and the cost of the bed for the day. When the printout is initiated, the logic circuitry FIG. 3 generates a CIP LIST signal. This signal, plus an F27 signal generated by the bed information format generator after the above information has been completely printed out, enable a gate 3111 to set a bistable 3105. At the end of the current drum revolution, as indicated by an MS signal, the output signal from the bistable 3105 is passed through a gate 3106 and sets the bistable 3107, generating an SCH 1 signal. This signal initiates the search of the charge information storage area for charges relating to the patient specified by the number in the shift register 3118.

The SCH 1 signal is fed into a gate 3129 and causes the generation of a SEARCH signal. This signal cuases the counter which controls the scanning of the charge information storage area to advance one track at the end of each revolution of the magnetic drum. The SEARCH signal also sets a bistable 3145 which partially enables a gate 3146. When the SEARCH signal is terminated, the gate 3146 sets a bistable 3142 which enables a bistable 3144 to be set at the end of the next revolution of the drum. The bistable 3144 then generates the SCH5 signal which initiates a search of the charge information storage area for printout markers. Thus, when the SEARCH signal terminates after the charge information storage area has been searched, a SCH5 printout of data from the charge information storage locations that were marked during the search is automatically initiated.

Prior to the initiation of the SEARCH signal the charge information track counter is reset to the first track by a TR RESET (track reset) signal. This signal is generated by passing a CTR1 signal from the gate 3106 through a gate 3315. The TR RESET signal sets the bistable 3316 and causes the generation ofan SCHR (search reset) signal which actually resets the track counter. The SCHR signal is terminated by a CP10 timing signal. The TR RESET signal is also used to set a bistable 3523, which enables the gate 3524 to pass an ETC 3 signal when that signal is generated as the search procedure reaches the end of the last track in the charge information storage area. The gate 3524 then generates an ESA signal and sets a bistable 3525 so that a much shorter duration ESB signal can be generated by the gate 3526 during the PHASE B part of a T7 bit timing interval. These two signals indicate when a search has come to the end of the last track. The bistable 3523 is reset by the ESB signal, and the bistable 3525 is reset by a T0 bit timing pulse.

The searching procedure comprises feeding all patient number data from the charge information storage area into a comparison gate 3120 and comparing it with the patient number stored in the shift register 3118. If the numbers agree, the location is marked for printout. The comparison operation is controlled by a flip-flop 3109. The flip-flop 3109 is cleared by a CP01 timing pulse which passes through a gate 3110 whenever the SCH 1 signal is present. It is set by a PHASE B timing pulse after being enabled by the T7 part of a CP12 timing signal which comes through a gate 3108. When the flip-flop 3109 is cleared, it enables the gate 3121 to pass the results of the comparison test to a bistable 3122, enables the recirculation gate 3116 and allows data to recirculate through the shift register 3118, and also passes through the gate 3112 and enables the gate 3119 to pass PHASE B shift pulses to the shift register 3118. If the comparison fails, bistable 3122 is clared and disables a gate 3125 thus preventing a printout marker from being placed in the charge information storage area. The bistable 3122 is normally placed in the clear state by a gate 3123, but it is set up during the T7 part of a CP00 timing signal by a gate 3124 whenever the SCH1 signal is present. The gate 3125 then generates a CWE3 signal which passes through gates 3422 and 3312 and causes the generation of a WEM (write enable main) signal. This WEM signal is passed through the gate 2533 (FIG. 25) and causes the generation of the MWEC signal which writes data into the charge information storage area. The CWE3' signal generated by the gate 3422 also passes through a gate 3306 and causes a bit of data to appear in the DATA EN signal. This is the signal that is actually written into the charge information storage area when the drum logic is enabled to write by the MWE signal. The DWCM signal generated by the gate 2532 in FIG. 25 also passes through this gate 3306.

The searching procedure continues till the entire charge information storage area has been searched. At the end of the search, an ETC 3 (end of last track) signal passes through a gate 3131 and generates an RS1 signal which clears the bistable 3107 thus terminating the search procedure. This signal also terminates the SCH 1 signal, which in turn causes the gate 3129 to terminate the SEARCH signal. As noted above, this automatically causes the bistable 3144 to generate an SCH5 signal which initiates a printout of the data which has been found and marked.

The data found is printed out next. The bistable 710 (FIG. 7), which generates the BO (business office charge list) signal has already been set up at this point by the CIP LIST signal ANDed together with the F27 signal generated at the end of the patient number printout. The BO signal causes the LIST signal to be generated by the logic shown in FIG. 7. This LIST signal partially enables the gate 712. The gate 712 is used to tell when a complete printout marker search of the charge information charge storage area has been made without any new printout markers having been found. The gate 712 is also partially enabled at the end of each search by the ESA signal generated by the gate 3524. If a printout marker has been encountered during a search, the gate 712 is disabled by the CBFR signal generated by the gate 716, and is also disabled during the printout of time and data information by an LADV signal generated by the time and date calendar circuitry. When a search finally reaches the end of the charge information storage area without encountering a printout marker, the gate 712 sets a bistable 713 and causes the generation of an RONC (request next charge) signal. This signal passes through a gate 3212, which is enabled by the halt bistable 3207, and then passes through the gates 3214, 3215, and 3217 to toggle the flip-flop 3218. The flip-flop 3218 then enables the gate 3301 once again and causes another RSV1 signal to be generated. This initiates another search of the bed information storage area for the next in patient charge number.

During the SCH5 search for printout markers, the track counter is reset by a CTR 6 signal generated by the gate 3143 at the start of the SCH5 procedure. This signal is fed through the gate 3315 and causes the bistable 3316 to generate the SCHR (search reset) signal, which resets the track counter.

The above search process is repeated until a search for charges have been made for all in patients listed in the bed information storage area. When a search of the bed information charge storage area finally does not come up with a new patient number, the NOCP signal is not generated to reset the bistable 3302, and the NC signal remains present at the end of the search. These two signals enable a gate 3303 to pass an ET1 signal at the end of the track and generate an HLT1 (halt) signal. This HLT1 signal passes through gates 3208 and 3209, and sets the halt bistable 3207. The output pulse from the gate 3209, called a HLTT pulse, is counted in a counter comprising two flip-flops 3241 and 3247, whose function will be described below. A flip-flop 3211 then disables the gate 3209 and prevents the generation of any further HLTT pulses while the halt bistable 3207 remains set. The HLT1 pulse also sets a bistable 3304 which generates an IPC (in patient search complete) signal. This signal is used to disable the gate 3301, preventing a further search for in patient charges, and to enable the gates 3305 and 3307. The next time the flip-flop 3218 generates a pulse, it passes through the gate 3307, rather than the gate 3301, and initiates a search for out patient charges. The gate 3305 allows an ET2 pulse to reset the bistable 3302.

HLT1 signal generated by the gate 3303 is also fed through logic shown at the bottom of FIG. 6 to the time and date calendar circuit and initiates a time and data printout. When the time and date calendar circuit has finished printing out the time and date, it returns the EOS signal which sets the bistable 3205. The Z signal from the bistable 3205 and the signal from the halt bistable 3207 once again enable the gate 3219 to illuminate the halt signal and stop the APC procedure.

The next section of the APC procedure is initiated when a supervisory employee again presses the resume button 3223. This again causes the flip-flop 3218 to generate a signal. This time that signal, plus the IPC signal generated by the bistable 3304, combine and enable the gate 3307 to generate an RSU2 signal. This signal is fed back through the gate 3206 and clears the halt bistable 3207. The bistable 3205 is then again cleared by the flip-flop 3218. The RSU2 signal then initiates a search for out patient numbers and for charges allocable to out patients.

The RSU2 signal sets a bistable 3308 and enables a gate 3309 to allow a MS (master strobe) timing pulse to generate a CTR2 signal and set a bistable 3310. The bistable 3310 generates an SCH 2 signal which initiates a search of the charge information storage area for out patient members. The CTR2 signal is also sent to the gate 3315 and is used to reset the track counter and to set up the ESA signal. The SCH2 signal causes the gate 3129 to generate the SEARCH signal which allows the track counter to advance after each track is scanned, and to prime the SCH5 bistable 3145 in the manner described above. The SCH 2 signal enables the two tie points 3503 and 3504 to feed a BCD (binary coded decimal) number into a comparator 3501. This BCD number is a false nursing station number which is assigned to all out patients for example, the number 89, which is 1000, 1001 in BCD form. This number is permanently set when the system is installed, and is not usually changed thereafter.

The SCH 2 signal passes through a gate 3102 and partially enables the gate 3101. The remaining inputs to the gate 3101 are an output signal from a comparator 3501, and a CP 18 timing signal. As the charge information storage area is scanned, the charge information flows through a gate 3520 and into an 8-bit buffer 3502. Gates 3511 through 3518 cause the contents of the first four bits in the fourteenth and fifteenth character slots of each charge information storage location to be loaded into the buffer 3502. These character slots contain the nursing station number data, so the two digits of the nursing station number are loaded into the buffer 3502. When a nursing station number presented by the buffer 3502 matches the number presented by the tie points 3503 and 3504, a comparator 3501 enables the gate 3101 to pass a CP18 timing pulse which sets up a bistable 3103. The bistable 3103 then enables a gate 3104 to generate a CWE2 (charge write enable) signal which sets the bistable 3413 shown in FIG. 34, and enables the gate 3415 to generate a signal which passes through a gate 3416 and becomes the ST SER (start search 1) signal. This signal sets the bistable 3105 and initiates a SCH1 search for all items containing this same patient number. The bistable 3413 is reset however before the gate 3415 can generate an STSER signal, by a gate 3414 if a printout marker is found in the second bit position of the 35th character of this location, indicating that this out patient number has already been included in an APC printout. The bistable 3413 is normally reset by a CP01 timing pulse.

While the out patient nursing station number search was being carried out during the SCH2 procedure, patient numbers from the charge information storage area were continually read into the shift register 3118. Data from the charge information storge area flowed through the gates 3406 and 3407, generating a TCDATA signal. This signal was fed through the gate 3117 and into the patient number shift register 3118. Simultaneously, a TCCLK signal was generated by a bistable 3405 and was passed through a gate 3408 and a gate 3112 to enable PHASE B shift pulses to pass through the gate 3119 and load the shift register 3118. The bistable 3405, which generated the TCCLK signal and which also enabled the charge information data to flow through the gate 3406, was set during a CP01 timing interval by the SCH 2 signal which passed through gates 3403 and 3404. The bistable 3405 is reset by every CP13 timing pulse, so only the patient charge number data is read into the shift register 3118.

When the ST SER signal is generated by the gates 3415 and 3416, simultaneously, the output from the gate 3415 flows through a gate 3420 and becomes an RSR signal. This signal clears the bistable 3310, thus terminating the SCH2 signal while the SCH1 search is carried out. When the SCH1 search is completed, a search 5 marker search and printout is automatically initiated in the manner described above. The SCH 2 signal, however, passed through a gate 3403 and set a bistable 3402 which generates a 2ND LINE ENABLE (two line printout enable) signal. This signal causes the patient number included in the first item marked for printout to be printed out along with the usual charge data, under the control of the charge information printout format generator. The bistable 3402 is reset after this first data item has been printed out by the RESET signal generated by the gate 1434 (FIG. 14) at the end of the first line of printout. Thus, each listing of out patient charges is preceeded by the out patient's patient number.

After the search 5 printout is completed, the RQNC signal is again generated by the bistable 713 (FIG. 7). This signal, as before, passes through the gates 3212, 3214, 3215, and 3217 and sets the flip-flop 3218. The flip-flop 3218 generates a signal that passes through the gate 3307 (the bistable 3304 still generates the IPC signal which enables the gate 3307) and initiates another SCH2 search for another out patient patient number.

When all outpatient charges have been found and printed out, a final SCH2 search is made of the charge information storage area during which the bistable 3413 is never set. The gate 3415 never causes the gate 3420 to generate an RSR signal, and the bistable 3310 remains set at the end of the search. At the end of the search, the ESB signal generated by the gate 3526 sets a bistable 3418 and enables the ESA signal, generated by the gate 3524, to pass through a gate 3412 and produce an ESA* signal. This ESA* signal, along with the output signal from the bistable 3310, causes a gate 3313 to generate an HLT2 signal and to set a bistable 3314. The HLT2 signal passes through the gate 3208 and sets the HALT bistable 3207. Meanwhile, the SCH2 signal, which is still being generated by the bistable 3310, passes through a gate 3403, and partially enables a gate 3409. Another input of the gate 3409 is enabled by the bistable 3418, that was set up by the ESB signal. The final input to the gate 3409 is enabled by an ETC3 pulse which occurs at the end of the last track of the charge information storage area. The gate 3409 then sets the bistable 3410 and causes the bistable 3410 to allow a T2 pulse to pass through a gate 3411 and become an STC3 signal. This STC3 signal is fed back through the logic shown at the bottom of FIG. 6 to the time and date calendar circuitry, and initiates a printout of the time and date. The STC3 pulse also passes through the gate 3420 and becomes an RSR signal, which clears the bistable 3310 and terminates the SCH2 signal. When the printout of the time and date is completed, the EOS signal generated by the time and date calender circuitry sets the bistable 3205 and causes the Z signal to be generated once again. This signal, and the output signal from the halt bistable 3207, cause the gate 3219 to illuminate the halt signal. The system once again stops the APC search, and remains on standby until the resume button 3223 is again depressed by a supervisory employee.

When the resume button is depressed, a search almost identical to the last search is initiated for all charges relating to out house patients. The only difference between this search procedure and the last search procedure is that this time a search is made for items containing a different nursing station number, for example 88 (1000,1000 in BCD form) from the one used to designate outpatients. The gates 3317, 3319, and 3322 perform the same task carried out by the gates 3307, 3309, and 3313. Similarly, the bistables 3318, 3320 and 3323 perform the same tasks carried out by the bistables 3308, 3310, and 3314. At the end of this search, a halt again is initiated, and the bistable 3323 will be set. The search for a new out house patient number is called the SCH3 search, and is controlled by an SCH3 signal.

A final search is then made for all the charges which were not printed out in one of the previous searches, and is called the miscellaneous charge search. This search is initiated when the resume button 3223 is depressed. An RSU4 signal generated by a gate 3324 clears the halt bistable 3207, and sets the bistable 3325. The bistable 3325 enables the gate 3326 to allow the next MS pulse to pass through a gate 3326 and become an CTR5 pulse which sets a bistable 3327. The CTR5 signal performs the same task performed by the CTR2 signal discussed above. The bistable 3227 generates a GATE 3 signal which initiates the final search. This last printout includes all items that have not been previously marked as printed out by a marker bit placed in the second bit location within the 35th character slot, and which contain any "1" in the 12th character slot. This latter test prevents a printout from being made of totally blank charge data. A flip-flop 3341 checks the 12th character slot of each charge storage location for the presence of any "1" bits. Data from the charge information storage area is fed through a gate 3248 during the CP12 timing interval. The gate 3248 is periodically enabled by PHASE B timing pulses. If any bits are encountered, the flip-flop 3341 is cleared by the output signal of the gate 3248. The flip-flop 3341 is initially set by a CP35 timing pulse. The output signal from the flip-flop 3341 enables a gate 3329 to generate an output signal during the T2 part of character timing interval CP35, thus partially enabling a gate 3330 at this time. Data from the charge information storage area is passed through a gate 3328 and into the remaining input of the gate 3330. The gate 3328 is enabled by the GATE 3 signal generated by the bistable 3327, and also by PHASE B timing pulses. Note that the CDATA (charge data) signal fed into the gate 3328 is inverted, so this gate is enabled by the absence of a "1" bit, rather than by the presence of such a bit. When such a bit is found to be absent, the gate 3330 is enabled to set a bistable 3331. This bistable enables a gate 3332 to generate a CWE1 signal. The CWE1 signal sets the bistable 3413. If the storage location does not contain a marker in the second bit position within the 35th character slot, the bistable 3413 initiates a SCH1 procedure and causes a list to be formed including charge information from all locations having the same patient number as the location just found. If the location does contain a marker in the second bit position within the 35th character slot, the bistable 3413 is cleared by the gate 3414, and the GATE 3 search procedure continues. After each printout of a group of charges, the GATE 3 search is recommenced in the same manner that the SCH2 and SCH3 searches are recommenced. The GATE 3 search is ultimately terminated in the same way that the SCH2 and SCH3 searches are terminated.

The SCH4 signal generated by a bistable 3339 also clears the three bistables 3207, 3202 and 3203 and terminates the APC operation. These bistables are cleared by an SCH4 ST signal which for the purposes of this application can be considered identical to the SCH4 signal generated by the bistable 3339. The bistable 3203 does not clear directly by the SCH4 ST signal, but is cleared indirectly by the bistable 3202. The SCH4 signal also disables the flip-flop 3218 thus disabling the halt push button 3210 and the resume push button 3223. The bistable 3205 which generated the Z signal is cleared by the bistable 3202.

The SCH4 and the SCH4 ST signal also initiate an erasure of printout markers from the bed information storage area. The SCH4 ST signal sets the bistable 3226 which enables the gate 3227 to allow the next BTO timing signal to set a bistable 3228. It will be remembered that the BTO timing signal occurs when the beginning of the first track in the bed information storage area is being scanned. The bistable 3228 then enables the gate 3229 to generate the WEBIP pulses during the TI part of each C39 timing interval. This signal is fed to the logic circuitry of FIG. 4 where it causes the markers located in these areas to be erased. A gate 3225 is enabled by the bistable 3228 to allow an ET1 timing pulse to clear the bistable 3226. An ET2 timing pulse, which is generated as the end of the last track in the bed information storage area that is scanned, clears the bistable 3228 and terminates this erasure process.

Elements 3230 to 3232 allow departmental tally searches to be performed after the APC searches are finished and before the charge information storage area is erased. The SCH4 signal generated by the bistable 3335 enables a flip-flop 3230 to be toggled by the Z signal generated by the bistable 3205 when the time and date circuitry returns an EOS pulse to the system. The flip-flop 3230 sets a bistable 3231, and is then cleared by an MS pulse. The output signals from the flip-flop 3230, from the bistable 3231, and from the bistable 3233 then enable the gate 3232 to generate an INH CLO signal. This signal is fed back to the tally search control logic where it enables tallies to be carried out in the manner explained above. The gate 3232 is disabled during the time when the charge information storage area is erased by the bistable 3231 which is cleared by the SCH4 ST signal. The gate 3232 can also be inhibited by the bistable 3233 in case a repeat search of the charge information storage area from the miscellaneous charges is performed.

At any time, a search may be halted by depressing halt push button 3210. The signal generated by this push button sets the halt bistable 3207, and also passes through the gate 3208 and 3209 and causes an HLTT signal to be generated. The flip-flop 3211 is set by this procedure, and prevents the halt signal from being generated the second time, if the halt button 3210 is depressed the second time. This HLTT signal toggles the flip-flop 3241 into the Q state. The system continues printout the current list of charges which is has found. When the RONC signal comes back into the gate 3212 to request a search for the next set of charges, the signal is prevented from passing into the gate 3212 by the signal from the halt bistable 3207. The system then comes to a complete stop. The system can be restarted at the same place by pressing the RESUME push button 3223. This generates a substitute RQNC signal, which begins the search at the same place where it left off.

During any halt, whether in the middle of or at the end of a search, that search can be restarted by depressing a RESTART push button 2234. The signal from this push button passes through a gate 3220 and sets the bistable 3221 and also toggles the flip-flop 3222. The bistable 3221 merely prevents a second pulse from the switch 3224 from toggling the flip-flop 3222 before the system resumes. The gate 3220 prevents a signal from the push button 3224 from setting the bistable 3221 when the system is not halted. The flip-flop 3222 clears the flip-flop 3240 and causes the flip-flop 3240 to enable the gate 3249 to pass an MS pulse. This MS pulse becomes an RST signal which clears the flip-flop 3222, sets the bistable 3237, and partially enables a whole series of gates 3250, 3252-3255, and 3243. The particular gate which is totally enabled depends upon the state of two flip-flops 3241, and 3247. The state of these flip-flops, in turn, depends on exactly what phase of the all patient charges search is in progress.

If the RESTART push button 3224 is depressed after the totals data has been printed out, it will allow a second printout of the totals data. The flip-flop 3241 and 3247 are cleared before the start of the all patient charges procedure by the APC signal generated by the bistable 3203. After the totals data printout, these flip-flops will still be cleared and will generate inverted RA and RB signals.

The inverted RA and RB signals cause the gate 3250 to pass the RST signal and generate an RESTART signal which sets the bistable 3523. This initiates the generation of the ESA and the ESB signal, and also the ESA* signals mentioned above, which reset various sections of the system. Simultaneously, these same signals enable the gate 3252 to generate an RA1 signal. This signal is fed back to the bistable 3202 and clears the bistable 3202, thus completely terminating the APC printout procedure. To reinitiate a printout of the totals data, the all patient charge push button 3201 is once again depressed, starting the procedure.

If the RESTART push button 3224 is depressed after a halt in the middle of the in patient APC search, the flip-flop 3240 causes the gate 3249 to generate an RST pulse in the same manner as described above. This time, however, the flip-flop 3241 will be in the Q state because of the HLTT signal generated when the HLT push button 3210 is depressed. The enabling signals generated this time by the flip-flops 3241 and 3247 will be an RA signal and an inverted RB signal. These signals will enable the gate 3253 to generate an RA2 pulse. The RA2 pulse sets bistables 3226 and 3233, and initiates a complete erasure of all printout markers both in the bed information storage area and in the charge information storage area. The resume button 3223 is then depressed to resume the search. The bistable 3521 which is set by the RSU1 signal generated by the gate 3301 when the in patient search is commenced generates an extra A signal which is combined with the RA output signal from the flip-flop 3241 by a gate 3522 and supplied to the two gates 3251 and 3252 to insure that the APC procedure is not restarted ab initio even when the HLTT signal has not toggled the flip-flop 3241.

If the RESTART push button 3224 is depressed during the halt after the in patient charges data has been completely printed out, the same exact procedure is initiated. The flip-flop 3241 is in the Q state generating the A signal, because the HLT1 signal generated by the gate 3303 to halt the operation caused an HLTT signal to be generated. Once again, all printout markers are erased. The system is then restarted by again depressing the resume push button 3223.

Each time there is a halt in the procedure, an HLTT pulse is applied to the flip-flop 3241 and 3247. The gates 3244, 3245 and 3246 interconnect these two flip-flops so that they function as an up-down counter. The direction in which the flip-flops count is determined by the setting of the flip-flop 3240. Usually, the flip-flop 3240 is set, and it causes the flip-flop 3241 and 3247 to function as an up counter. Thus, the second HLTT pulse received either when the HLT button is depressed during the out patient searching interval or else when the HLT2 signal is generated at the end of the out patient charge search interval, the flip-flop 3241 will generate an inverted RA signal, and the flip-flop 3247 will generate a RB signal. If the restart push button 3224 is depressed, these signals will cause the gate 3254 to generate an RA3 signal. Simultaneously, the RSI signal generated by the gate 3249 will pass back through the gate 3243 and add a count to the flip-flop 3241 and 3247. At this moment, however, the flip-flop 3240 is clear and thus the two flip-flops 3241 and 3247 are functioning as a down counter. Thus, the one count that was added to these flip-flops by the HLTT signal is subtracted from their count, putting them back in the status which they occupied before the HLTT signal was generated. The RA3 signal clears the bistable 3314, which may or may not have been set up by the HLT2 signal depending upon whether the out patient charge search was allowed to come to its natural end, or was terminated early by the HLTT push button 3210. This prevents the system from advancing and performing the out patient charge search.

It is also necessary to erase all printout markers which have been applied to in patients so that this search can be reinitiated from the start. The RA3 signal sets the bistable 3418. This bistable enables the gate 3417 to generate a CWE2' signal. The CWE2' signal causes a printout marker to be erased by passing through the gate 3312 and causing the WEM signal to be generated. It will be remembered that the CWE2 signal is generated whenever a location within the charge information storage area is encountered and contains an out patient, or a out house patient nursing station number, whichever number is being used in the current search. In this manner, each time a location containing an out patient number is found, a WEM signal causes the printout marker contained in that location to be erased. Thus, the search for out patients can be resumed ab initio when the resume push button 3201 is depressed.

The restart procedure during the out house patient charges search is initiated almost exactly in the manner described above. The flip-flops 3241 and 3247 will generate RA and RB signals at this time, because they will have stored a total of three HLTT pulses. Thus, an RA4 signal is generated rather than the RA3 signal. This signal passes through a gate 3238 and causes an RA41 signal to be generated. The RA41 signal is used to reset the bistable 3323, and also to set the bistable 3418 to erase the out house patient printout markers.

The present embodiment does not include a restart procedure for reinitiating the final miscellaneous charges search. Such a procedure would be very difficult, because there is no simple way that the printout markers could be erased without erasing all printout markers from the entire storage area. The GATE 3 signal, generated during this final search, sets the bistable 3401 which generates an INHRES (inhibit restart) signal. This signal inhibits the flip-flop 3222 from being toggled in response to depression of RESTART push button. At the end of this last search, a final HLTT pulse advances the count in the flip-flop 3241 and 3247 back to 0, and these flip-flops once again generate inverted RA and inverted RB signals. The HLT4 signal, generated by the gate 3334 at the end of this last search, sets a bistable 3239 which prevents the RST pulses from passing through the gate 3245 and advancing the count within the flip-flop 3241 and 3247 after the procedure is completed. If the RESTART push button 2234 is depressed at this time, it will once again cause the gates 3250 and 3252 to be enabled, and will cause the entire APC search procedure to be started once again from the beginning.

At the end of the final APC search, the charge information storage area will be entirely filled with printout markers. These markers are erased right after the search is completed so that the charge information storage area is ready for tally searches which may be performed next. The SCH4' signal generated at the end of the last search by the bistable 3335 enables the flip-flop 3230 to be toggled by the Z signal generated by the bistable 3205 at the completion of the sign-off time and date printout. The output signal from the flip-flop 3230 sets a bistable 3233 and initiates a complete erasure of all printout markers from the charge information storage area. The flip-flop 3230 is then reset by an MS pulse. When this erasure process is completed, the bistable 3233 is cleared by an ETC3 signal. The output signal from the bistable 3233, from the flip-flop 3230 and from the flip-flop 3231 are then combined to enable the gate 3232 and generate an INHCLO signal which is fed back to the tally search control logic to allow tally searches to be once again initiated. This is the only time during the APC search procedure when a tally search can be run. The INHCLO signal is terminated during the time when the charge information storage area is erased by the bistable 3231 which is set by the SCH4 ST signal discussed above.

The bistables 3304, 3314, 3323, 3335 are interconnected in such a manner that when one is cleared, it clears all the others located below it. In this manner, when an earlier search is initiated, it terminates all later searches.

It was mentioned above that an RSR signal is used to terminate the SCH2 signal and SCH3 signal when an SCH1 signal is generated. An RSI signal generated by a gate 3131 at the end of the last track of the charge information storage area is also used to reset the bistables. These signals are combined to form an RSI or RSR signal which is fed to bistables 3310 and 3320 and to terminate the SCH2 and the SCH3 signals, respectively. This same signal is also fed to the bistable 3327 and is used to terminate the GATE 3 signal.

After the miscellaneous charge search is completed, the bistable 3335 causes a CLEAR READY light 3343 to be illuminated. This light tells the supervisory employee that the printout of the charges is completed, and that the charge information storage area of the magnetic drum may now be cleared of data.

When the supervisory employee is ready to erase all the charge data from the charge information storage area, he closes a clear switch 3342 by inserting a special key into the system panel and turning the key. This key prevents the charge information from being erased by anyone except the person authorized to do so. The output signal generated by closing the switch 3342, the output signal from the bistable 3335, and the Z signal from the bistable 3205 enables the gate 3336 to set a bistable 3337. The bistable 3337 enables the gate 3338 to pass the next MS pulse to a bistable 3339, causing the bistable 3339 to generate a SCH4 signal. This SCH4 signal is fed through the gate 3312 to initiate the WEM signal, which turns on the write amplifier in the charge information storage area. The output signal from the gate 3338 which is called the CTR4 signal, also causes the gate 3315 to reset the track counter to the first track. This same signal sets the bistable 3390 which enables the gate 3391 to pass a DATAAUX signal, carrying the data from the auxilliary storage track of the charge information storage area through the gate 3306 and onto the first track in the main charge information storage area in the form of a CWE5 signal. The bistable 3390 is cleared by the ETC2 signal which comes at the end of the first track, so this data is only wirtten onto the first track of the charge information storage area. The SCH4 signal is terminated when the bistable 3339 is cleared by an ETC3 signal. This signal is generated when the recording head is over the last section of the last track of the charge information storage area. Thus, the SCH4 signal erases the entire drum, and leaves the auxilliary charge data in the first track of the main drum.

While the all patient charge search procedure is carried out, incoming charges are stored in the auxilliary track in the manner described above. It is necessary to prevent the SCH4 signal from occurring at the time when charge data is being read into this auxilliary track. This is down by an XI signal which disables the gate 3338. The XI signal is generated by a gate 2513 shown in FIG. 25. When no information is being read into the auxilliary track, the gate 2510 disables the gate 2513 and causes the two flip-flops 2514 and 2515 to toggle into the $\overline{Q}$ state. Thus, the output of the flip-flop 2515 is high normally. When a CH signal enables the gate 2510, the output signal from the gate 2510 enables the gate 2513 to generate the XI signal. The XI signal is only maintained for two drum revolutions, however, because the flip-flops 2514 and 2515 are then toggled into the Q state by ETC1 pulses. It never takes more than two revolutions to store data into the auxilliary track, so this is sufficient time to allow the charge storing process to come to completion. During this period, the gate 3338 is disabled by the XI signal.

After the printout of the total figures of the day, it was noted above that the gate 3301 generated an RSU1 signal. This signal toggles a flip-flop 2710 shown in FIG. 27 and causes it to toggle the flip-flop 2712. The flip-flop 2712 then initiates the process of erasing the totals data for the previous day. The output signal from the flip-flop 2712 first enables the gate 2828 to generate a signal which passes through a gate 2826 and sets the core address register to location octal 000. Shortly thereafter the output signal from the flip-flop 2712 enables the gate 2714 to generate a signal which sets the bistable 2716 and which sets the core address register to octal location 114. This happens during the C01 timing interval. The output signal from the bistable 2716 partially enables the four gates 2720-2723. These gates control the totals erasure process so that only the total data is erased and so that the symbols and teleprinter control characters stored adjacent the totals data are not erased. The gates 2721 and 2723 generate and ADV 1+2 signal which advances the core address register. The gate 2722 generates an SCW3 signal that causes data to be read into the core memory from the core input data assembly register. The output signal from the bistable 2716 is called the RSTDRG signal, and is used to clear the core data input register so that the teleprinter character O can be loaded into all of the locations which are erased. This signal is fed to the gates in FIG. 23 which generate the RDREG (reset data register) signal and the SD5 + SD6 signal which places "1"s in bit locations 5 and 6 so that the data is recognized by the teleprinter as a number.

The data which is to be erased comprises four 8 character numbers stored in the core locations starting at octal addresses 114, 132, 150 and 166. Each of these locations is eight addresses in length, and there are six addresses between each of these locations which are not to be erased. The time when the erasure takes place determined by a gate 2724 which is enabled by timing signals C09, C18, and C27. During each of these character timing intervals, the gate 2723 is inhibited from generating the SCW3 signal which causes data to be written into the core, and the gate 2723 is allowed to pass six PHASE B timing pulses into the ADV 1+2 signal thus advancing the core address counter past the location which is not to be erased. Eight PHASE B timing pulses are applied to the gate 2723, but the gate is disabled during the T0 and T6 timing intervals by a gate 2725. During all other character counts between C01 and C35, a 0 is loaded into core during the T0 bit timing interval by the gate 2722, and the core address register is advanced during the T6 timing interval by the gate 2721. The gate 2720 is finally enabled during the T5 part of the timing interval C35 to generate an EAPC signal which clears the flip-flop 2712 and terminates the erasure procedure.

ARITHMETIC UNIT

FIGS. 19 through 24 disclose the arithmetic unit used in this system. The arithmetic unit performs arithmetic operations upon data stored within the core memory. It functions in much the same manner as the arithmetic unit of a conventional general purpose computer, although it has many special features which will be described below.

Figure 20:
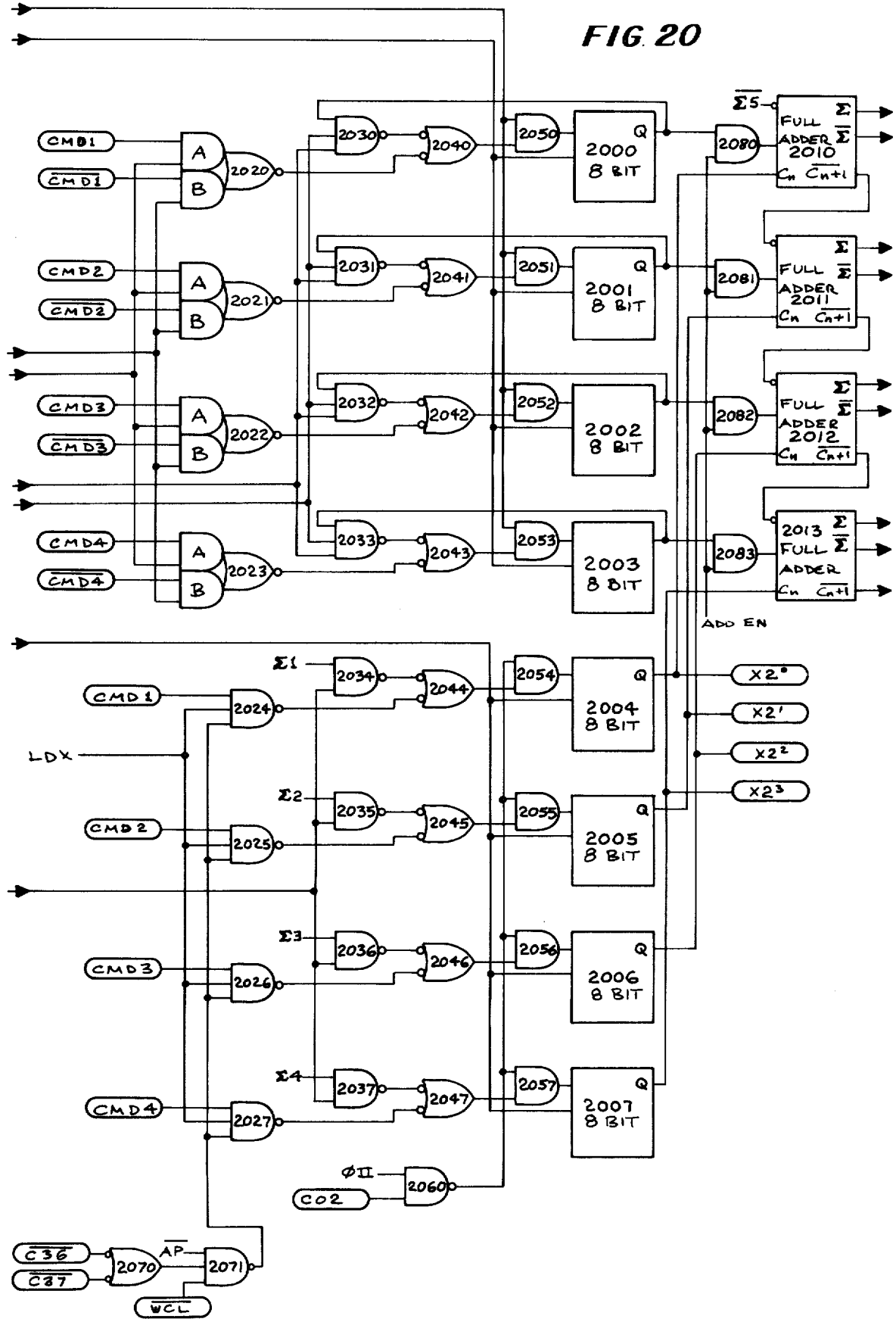
Figure 23:
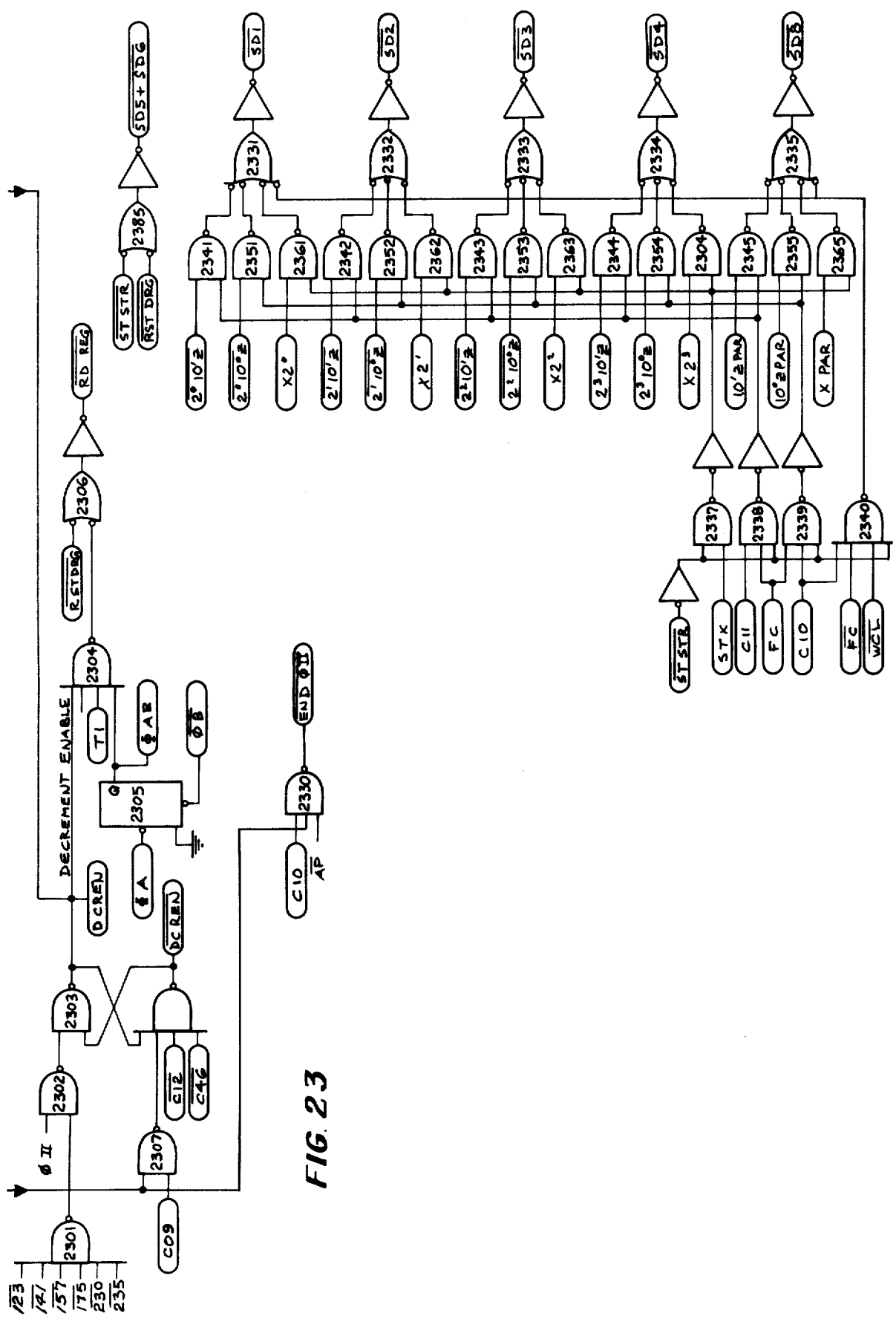
Figure 24:
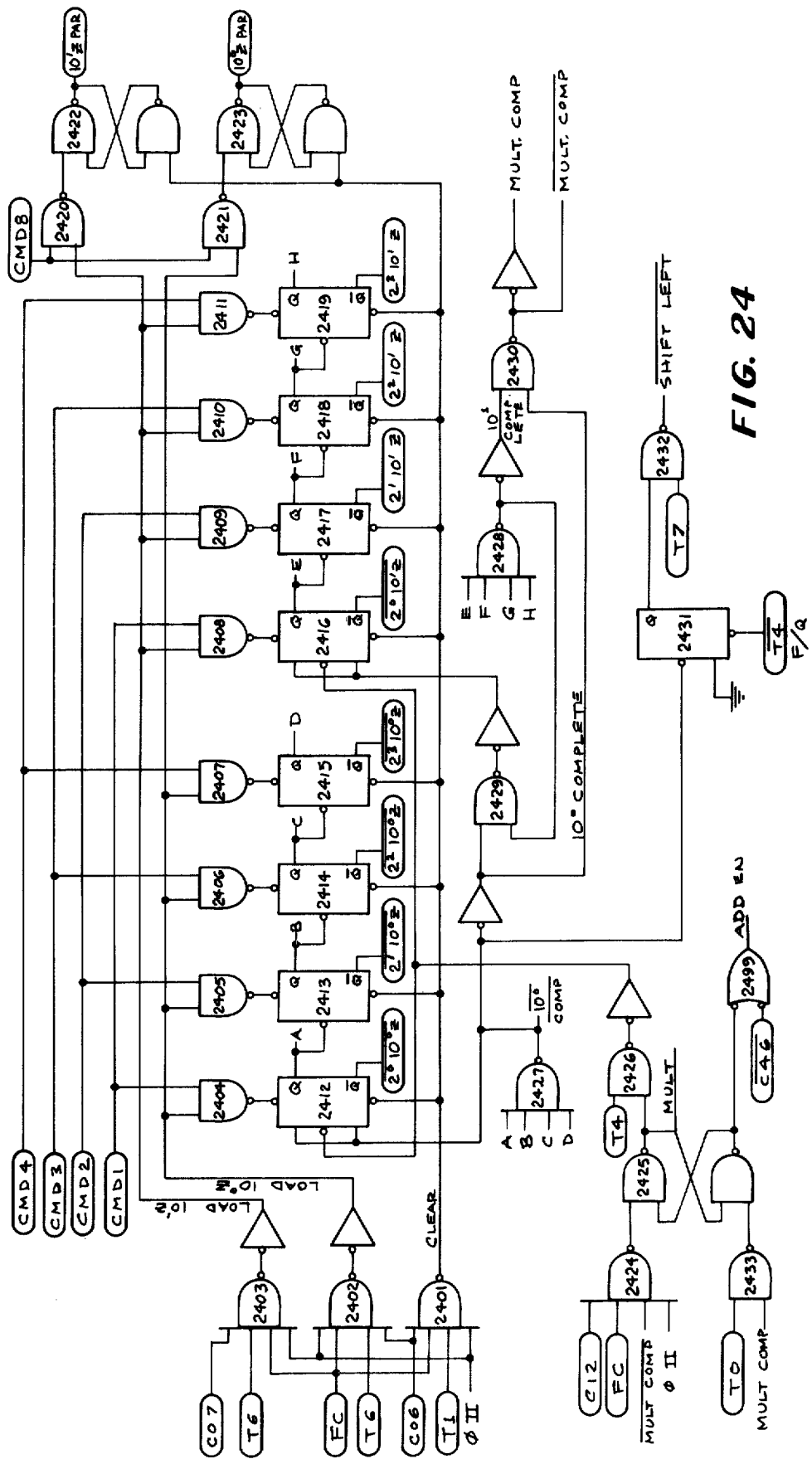

Basically, the arithmetic unit comprises an accumulator which occupies the lower half of FIG. 20; an input register, which occupies the upper portion of FIG. 20; a multiplier register, shown in FIG. 24; core address circuitry, shown in the right hand portion of FIG. 21; core input gating circuitry, shown at the right hand portion of FIG. 23; and control logic, shown mainly in FIGS. 19 and 22. Data from the core can be gated into both the input register and the multiplier register, and also into the accumulator. When data is gated into the input register, it may be inverted (placed in 1's complement form) for subtraction. Data can be gated back into core from either the accumulator or the multiplier register. Arithmetic is carried out by placing one number in the accumulator, and the other number in the input register, and then carrying out the arithmetic operation, leaving the result in the accumulator. Multiplication is carried out by placing one number in the input register and the other number in the multiplier register. Multiplication by successive addition is then carried out, and the result remains in the accumulator.

The arithmetic unit is used basically for two purposes in the present system. First of all, it is used to maintain a running total within the core memory of the total charges, total credits, and total payments on account handled by the system each day. Secondly, it is used to multiply the price accompanying a charge or credit item by the number of items which were included in the order.

Whenever a set of system input data includes an RC control character, the arithmetic unit is called into play right after the information is stored in the core memory. Various input signals, including an RC signal, enable a gate 2222 (shown in FIG. 22) to set a bistable 2223. The bistable 2223 partially enables a gate 2224. The remaining inputs to the gate 2224 are timing signals to insure that the gate 2224 is enabled at the start of a C00 bed information storage area character timing signal. When the next C00 signal arises, the gate 2224 sets the bistable 2201 and causes the generation of a PHASE II signal. This PHASE II signal is the master control signal for the arithmetic unit.

Before any arithmetic operations are carried out, the accumulator and the input register must be cleared. The accumulator is entirely cleared by a gate 2060, shown at the bottom of FIG. 20, which disables the four input gates 2054 through 2057 to four 8 bit accumulator shift registers 2004 through 2007. Simultaneously, the four shift registers are supplied with 8 shift pulses. The eight shift pulses are generated by a gate 1955. The C input to the gate 1955 allows eight PHASE B timing pulses to pass to the output of the gate 1955 during the character timing pulse C02. These PHASE B timing pulses pass through a gate 1950, which is enabled by the PHASE II signal. The input register is cleared in a similar manner by circuitry shown at the top of FIGS. 19 and 20. The gate 1907 disables the input gates 2050 through 2053 to four 8 bit input shift registers 2000 through 2003. Six shift pulses are supplied to these registers by a gate 1908. The same PHASE B pulses from the gate 1950 are applied to one input of the A section of the gate 1908, and the output signal from the gate 1907 is applied to the other input. The gate 1907 is disabled during the T6 and T7 parts of the C02 character signal, so that data may be read into the shift registers 2000 through 2003 during the latter portions of the character timing signal C02. Two bits of stray data remain in each shift register 2000–2003 but these bits are lost when the input data is shifted in.

After the input register and the accumulator have been cleared, multiplication is performed. First, the per unit price accompanying the input data is loaded into the input register. A gate 1901 sets a bistable 1903 at the beginning of the C02 character timing signal. The bistable 1903 generates an LDY (load Y) signal which passes through a gate 1906 and enables the D section of the gate 1908, allowing T6 bit timing signals to be applied to the input register as shift pulses. The T6 pulses pass through a gate 1951, which is enabled by the PHASE II signal. The LDY signal disables four gates 2030 through 2033 so that data cannot recirculate from the output of the shift registers 2000 through 2003 to the inputs of the shift registers. Data is clocked out of the core memory by T2 bit timing signals which pass through a gate 2207 (shown at the bottom right hand corner of FIG. 22) to form an SR R1 (read and restore) signal. The gate 2207 is enabled by the LDY signal generated by the bistable 1903. This signal passes through a gate 1906 and enables a gate 2210, which in turn generates a signal that passes through a gate 2211 and enables the gate 2207. Thus, during each T2 bit timing period, the core memory reads out an eight bit character and transmits the first four bits to the shift registers 2000 to 2003 in the form of signals CMD1 through CMD4. The gate 1908 generates a shift register pulse and gates these four bits into the first locations within the shift registers 2000 to 2003. The core memory output signal flows through the A sections of three gates 2020 to 2023, through the gates 2040 to 2043, through the shift register input gates 2050 to 2053, and into the four shift registers. The A sections of the gates 2020 to 2023 are enabled by the LDY signal generated by the bistable 1903. The bistable 1903 continues to generate the LDY signal until it is reset by a C06 timing signal. Thus, the LDY signal is allowed to exist for the duration of four character counts, long enough for four BCD numbers to be transferred out of core and into the shift registers 2000 through 2003. The LDY signal is terminated at the end of the character count C05, and the A sections of the gates 2020 to 2023 are disabled at this same time. The gates 2030 to 2033 are enabled, so that data in the input register can recirculate. Two more shift pulses are supplied to the input shift registers during character timing intervals C06 and C07 by the B and F sections of the gate 1908. During character timing intervals C06 and C07, the YL signal from the gate 1906 is maintained by C06 and C07 character timing signals so that the gate 2211 will read the multiplier out of the core memory. The YL signal also allows two more shift pulses to reach the shift registers 2000 to 2003, thus bringing the total number of pulses to eight, and thus shifting the least significant digit in the cost figure to the output of the shift registers 2000 to 2003.

If an FC control character accompanies the input data, this indicates a quantity order in which the unit price must be multiplied by a quantity number which is also part of the input data. This quantity number is stored in a special section of the core memory, and must be retrieved and used to multiply the price which is now stored in the input register. A gate 2184 is enabled by a C06 character pulse to advance the core memory address counter to location 402, where the least significant bit of this multiplier is stored. The multiplier is then gated into the multiplier register shown in FIG. 24 by the gates 2401 and 2403. Gate 2401 generates a clear pulse during a T1 bit timing interval to clear the eight flip-flops 2412 through 2419, and the two bistables 2422 and 2423. The gate 2402 then loads the core memory data (multiplier units digit) into the four flip-flops 2412 through 2415 during the T6 portion of character count C06. Next the gate 2403 loads the core memory data (multiplier tens digit) into the four flip-flops 2416 through 2419 during the T6 portion of the character count C07. Simultaneously, the gates 2402 and 2403 gate the parity bits which accompany this data through the two gates 2420 and 2421 and into the two bistables 2422 and 2423. In this manner, the multiplier is loaded into the multiplier register. This number is in 1's complements form within the flip-flops 2412 through 2419 and therefore appears at the $\bar{Q}$ outputs of these flip-flops, rather than at the Q outputs.

The input charge information is transferred into the core memory on a separate input card from the quantity number. In order to prepare the data within the core memory for transmittal to the charge information storage area of the magnetic drum, it is necessary to place this quantity within the center of the location where the other charge information is stored. This is done by gating the two numbers appearing at the $\bar{Q}$ outputs of the two groups of flip-flops 2412 through 2415 and 2416 through 2419 back into the proper place within the core memory. This is done by the circuitry shown in the right-hand portion of FIG. 23. A C10 character pulse and the FC (multiplier) signal first enable the gate 2339 which gates the output signals from the flip-flops 2412 through 2415 out through the gates 2351 through 2355 and the gates 2331 through 2335, and into the data input register of the core memory in the form of the signals SD1 through SD8. Simultaneously, the gates 2335 and 2355 gate the parity bit out of the bistable 2423 and causes it to become the ST8 signal. "1"s are added to a fifth and sixth bit locations in the core memory input register by a gate 2385. The gates 2385 and 2339 are enabled by an ST STR signal generated by a gate 2205, located at the right-hand edge of FIG. 22. The gate 2205 is enabled during the T1 bit timing intervals by a STZ signal which comes from a bistable 2203 through a gate 2204. The bistable 2203 is set by a gate 2202 during the C08 timing interval. The gate 2202 is disabled by a WCL signal during the input of data from the cashier's terminal, since no multiplication is ever carried out upon such data.

In a similar manner, the number stored in the flip-flops 2416 through 2419 and the parity bit in the bistable 2422 are also gated back into the core memory through the gates 2341 through 2345, by a gate 2338 that is enabled during the C11 timing interval. Once data is placed in the core memory data register, it is gated into storage by an SC W1 (core memory clear and write) signal generated by a gate 2206 during the T2 timing interval. The gate 2206 is enabled by the STZ signal generated by the bistable 2203. The core input data register is periodically cleared by an RDREG signal generated by a gate 2306 during a portion of the T1 timing interval. The particular portion of the timing interval during which the signal is generated is determined by a flip-flop 2305, which generates special PHASE AB signal.

If no F control character accompanies the input data, then there is no multiplication to be carried out. No data is read from core into the multiplier register in this case, because the three gates 2401 through 2403 are disabled by the absence of an FC signal. "1" quantity number is placed in the quantity slot of the data which is to be fed to the charge information storage area by the gate 2340. This is done automatically during the C10 interval whenever the FC signal is absent except during the processing of data from the cashier, as indicated by a control W character and a WCL signal. The gate 2340 is disabled whenever a WCL signal is present. The quantity multiplier number is used during tally searches as an indication of how many items were involved in each transaction. No items are ever involved in transactions carried out at the cashier's office, so a multiplier number is not needed.

During the period when the multiplier register is loaded with data, it is necessary to maintain the signal at the output of the gate 1906 so that the SR R1 signal generated by the gate 2207 to read data out of the core memory is maintained. This is done by the C06 and C07 timing pulses mentioned above.

The four flip-flops 2412 through 2415 and the four flip-flops 2416 through 2419 are interconnected among themselves to form two counter circuits. It was noted above that the BCD numbers stored within these two sets of flip-flops are in complement form. In accordance with the theory of binary arithmetic, the number of counts which it will take to advance each of these sets of flip-flops until "1"s appear at all the flip-flop Q output terminals is equal to the numbers stored within each set of flip-flops. This, if the number 2 is stored in the set of flip-flops 2412 through 2415, it will take exactly two counts applied at the input of a flip-flop 2412 to produce all "1"s at the Q outputs. In the discussion to follow, the two sets of flip-flops will frequently be referred to as flip-flop counters.

When "1"s are present at the Q outputs of the four flip-flops 2412 through 2415, a gate 2427 generates a $10^0$ COMP (units digit multiplication complete) signal. Similarly, when "1"s appear at the Q outputs of the four flip-flops 2416 through 2419, a gate 2428 generates a $10^1$ COMPLETE (tens digit multiplication complete) signal.

Multiplication is initiated by a MULT signal generated by a bistable 2425. The bistable 2425 is set up by gate 2424 in response to the FC signal, the C12 timing signal, the PHASE II signal, and an inverted MULT COMP (multiplication complete) signal. This latter signal is formed by combining the $10^0$ COMPLETE signal with the $10^1$ COMPLETE signal in a gate 2430, and indicates that all of the flip-flops 2412 through 2419 have "1"s appearing at their Q outputs. Generally, assuming that a number has been gated into the flip-flops 2412 through 2419, this will not be the case initially. Thus, the MULT signal is usually generated at the start of a C12 timing signal. This signal enables the E section of the input registers shift pulse gate 1908, and also the A section of the accumulator shift pulse gate 1955. These two gates are both connected to the PHASE B timing pulse signals generated by the gate 1950, and allow PHASE B pulses to shift data out of the shift registers 2000 through 2007. So long as the MULT signal remains positive, data continuously flows out of the four shift registers 2000 to 2003 and out of the four shift registers 2004 to 2007. The data flowing out of the shift registers 2000 to 2003 recirculates through the gates 2030 to 2033 and back into the shift registers 2000 to 2003 once again, and is not lost. Data from both sets of shift registers flows into the full adder circuits 2010 through 2013. In a manner that will be described more fully below, addition is performed, and the sum appears at the output of full adders 2010 and 2101 to 2103. This sum signal is fed back through the gates 2034 to 2037 into the accumulator shift registers 2004 through 2007. Each time eight PHASE B pulses are generated by the gates 1908 and 1955, the data contained within the input register is added to the data contained within the accumulator, and the result of this addition is stored in the accumulator.

The number of additions which occur is determined by the multiplication logic circuitry shown in FIG. 24. The MULT signal enables a gate 2426 to pass T4 timing signals to the two flip-flop counters 2412-2415 and 2416-2419. The flip-flop 2416 is initially disabled by a signal generated by a gate 2429 in response to the absence of any $10^0$ COMP signal being generated by the gate 2427. The input to the flip-flop 2412 is enabled by the absence of this same signal. Thus initially the T4 counting pulses generated by the gate 2426 are applied only to the input of the flip-flop counter 2412-2415. The counter 2412-2415 advances one count for each eight PHASE B pulses applied to the input register and accumulator, or once for each time the number in the input register is added into the accumulator. In this manner, the number stored in the input register is added into the accumulator a number of times equal to the units multiplier digit. When this process is completed, "1"s appear at the Q outputs of all the flip-flops 2412 through 2415, and the $10^0$ COMPLETE signal is generated by the gate 2427. This signal disables the flip-flop 2412, thereby terminating the unit's digit counting procedure, and enables a gate 2429 so that the flip-flop counter circuit 2416-2419 can count. This signal also toggles a flip-flop 2431 into the Q state, enabling a gate 2432 to pass a T7 timing pulse and thus generate a SHIFT LEFT pulse. This SHIFT LEFT pulse is applied to the E input of gate 1908, disabling the E input for the duration of one PHASE B counting pulse. Only seven shift pulses are applied to the four shift registers 2000 through 2003, and the data within the accumulator is effectively multiplied by ten (this amounts to inserting a zero at the output end of the shift registers 2000 through 2003, in front of the price number). In this manner, the arithmetic unit is prepared for the 10s digit part of the multiplication procedure.

The number in the input register, multiplied by 10 in the above manner, is now added to the number in the accumulator a number of times equal to the 10s digit of the multiplier. This process is carried out in exactly the manner described above, with the T4 pulse advancing the flip-flop counter 2416–2419 each time the number in the input register is added to the contents of the accumulator. When the process is complete, "1"s appear at the Q outputs of the four flip-flops 2416 through 2419 and cause the gate 2428 to generate a $10^1$ COMPLETE signal. This signal, and the $10^0$ COMPLETE signal, enable the gate 2430 to generate the MULT. COMP (multiplication complete) signal. This signal enables the gate 2433 to clear the bistable 2425 at the start of the T0 bit during the next character count, thus terminating the MULT signal. The MULT signal then no longer enables the gates 1908 and 1955, and the multiplication procedure stops. The resultant product is stored in the accumulator, in the shift registers 2004 through 2007.

If the unit's digit in the multiplication was 0, the usual SHIFT LEFT signal is not generated. It is necessary, therefore, to generate a substitute for the SHIFT LEFT pulse before multiplication is attempted. This is done by inhibiting the F section of the gate 1908 during the character count timing interval C07 so that the date in the input shift register is left one bit position away from the register output. If the unit's digit of the multiplier is zero, a 10° COMP signal is present during C07. The 10° COMP signal is therefore used to inhibit the F section of the gate 1908.

At most, the multiplication process takes no more than twenty character counts. By the time of the C30 character timing interval the multiplication process is completed. If a multiplication was performed, the result of that multiplication is stored within the accumulator. If not, the accumulator is empty. In this latter case it is now necessary to once again retrieve the price data from core, this time storing it in the accumulator. This is done by a bistable 1954 during the character counts C30 through C37. A gate 1952 causes the bistable 1954 to generate an LDX signal during the C30 character timing interval whenever an FC (multiply) signal is not present. It will be remembered that the FC signal is only present when multiplication is to be performed. This LDX signal loads the accumulator with data in much the same manner as the LDY signal generated by the bistable 1903 loaded the input register with data. Data flows from the core memory, through the gates 2024 to 2027, 2044 to 2047, and 2054 to 2057 and into the four shift registers 2004 to 2007. The gates 2024 to 2027 are partially enabled by the LDX signal generated by the bistable 1954, and are partially enabled by a signal generated by a gate 2071. Timing signals C36 and C37 are combined by a gate 2070 and cause the gate 2071 to disable the gates 2024 through 2027 during time intervals C36 and C37, so that only six characters are actually read out of the core and into the shift registers 2004 through 2007. Shift pulses are still supplied to the four shift registers, however, so the data which does reach the shift registers is shifted to the output end of the shift registers in proper position for further manipulation. When data from the cashier's input is being processed, a WCL signal prevents this erasure of the last two pieces of information, so that eight digits of price data may be read in from the cashier. Similarly, when the days totals are calculated in a manner to be described below, an AP signal disables the gate 2071 and allows eight digits of data to flow into the shift registers 2004 through 2007. The LDX signal enables the D section of the gate 1955 and allows eight T6 timing pulses to clock the data into the accumulator.

As noted above, it is not necessary to load the accumulator during the character counts C30 through C37 after a multiplication has been carried out. However, the results of the multiplication must be transferred back into the core memory in the location where the per unit was originally stored, so that the extended price can accompany the input data into the charge information storage area. This readout of data from the accumulator is initiated by an STX1 (store X) signal generated by a bistable 2219 located just below the center of FIG. 22. An input gate 2218 sets the bistable 2219 at the beginning of the C30 character timing interval. The FC (multiplication control character) signal must be present, or the gate 2218 remains disabled and the bistable 2219 is not set up. The gate 2218 is also disabled by a SUB EN (subtraction enable) signal generated by a bistable 2213 when subtraction is to be performed rather than addition. The STX1 signal passes through a gate 2220 and becomes the STX signal. The STX signal enables a gate 2337 which in turn enables gates 2361 to 2365 and allows them to transfer data from the accumulator into the core memory input data register. This data is gated into the core input data register by the ST STR pulse signal generated by the gate 2205. The gate 2205 is enabled by the STX1 signal, which normally passes through a gate 2221 and gates 2204 to the gate 2205. The information is then transferred into core by an SCW1 pulse generated by the gate 2206. This gate is also enabled by the STX1 signal. At the start of the next T1 timing interval, the core input data register is cleared by an RD REG signal generated by the gate 2304 and passed through the gate 2306.

Six characters are read into the core memory, including a two character cents number and a four character dollars number. The gate 2221 is then disabled by C36 and C37 timing signal to prevent seventh and eighth bits of data from being placed into the storage area and erasing the multiplier number. The STX1 signal is maintained during the C36 and C37 time intervals so that the accumulator data is shifted back to its original position.

During the STX1 data readout, data is gated through the accumulator by T6 timing pulses which pass through the B section of the gate 1955. This B section is enabled by the STX1 signal. In the timing interval C30 to C38, eight T6 pulses pass from the gate 1955 and route the data out of the shift registers 2004 through 2007, through the arithmetic logic, and back into the shift registers 2004 through 2007. No addition is performed during this operation, because an ADDEN (addition enable) signal is not present, and therfore the input gates 2080 through 2083 to the full adders 2010 through 2013 are disabled and prevent the data in the input register from being presented to the full adders. This ADD EN signal is generated by a gate 2499 located in the lower left hand portion of FIG. 24. The gate 2499 receives as input signals a multiplier signal generated by the bistable 2425, and a C46 character timing pulse. Thus, the input gates to the adder are only enabled during the multiplication process, and during timing interval C46 when addition and subtraction are performed.

The arithmetic unit now withdraws the current total day's charges number from the core memory, updates this number by adding into it the extended price located in the accumulator, and returns the charge number to core. The charge number is read out of the core storage during character counts C38 through C45. Character count C38 enables the gate 1902 to set a bistable 1903 and once again causes a generation of the LDY (load input register) signal. This signal causes the first four bits in the eight characters which comprise the charge number to be read out of the core memory and into the input register. This process is carried out in a manner identical to the manner in which the input register was loaded during the timing interval C02 to C05.

The addition of the two numbers is carried out during the character timing interval C46. The C46 timing signal enables the C section of the gate 1908 and the E section of the gate 1955 to pass eight PHASE a shift pulses to both the input register and the accumulator. The input gates to the full adder circuits 2010 to 2013 are enabled during this timing interval by the ADD EN signal generated by the gate 2499. Thus, during this character timing interval, the characters within the register and the accumulator are clocked out one at a time, added together, and the sum is stored in the accumulator.

The charge number is fed back into the core memory during the C01 through C08 timing intervals which next occur. A gate 2214 sets the bistable 2215 and causes the generation of a 2ND 1/2 signal during C47. This signal enables the gate 2216 to allow a C01 time signal to set a bistable 2217 at the beginning of the next C01 timing signal. The bistable 2217 generates a STX2 (store data X) signal which initiates a storage of accumulator data in the core memory. The 2ND 1/2 signal also enables the gate 2298 to allow a C02 timing pulse to reset the bistable 2201 at the beginning of the T2 character count, thus terminating the PHASE II signal at the start of the second character count and preventing more data from being fed into the arithmetic unit.

The STX2 signal causes accumulator data to be shifted into core in the same manner that the STX1 signal caused accumulator data to be shifted into core. The STX2 signal is supplied directly to the gate 2204, and does not pass through a gate analagous to the gate 2221, so all eight characters in the accumulator are stored during this procedure. A C09 character timing signal resets the bistable 2217. The 2ND 1/2 signal is terminated at the beginning of the 38th character count by a C38 character timing signal.

The above description was concerned with the way the arithmetic unit handles a typical charge data set accompanied by an R (charge) control character, and possible accompanied by an F (multiply) control character. If the input data set was accompanied by a T (credit) control character, the procedure is exactly the same except that instead of the extended price being added to the total of the days charges, the extended price is added to the total of the days credits. A T control character indicates a credit item, rather than a debit time. The only difference in the way the system handles an item including a T control character is in the address to which the core address register is set before data is read into or out of the core memory.

Address register setting circuitry is shown at the right hand portion of FIG. 21. This circuitry comprises a simple array of gates which generate address register signals 123, 141, . . . , and 402 at appropriate times, so that the address in the core address register is set to the location of the first item which is to be printed out.

During most data readouts, the core address register is then advanced by a DP1 signal generated by a gate 2208 during PHASE B of the timing interval T7. This gate, and the other four adjacent gates 2205 through 2207, are enabled by a DCREN (decrement enable) signal which will be explained below. The DP1 signal is not generated during the eighth character count of the STX2 procedure. It is suppressed by a gate 2209 which receives a 2ND 1/2 input signal and a C08 timing signal, thus leaving the address register set to the location of the most significant character of the data just stored when the arithmetic process is completed.

A typical section of the address setting register comprises the three gates 2150, 2151 and 2152. These three gates cause the core address register to be set to the location of the least significant bit in the days credit total, which is stored in octal location 141 within the core memory. The output signal is generated during the character count C38 whenever a T control character indicates a credit item. The TC (T control) signal and a C38 timing signal enable the gate 2150. The output signal from this gate flows through the gate 2151 and enables the gate 2152. The gate 2153 then generates a T0 PHASE B timing pulse which passes through the gate 2152 and becomes the 141 pulse. In this manner, the core address register is set to octal location 141 at the very start of the 38th character count, just before core data is read into the input register in the manner described above. The DP1 signal generated by the gate 2208 then advances the core address register by one count after each data item is read into the input data register. The signal generated by the gates 2152 and by the gate 2208 thus cause the core address register to always be set at the proper location at the proper time. The other gating circuits shown in FIG. 21 perform similar tasks at other times and in response to other control signals. For example, when the TC signal is not present, indicating that there is no T control character in the input data, the gate 2160 generates a signal during the 38th character count. This signal passes through the gate 2161 and enables the gate 2162 to generate an octal 123 core address location signal. This signal sets the core address counter to the octal location 123, where the least significant digit in the charge total number is stored. Thus, the charge number is read into the input register during character counts C38 through C45, rather than the credit total number, when the T control character is not present.

When data is transferred between the core memory and the arithmetic unit, it is always transmitted in inverse order. The least significant digit is transmitted first, then the next more significant digit and then the next more significant, and so on. Ordinarily, data is transmitted to and from the core in the opposite order from this. It is therefore necessary to reverse the direction in which the core location counter counts whenever arithmetic data is being transferred between the core and the arithmetic unit. This is done by a bistable 2303 which generates a DCREN signal. The bistable 2303 is enabled by a gate 2301 in response to any one of the address register setting signals 123, 141, . . . , and 235 being present. Each time the address register is set to an address by the address setting circuitry in FIG. 21, the DCREN signal is generated. In addition to causing the core address counter to count backwards, the DCREN signal also enables the gates 2205 through 2208 and allows these control signals to flow to the core memory. This signal also enables the gate 2304 to generate the pulses which reset the core input data register at the very beginning of each T1 bit timing interval. The DCREN signal is terminated at the start of character counts C12 and character count C46, and also at the start of character count C09 when the 2ND 1/2 signal is present. This latter termination is initiated by a gate 2307. The DCREN signal is only present when data is being transferred between the arithmetic unit and the core memory.

Data received from the cashier's input terminal is handled somewhat differently than the usual charge data items. Such data is accompanied by a W control character, and sometimes by an X control character. The W control character indicates payment on account data from the cashier's office. The X control charactor indicates a correction, or credit, to payments on account. These two control characters cause the system to generate an XCL and a WCL signal, as explained in the concurrently filed application. If no XCL signal is present, the input data is handled in much the same manner as charge information. No multiplication is carried out and the WCL signal disables the gate 2202 and prevents the generation of an STZ signal, so the multiplier is not stored. The WCL signal causes the core address location circuitry shown in the right hand portion of FIG. 21 to load the payment on account totals number into the accumulator during character counts C31 through C38, and to load the amount supplied by the cashier into the input register during character count C38 through C45. Addition is then performed in the usual manner, and the updated payment on account totals number is transferred back into core during character counts C01 through C09. The WCL signal disables the gate 2071, and allows the last two bits of the payment totals number to enter the accumulator.

If the input data included the XCL control character, the operation proceeds in almost the same manner, except that a subtraction is carried out rather than an addition. Thus, the amount fed in by the cashier is subtracted from the day's total payments received on account. The XCL signal enables the gate 2212 to pass a C01 timing pulse which sets a bistable 2213 and generates a SUBEN (subtraction enable) signal. This signal is applied to a gate 2130 located in the lower left hand portion of FIG. 21, to alter the arithmetic logic, and is also applied to the gates 1902 and 1904. The signal disables the gate 1902 and enables the gate 1904, thus causing the bistable 1905 to be set up by the 38th character timing pulse rather than the bistable 1903. The bistable 1905 causes inverted core memory data to be read into the input register through the B input of the gates 2020 to 2023, thus setting up the register for the performance of "1"s complement subtraction. In all other respects, the bistable 1905 functions in exactly the same manner as the bistable 1903. The WCX control character thus allows corrections to be made in the payments on account total number.

The arithmetic unit performs one other function within the system. It was noted above that at the beginning of an APC (all patient's charges) printout, the total charges, credits, and the toal payments on accounts are printed out. In addition, a net figure is printed out. This is the difference between the total day's charges and the total day's credits. This figure is computed by the arithmetic unit. An INH APC (inhibit APC) signal toggles the flip-flop 2250 and allows a gate 2251 to set a bistable 2252 during delay line bit timing interval IT3 when a PHASE 1 signal is not present. The PHASE 1 signal is generated by the tally search control logic. The IT3 (bit 3 delay line input timing) signal is generally not used in the parts of the system disclosed in this application, and is explained in more detail in the concurrently filed application.

When the bistable 2252 is set, it generates a SET APC CYCLE signal which sets a bistable 2253 and causes an AP signal to be generated. The SET APC CYCLE signal also sets the bistable 2223, and initiates the generation of the PHASE II signal in the manner described above. The bistable 2213 is also set, generating a SUBEN (subtraction enable) signal which adapts the arithmetic unit to perform subtraction in the manner described above. The arithmetic unit then performs subtraction in the usual manner under the control of the AP signal. This signal causes the charge total number to read into the accumulator during character timing pulses C30 through C37, and causes the credit total number to be read into the input register in complement form during character timing pulses C38 through C45. Subtraction is then performed, and the result of the subtraction is stored in the net total core storage area that ends with octal address 157 during character counts C01 through C08. The AP signal is applied to the core address setting logic shown in the right hand portion of FIG. 21 to cause the above data to be manipulated in the manner specified. When this task is finished, the address register is left containing the address of the most significant digit in the net total number.

The input data, as received from the input units and as stored in core, includes a decimal point which separates the dollar portions of the price from the cents portion. It is necessary to prevent this decimal point from being read into the arithmetic unit, so that the decimal point is not interpreted as a number and added to the other data. This is done by a gate 2154 shown in the lower right hand portion of FIG. 21 which generates a DP2 signal. This DP2 signal causes the core addresses register to advance an extra count whenever it is necessary to skip a location containing a decimal point. Gates 2155 through 2157 combine timing signals and control signals that determine exactly when a decimal point will appear. The resulting composite signal produced by the gate 2155 is used to enable the gate 2154 at the appropriate times.

Addition and subtraction are performed by the four full adders 2010 through 2013. These adders receive as input data the four bit BCD number presented at the output terminals of the shift registers 2000 through 2003, and the four bits BCD number presented at the output terminals of the shift registers 2004 through 2007. The resulting sum signal which appears at the outputs of the full adders 2010 through 2013 is the binary sum of the two BCD numbers. Whenever the sum is greater than nine, it is necessary to translate this sum into BCD form by adding the binary number six (0110) to the sum. The presence of a sum greater than nine is detected by a gate 2108, which applies the 1 portions of the number 0110 to the inputs of two full adders 2101 and 2102. The three most significant bits of the output sum presented by the adders 2010 through 2013 are then passed through the adders 2101 through 2103 so that the result is added to 0110. The sum in BCD form thus appears at the output of the adders 2010, 2101, 2102, and 2103. This sum is fed back through the gates 2034 through 2037 and is fed into the four 8 bit shift registers 2004 through 2007.

Three gates 2105 through 2107 determine whether the binary number displayed by the full adders 2010 through 2013 is greater than nine. The gate 2107 is enabled by the overflow carry output from the input adder 2013 whenever the sum is greater than sixteen. The gate 2106 is enabled by the outputs of the adders 2013 and 2011 whenever the sum is 10 or 11, and the gate 2105 is enabled by the output of the adders 2012 and 2013 whenever the sum is 12 or 13. A sum of 14 or 15 will enable both of the gates 2105 and 2106. The signals generated by the three gates 2105 to 2107 are combined by a gate 2108 to form the signal which adds a binary number six to the sum. This same signal also serves as an overflow carry signal. It is passed through a gate 2109 and is stored in a flip-flop 2104. The overflow bit is fed back into the full adder 2010 when the next two characters are summed. The flip-flop 2104 is initially cleared by a gate 2135 in response to a signal formed by ANDing together a T0 timing pulse with a PHASE AB pulse generated by the flip-flop 2305.

When subtraction is to be performed, the "1"s complement of the number to be subtracted is stored in the input data register. A SUBEN signal enables the gate 2130 and causes it to disable the three addition logic gates 2105 through 2107, and the carry bit flip-flop setting gate 2135, and to enable the two gates 2131 and 2133. These latter two gates are used in the subtraction process. In accordance with the theory with the ones complement arithmetic, the difference between two numbers is formed by adding the first number and to the ones complement of the second number, and performing an end around carry with the carry bit. This task is done by the full adders 2010 through 2013. A carry input is initially applied to the full adder 2010 by the flip-flop 2104 to serve as the end around carry. The flip-flop 2104 is initally placed in the "1" state by a gate 2134 that is enabled during character count C45 by an LDY COMP signal generated by the bistable 1905. The difference between the two numbers then appears in binary form at the outputs of the four adders 2010 through 2013. If this difference is less than zero with no overflow carry, it is necessary to correct the difference to place it in BCD form by adding ten (1010) to the difference, and it is also necessary to suppress the carry by preventing the flip-flop 2104 from adding a 1 to the next character sum. The addition of 1010 is initiated by the gate 2131, which feeds the "1"s portion of the binary number ten into the two adders 2101 and 2103 whenever there is no overflow carry from the full adder 2013. The addition of ten to the full adders 2101 to 2103 causes an overflow carry to occur in the adder 2103. This overflow carry is passed through the gates 2133 and 2109 to the flip-flop 2104. Such a carry toggles the flip-flop into the "0" state and does not supply a carry for the next summing operation. The gate 2132 disables the gate 2131 when the full adders 2010 through 2013 contains the number zero, and thereby prevents the addition of ten to the number zero.

The flip-flop 2104 is toggled by the XSP shift register pulses generated by the gate 1955 along with the accumulator shift registers.

We claim:

1. An automated inventory control and accounting system for processing a plurality of data messages containing charge data and inventory data and for automatically compiling charge records organized by a plurality of charge codes from said charge data in the form of monetary charges for items or services to be charged to various ones of said plurality of charge codes and for automatically compiling inventory records organized by a plurality of item codes from said inventory data reflecting the inventory of said items comprising means for receiving said data messages, said data messages receiving means comprising a plurality of remote stations, each of at least some of said remote stations including means for manually entering said data messages into said remote stations, said manually entering means including means for entering a specific charge code of said plurality of charge codes into said remote station, means for entering a specific item code of said plurality of item codes corresponding to one of said items or one of said services into said remote station and means for entering a multiplier corresponding to the quantity of said one item or service into said remote station, each of at least some of said data messages including said specific charge code, said specific item code and said multiplier, a first information storage location, means for transmitting said data messages from said remote stations to said first information storage location for storage therein, a second information storage location, means for monitoring said data messages stored in said first information storage location and for automatically extracting said charge codes, item codes and multipliers from said data messages and for transmitting said charge codes, item codes and multipliers to said second information storage location for storage therein, means for retrieving item codes and multipliers associated with a predetermined charge code of said plurality of charge codes from said second information storage location and for automatically compiling and outputting a charge record corresponding to said predetermined charge code and means for retrieving item codes and multipliers associated with a predetermined item code of said plurality of item codes from said second information storage location and for automatically compiling and outputting an inventory record corresponding to said predetermined item code.

2. An automated inventory control and accounting system as defined in claim 1 wherein said charge code entering means, said item code entering means and said multiplier entering means of said manually entering means includes a plurality of prepared machine-readable records at said some of said remote stations.

3. An automated inventory control and accounting system as defined in claim 1 wherein said charge code entering means is a first plurality of prepared machine-readable records and said item code entering means and said multiplier entering means are a second plurality of prepared machine-readable records.

4. A machine implemented data handling system for processing a plurality of data messages containing inventory data and for automatically compiling inventory records organized by a plurality of item codes from said inventory data reflecting the inventory of inventory items comprising.

means for receiving said data messages, said data messages receiving means comprising a plurality of remote stations, each of at least some of said remote stations including means for manually entering said data messages into said remote stations, said manually entering means including a plurality of machine-readable records at said some of said remote stations, each machine-readable record of said plurality of machine-readable records including an item code in machine-readable form corresponding to a specific inventory item and means for entering a multiplier corresponding to the quantity of said inventory item into said remote station; each of at least some of said data messages including said item code and said multiplier, a first information storage location, means for transmitting said data messages from said remote stations to said first information storage location for storage therein, a second information storage location, means for extracting said item codes and said multipliers from the data messages stored in said first information storage location and for transmitting the extracted item codes and multipliers to said second information storage location for storage therein and means for retrieving item codes and multipliers associated with a predetermined item code of said plurality of item codes from said second information storage location and for automatically compiling and outputting an inventory record corresponding to said predetermined item code.

5. A machine implemented data handling system for processing a plurality of data messages containing charge data and inventory data and for automatically compiling charge records organized by a plurality of charge codes from said charge data in the form of monetary charges for charge items to be charged to various ones of said plurality of charge codes and for automatically compiling inventory records organized by a plurality of item codes from said inventory data reflecting the inventory of said charge items comprising means for receiving said data messages, said data messages receiving means comprising a plurality of remote stations, each of at least some of said remote stations including means for manually entering said data messages into said remote stations, said manually entering means including means for entering a specific charge code of said plurality of charge codes into said remote station, means for entering a specific item code of a plurality of item codes corresponding to a specific charge item of said charge items into said remote station and means for entering a multiplier corresponding to the quantity of said specific charge item into said remote station, each of at least some of said data messages including said specific charge code, said specific item code and said multiplier, a first information storage location, means for transmitting said data messages from said remote stations to said first information storage location for storage therein, a second information storage means, means for extracting said charge codes, said item codes and said multipliers from said data messages stored in said first information storage location and for transmitting the extracted charge codes, item codes and mulipliers to said second information storage means for storage therein means for retrieving said item codes and multipliers associated with a predetermined charge code of said plurality of charge codes from said second information storage means and for automatically compiling and outputting a charge record corresponding to said predetermined charge code and means for retrieving said items codes and multipliers associated with a predetermined item code of said plurality of item codes from said second information storage means and for automatically compiling and outputting an inventory record corresponding to said predetermined item code.

6. A machine implemented data handling system as defined in claim 5 wherein said data messages contain institutional bed data in the form of status information of the institutional beds organized by a plurality of bed designation codes, said machine implemented data handling system automatically maintains a record of the institutional bed allocation, said manual entering means further comprises means for entering a specific bed designation code of said plurality of bed designation codes into said remote station and means for entering a specific status code of a plurality of status codes corresponding to the specific status of one of said beds into said remote station, each of at least some of said data messages including said specific bed designation code and said specific status code, and said second information storage means further comprises a plurality of bed information storage locations, each of said plurality of bed information storage locations being associated with a specific one of said plurality of bed designation codes, said machine implemented data handling system further comprising means for extracting said bed designation codes and said status codes from said data messages stored in said first information storage location and for transmitting the specific status codes corresponding to specific bed designation codes to the respective bed information storage locations of said plurality of bed information storage locations associated with said specific bed designation codes and means for retrieving and for automatically outputting a record of all of said bed designation codes corresponding to a specific status code of said plurality of status codes to thereby provide a record of the status of said institutional beds.

7. A machine implemented data handling system as defined in claim 5 wherein said data messages contain institutional bed data organized by a plurality of bed designation codes for the institutional beds and by a plurality of status codes corresponding to the identity of the occupants of said institutional beds, said machine implemented data handling system automatically maintains a record of the institutional bed occupancy status, said manual entering means further comprises means for entering a specific bed designation code of said plurality of bed designation codes into said remote station and means for entering a specific status code of said plurality of status codes into said station, each of at least some of said data messages including said specific bed designation code and said specific status code, and said second information storage means further comprising a plurality of bed information storage locations, said machine implemented data handling system further comprising means for assigning a specific bed designation code to each of said plurality of bed information storage locations, means for extracting said bed designation codes and said status codes from said data messages stored in said first information storage means and for transmitting the extracted status codes corresponding to specific extracted bed designation codes to the specific ones of said plurality of bed information storage locations respectively assigned to said specific extracted bed designation codes for storage therein and means for automatically retrieving and for automatically outputting specific bed designation codes associated with a specific status code to thereby enable the rapid identification and location of a particular occupant of an institutional bed by knowledge of the identity of said particular occupant.

8. A machine implemented data handling system as defined in claim 5 wherein said data messages contain institutional bed identification data in the form of a plurality of bed designation codes institutional bed occupant status data in the form of a plurality of occupant codes and institutional bed status data in the form of a plurality of status codes, said machine implemented data handling system automatically maintains a record of institutional bed allocation, occupancy and status, said manual entering means further comprises means for entering a specific bed designation code of said plurality of bed designation codes into said remote station, means for entering a specific occupant code of said plurality of occupant codes into said remote station and means for entering a specific status code of said plurality of status codes into said remote stations each of at least some of said data messages including at least one of said specific bed designation code and said specific occupant code and said specific status code, and said second information storage means further comprises a plurality of bed information storage locations, said machine implemented data handling system further comprising, means for assigning a specific one of said plurality of bed designation codes to each one of said plurality of bed information storage locations, means for extracting said bed designation codes, said occupant codes and said status codes from said data messages stored in said first information storage location and for transmitting said bed designation codes, said occupant codes and said status codes to said plurality of bed information storage locations, each of said plurality of bed information storage locations receiving specific occupant and status codes corresponding to its assigned bed designation code and means for automatically retrieving from said plurality of bed information storage locations and for automatically outputting a report of the bed designation codes associated with a particular status code and associated with a particular occupant code.

9. A machine implemented data handling system as defined in claim 8 further comprising means for segregating said plurality of bed information storage locations into a plurality of categories and for assigning a category code to each of said plurality of categories and means for conditioning said retrieving and outputting means to retrieve said bed designation codes associated with said particular status code and associated with said particular occupant code only from the portion of said plurality of bed information storage locations associated with a specific one of said category codes to thereby limit said report of said bed designation codes to those associated with said portion of said plurality of bed information storage locations associated with said specific one of said category codes.

10. A machine implemented data handling system as defined in claim 5 wherein said data messages contain institutional bed allocation data in the form of a plurality of bed designation codes institutional bed occupant identification data in the form of a plurality of occupant codes and institutional bed status data in the form of a plurality of status codes, said machine implemented data handling system automatically maintains a record of institutional bed allocation, occupancy and status, each of said remote stations has a specific remote station address code said manual entering means further comprises means for entering a specific remote station address code corresponding to one of said remote stations into said remote station means for entering a specific bed designation code of said plurality of bed designation codes into said remote station, means for entering a specific occupant code of said plurality of occupant codes into said remote station and means for entering a specific status code of said plurality of status codes into said remote station, each of at least some of said data messages including at least one of said specific remote station address code, said specific designation code and said specific occupant code and said specific status code, and said second information storage means further comprises a plurality of bed information storage locations, said machine implemented data handling system further comprising means for extracting from said first information storage location said data messages stored therein and for transmitting said extracted data messages to said remote stations in accordance with the remote station address codes in said data messages, means for assigning a specific one of said plurality of bed designation codes to each one of said plurality of bed information storage locations, means for extracting said bed designation codes, said occupant codes and said status codes from said data messages stored in said first information storage location and for transmitting said bed designation codes, said occupant codes and said status codes to said plurality of bed information storage locations, each of said plurality of bed information storage locations receiving specific occupant and status codes corresponding to its assigned bed designation code and means for automatically retrieving from said plurality of bed information storage locations and for automatically outputting a report of the bed designation codes associated with a particular status code and associated with a particular occupant code.

11. A machine implemented data handling system for processing a plurality of data messages containing charge data and inventory data and for automatically compiling charge records organized by a plurality of charge codes from said charge data in the form of monetary charges for charge items to be charged to various ones of said plurality of charge codes and for automatically compiling inventory records organized by a plurality of item codes from said inventory data reflecting the inventory of said charge items and for periodically compiling a complete record of all of said charge records for all of said charge codes and of all of said inventory records for all of said item codes comprising means for receiving said data messages; said data messages receiving means comprising a plurality of remote stations, each of at least some of said remote stations including means for manually entering said data messages into said remote stations, said manually entering means including means for entering a specific charge code of said plurality of charge codes into said remote station, means for entering a specific item code of a plurality of item codes corresponding to a specific charge item of said charge items into said remote station and means for entering a multiplier corresponding to the quantity of said specific charge item into said remote station; each of at least some of said data messages including said specific charge code, said specific item code and said multiplier, a first information storage location, means for transmitting said data messages from said remote stations to said first information storage location for storage therein, a second information storage location, means for extracting said charge codes, said item codes and said multipliers from said data messages stored in said first information storage location and for transmitting the extracted charge codes, item codes and multipliers to said second information storage location for storage therein and means for retrieving all of said item codes and multipliers associated with each and every charge code of said plurality of said charge codes from said second information storage location and for automatically compiling and outputting sequentially by charge code a complete record of all of the charge data corresponding to each and every charge code and means for retrieving all of said item codes and multipliers associated with each and every item code of said plurality of item codes from said second information storage location and for automatically compiling and outputting sequentially by item code a complete record of all of the inventory data corresponding to each and every item code.

12. A machine implemented data handling system for processing a plurality of data messages containing charge data in the form of monetary charges organized by a first and a second plurality of charge codes for charge items to be charged to various ones of said first plurality of charge codes and corresponding to a first charge category and to be charged to various ones of said second plurality of charge codes and corresponding to a second charge category comprising means for receiving said data messages; said data messages receiving means comprising a plurality of remote stations, each of at least some of said remote stations including means for manually entering said data messages into said remote stations, said manually entering means including means for entering a specific charge code of said first plurality of charge codes or of said second plurality of charge codes into said remote station, means for entering a category indication corresponding to at least said first charge category into said remote station to distinguish the charge codes associated with said first charge category from the charge codes associated with said second charge category, means for entering a specific item code of a plurality of item codes corresponding to a specific charge item of said charge items into said remote station and means for entering a multiplier corresponding to the quantity of said specific charge item into said remote station, each of at least some of said data messages including said specific charge code, said category indication, if present, said specific item code and said multiplier, a first information storage location, means for transmitting said data messages from said remote stations to said first information storage location for storage therein, a second information storage location, means for extracting said charge codes, said category indications, said item codes and said multipliers from said data messages stored in said first information storage location and for transmitting the extracted charge codes, category indications, item codes and multipliers to said second information storage location for storage therein and means for retrieving all of said item codes and said multipliers associated with each and every one of said charge codes from said second information storage location and for automatically compiling and outputting sequentially by charge category and sequentially within said charge category by charge code all of the charge data corresponding to each and every charge code to thereby compile a complete record of all the charge data associated with all the charge codes in said first charge category and a complete record of all of the charge data associated with all of the charge codes within said second charge category.

13. A machine implemented data handling system for processing a plurality of data messages containing charge data and inventory data and for automatically compiling charge records organized by a plurality of charge codes from said charge data in the form of monetary charges for items or services to be charged to various ones of said plurality of charge codes and for automatically compiling inventory records organized by a plurality of item codes from said inventory data reflecting the inventory of said items and for automatically compiling and outputting upon demand a monetary charge summary in the form of a total sum of all of the monetary charges for said items and services charged to all of said charge codes comprising means for receiving said data messages; said data messages receiving means comprising a plurality of remote stations, each of at least some of said remote stations including means for manually entering said data messages into said remote stations, said manually entering means including means for entering a specific charge code of said plurality of charge codes into said remote station, means for entering a specific item code of said plurality of item codes corresponding to one of said items or one of said services into said remote station and means for entering a multiplier corresponding to the quantity of said one item or service into said remote station, each of at least some of said data messages including said specific charge code, said specific item code and said multiplier, a first information storage location, means for transmitting said data messages from said remote stations to said first information storage location for storage therein, a second information storage location, means for monitoring said data messages stored in said first information storage location, for automatically extracting the stored charge codes, item codes and multipliers from said data messages and for transmitting said charge codes, item codes and multipliers to said second information storage location for storage therein, means for retrieving item codes and multipliers associated with a predetermined charge code of said plurality of charge codes from said second information storage location and for automatically compiling and outputting a charge record corresponding to said predetermined charge code, means for retrieving item codes and multipliers associated with a predetermined item code of said plurality of item codes from said second information storage location and for automatically compiling and outputting an inventory record corresponding to said predetermined item code and means for automatically compiling a monetary charge summary in the form of a total sum of all of the monetary charges for all of the items and services corresponding to all of the item codes and multipliers extracted from said data messages stored in said first information storage location by said data messages monitoring means and for maintaining said monetary charge summary current by incrementing said total sum by the monetary charge for additional items and services corresponding to additional item codes and multipliers as said additional item codes and multipliers are extracted by said data messages monitoring means from said data messages stored in said first information storage location, means for storing said monetary charge summary and means for outputting said monetary charge summary upon the receipt of an output demand signal.

14. A multistation machine implemented data handling system for processing a plurality of data messages containing charge data, inventory data and station address data and for automatically compiling charge records organized by a plurality of charge codes from said charge data in the form of monetary charges for items or services to be charged to various ones of said plurality of charge codes and for automatically compiling inventory records organized by a plurality of item codes from said inventory data reflecting the inventory of said items comprising means for receiving said data messages, said data messages receiving means comprising a plurality of remote stations, each of at least some of said remote stations having a unique remote station address code, each of at least some of said remote stations including means for manually entering said data messages into said remote stations, said manually entering means including means for entering a specific remote station address code corresponding to one of said remote stations, means for entering a specific charge code of said plurality of charge codes into said remote station, and means for entering a specific item code of said plurality of item codes corresponding to one of said items or one of said services into said remote station, each of at least some of said data messages including said specific remote station address code, said specific charge code, and said specific item code, a first information storage location, means for transmitting said data messages from said remote stations to said first information storage location for at least temproary storage therein, means for extracting from said first information storage location said data messages stored therein and for transmitting said extracted data messages to said remote stations in accordance with the remote station address codes in said data messages, a second information storage information, means for monitoring said data messages stored in said first information storage location, for automatically extracting said charge codes and item codes from said data messages and for transmitting said charge codes, and item codes to said second information storage location for storage therein, means for retrieving item codes associated with a predetermined charge code of said plurality of charge codes from said second information storage location and for automatically compiling and outputting a charge record corresponding to said predetermined charge code and means for retrieving item codes associated with a predetermined item code of said plurality of item codes from said second information storage location and for automatically compiling and outputting an inventory record corresponding to said predetermined item code.

15. A multistation machine implemented data handling system for processing a plurality of data messages containing charge data, inventory data, institutional bed allocation data, institutional bed occupancy data and institutional bed status data flowing between a central processing unit and at least one of a plurality of remote stations and for automatically compiling charge records organized by a plurality of charge codes from said charge data in the form of monetary charges for items or services to be charged to various ones of said plurality of charge codes and for automatically compiling inventory records organized by a plurality of item codes from said inventory data reflecting the inventory of said items and for automatically compiling institutional bed allocation data in the form of occupancy and status information of institutional beds organized by a plurality of bed designation codes and by a plurality of occupant codes corresponding to said occupancy information and by a plurality of status codes corresponding to said status information comprising means for receiving said data messages; said data messages receiving means comprising a plurality of remote stations, each of at least some of said remote stations having a specific one of a plurality of remote station address codes, each of at least some of said remote stations including means for manually entering said data messages into said remote stations, said manually entering means including means for entering a specific remote station address code of said plurality of remote station address codes corresponding to one of said remote stations into said remote station, means for entering a specific charge code of said plurality of charge codes into said remote station, means for entering a specific item code of said plurality of item codes corresponding to one of said items or one of said services into said remote station, means for entering a multiplier corresponding to the quantity of said one item or service into said remote station, means for entering a specific bed designation code of said plurality of bed designation codes into said remote station, means for entering a specific occupant code of said plurality of occupant codes into said remote station and means for entering a specific status code of said plurality of status codes into said remote station, each of at least some of said data messages including at least one of said specific remote station address code, said specific charge code, said specific item code, said multiplier, said bed designation code, said occupant code and said status code, a first information storage means within said central processing unit, means for transmitting said data messages from said remote stations to said first information storage means for at least temporary storage therein, means for extracting from said first information storage means said data messages stored therein and for transmitting said extracted data messages to said remote stations in accordance with the remote station address codes in said data messages, a second information storage means within said central processing unit, means for monitoring said data messages stored in said first information storage means, for automatically extracting said charge codes, said item codes and said multipliers from said data messages and for transmitting said charge codes, said item codes and said multipliers to said second information storage means for storage therein, a third information storage means, said third information storage means comprising a plurality of bed information storage locations within said central processing unit, means for associating a specific bed designation code with each one of said plurality of bed information storage locations, means for monitoring said data messages stored in said first information storage means, for automatically extracting said bed designation codes, said occupant codes and said status codes from said data messages and for transmitting specific occupant and status codes corresponding to a specific bed designation code to the specific one of said plurality of bed information storage locations associated with said specific bed designation code for storage therein, means for retrieving from said plurality of bed information storage locations and for automatically outputting a report of bed designation codes corresponding to a specific occupant code or a specific status code, means for retrieving item codes and multipliers associated with a predetermined charge code of said plurality of charge codes from said second information storage means and for automatically compiling and outputting a charge record corresponding to said predetermined charge code and means for retrieving item codes and multipliers associated with a predetermined item code of said plurality of item codes from said second information storage means and for automatically compiling and outputting an inventory record corresponding to said predetermined item code.

16. A multistation machine implemented data handling system as defined in claim 15 further comprising
means for associating each one of said plurality of said occupant codes with a specific one of said plurality of charge codes,
means for retrieving all of said occupant codes from said plurality of bed information storage locations and
means for retrieving from said second information storage means all of the item codes and multipliers associated with a predetermined charge code of said plurality of charge codes having an associated occupant code and for automatically compiling and outputting a charge record corresonding to said predetermined charge code having said associated occupant code.

17. A multistation machine implemented data handling system as defined in claim 16 further comprising means for retrieving all of the item codes and multipliers associated with all of the charge codes of said plurality of charge codes that lack associated occupant codes and for automatically compiling and outputting a charge record for each and every one of said plurality of charge codes that lacks an associated occupant code.

* * * * *

UNITED STATES PATENT OFFICE
CERTIFICATE OF CORRECTION

Patent No. 4,135,241                      Dated  January 16, 1979

Inventor(s)     Eugene A. Stanis and Louis E. Philipps

It is certified that error appears in the above-identified patent and that said Letters Patent are hereby corrected as shown below:

In the Claims:

Claim 5, column 88, line 3, "items" should be --item--.

Claim 7, column 88, line 62, --remote-- should be inserted between "said" and "station".

Claim 16, column 96, line 40, "corresonding" should be --corresponding--.

*Signed and Sealed this*

*Seventeenth* Day of *April 1979*

[SEAL]

Attest:

RUTH C. MASON
*Attesting Officer*

DONALD W. BANNER
*Commissioner of Patents and Trademarks*